United States Patent
Ellinger et al.

(10) Patent No.: US 12,195,515 B2
(45) Date of Patent: Jan. 14, 2025

(54) HA-1 SPECIFIC T CELL RECEPTORS AND THEIR USE

(71) Applicant: MEDIGENE IMMUNOTHERAPIES GMBH, Planegg-Martinsried (DE)

(72) Inventors: Christian Ellinger, Munich (DE); Daniel Sommermeyer, Munich (DE); Aline Bracher, Munich (DE)

(73) Assignee: MEDIGENE IMMUNOTHERAPIES GMBH, Planegg-Martinsried (DE)

( * ) Notice: Subject to any disclaimer, the term of this patent is extended or adjusted under 35 U.S.C. 154(b) by 756 days.

(21) Appl. No.: 17/266,258

(22) PCT Filed: Aug. 6, 2019

(86) PCT No.: PCT/EP2019/071099
§ 371 (c)(1),
(2) Date: Feb. 5, 2021

(87) PCT Pub. No.: WO2020/030631
PCT Pub. Date: Feb. 13, 2020

(65) Prior Publication Data
US 2021/0300987 A1 Sep. 30, 2021

(30) Foreign Application Priority Data
Aug. 6, 2018 (EP) .................... 18187539

(51) Int. Cl.
*C07K 14/725* (2006.01)
*C07K 16/28* (2006.01)
*A61K 38/00* (2006.01)

(52) U.S. Cl.
CPC ...... *C07K 14/7051* (2013.01); *C07K 16/2833* (2013.01); *A61K 38/00* (2013.01); *C07K 2317/565* (2013.01)

(58) Field of Classification Search
CPC ............ C07K 14/7051; C07K 16/2833; C07K 2317/565; A61K 38/00
See application file for complete search history.

(56) References Cited

U.S. PATENT DOCUMENTS

| | | | |
|---|---|---|---|
| 2004/0092446 A1 | 5/2004 | Goulmy et al. | |
| 2016/0083449 A1* | 3/2016 | Schmitt | A61P 35/00 435/235.1 |
| 2020/0057048 A1* | 2/2020 | Santamaria | C07K 14/70539 |
| 2021/0128485 A1* | 5/2021 | Stephan | A61K 9/1271 |

FOREIGN PATENT DOCUMENTS

| JP | 2017007977 A | 1/2017 |
|---|---|---|
| JP | 2017169566 A | 9/2017 |
| WO | WO-03047606 A2 | 6/2003 |
| WO | WO-2017120428 A2 | 7/2017 |
| WO | WO-2018/058002 A1 | 3/2018 |

OTHER PUBLICATIONS

Knapp et al. MHC binding affects the dynamics of different T-cell receptors in different ways. PLOS Computational Biology PCBI .1007338: pp. 1/17-17/17, (2019) (Year: 2019).*
Singh et al. "emerging concepts in TCR specificity: rationalizing and (maybe) predicting outcomes," J. Immunol. 199: 2203-2213 (2017) (Year: 2017).*
Inaguma et al , "Construction and molecular characterization of a T-cell receptor-like antibody and CAR-T cells specific for minor histocompatibility antigen HA-1H," Gene Therapy 21:575-584 (2014) (Year: 2014).*
Nichols et al., "Secondary anchor polymorphism in the HA-1 minor histocompatibility antigen critically affects MHC stability and TCR recognition," PNAS 106:3889-3894 (2009) (Year: 2009).*
Dossa et al., "Development of T-cell immunotherapy for hematopoietic stem cell transplantation recipients at risk of leukemia relapse," Blood. 131(1):108-20 (2018).
International Preliminary Report on Patentability for International Patent Application No. PCT/EP2019/071099, dated Feb. 9, 2021 (12 pages).
International Search Report and Written Opinion for International Patent Application No. PCT/EP2019/071099, dated Dec. 20, 2019 (19 pages).
Mommaas et al., "Identification of a Novel HLA-B60-Restricted T Cell Epitope of the Minor Histocompatibility Antigen HA-1 Locus," J Immunol. 169(6):3131-6 (2002).
Torikai et al., "The HLA-A*0201-restricted minor histocompatibility antigen HA-1$^H$ peptide can also be presented by another HLA-A2 subtype, A*0206," Bone Marrow Transplant. 40(2):165-74 (2007).
Akatsuka et al., "Minor histocompatibility antigens as targets for immunotherapy using allogenic immune reactions," Cancer Sci. (2007) (8 pages).
Van Loenen et al., "Optimization of the HA-1-specific T-cell receptor for gene therapy of hematologic malignancies," Haematologica. 96(3): 477-481 (2011).

* cited by examiner

Primary Examiner — Julie Ha
Assistant Examiner — Kristina M Hellman
(74) Attorney, Agent, or Firm — Clark & Elbing LLP

(57) ABSTRACT

The present invention covers an isolated T cell receptor (TCR) specific for one allelic variant of minor histocompatibility antigen 1 (HA-1), in particular the allelic variant HA-1$^H$. An isolated polypeptide comprising a functional portion of the TCR is also described. Moreover, a multivalent TCR complex, nucleic acid molecules, vectors, cells, antibodies as well as medical uses that relate to the TCR are defined.

Figure 1:
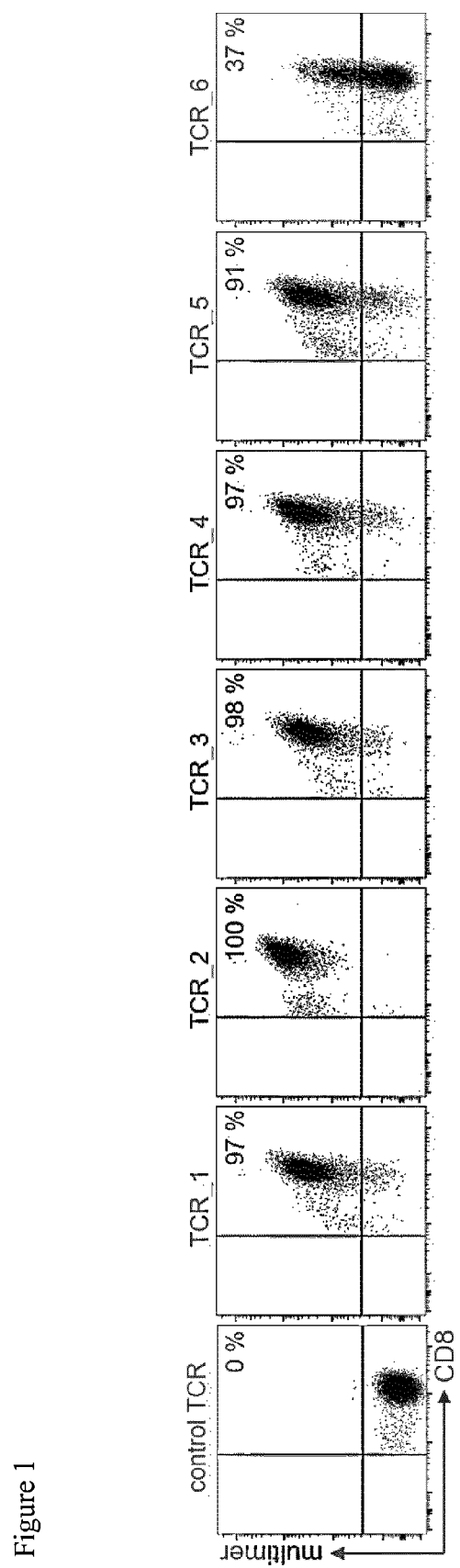

8 Claims, 10 Drawing Sheets
Specification includes a Sequence Listing.

HA-1 SPECIFIC T CELL RECEPTORS AND THEIR USE

FIELD OF THE INVENTION

The present invention relates to an isolated T cell receptor (TCR) specifically binding to one allelic form of the minor histocompatibility antigen 1 (HA-1) and to a polypeptide comprising a functional portion of the TCR. Further implicated are a multivalent TCR complex, a nucleic acid encoding a TCR, a cell expressing the TCR and a pharmaceutical composition comprising the TCR. The invention also refers to the TCR for use as a medicament, in particular to the TCR for use in the treatment of cancer.

BACKGROUND OF THE INVENTION

Bone marrow transplantation (BMT) and hematopoietic stem cell transplantation (HSCT) have successfully been used as one line of treatment of numerous malignant and nonmalignant diseases, such as severe aplastic anemia and leukemia during the last 50 years. During BMT or HSCT, a patient receives blood-forming cells (i.e. hematopoietic stem cells) from a healthy donor, after the patient's own hematopoietic cell system has been destroyed by either sub-lethal, full-body irradiation or high doses of cytotoxic drugs. The stem cells of the donor may be derived from the bone marrow of the donor or be part of a stem cell transplant of mobilized hematopoietic stem cells of the donor. This approach is termed allogeneic, since the transplanted cells are derived from a non-self-origin, i.e. a healthy, genetically non-identical donor.

One failure mode of allogeneic BMT or HSCT is due to the rejection of the graft by the host, also known as Host versus Graft Disease (HvGD) wherein residual immune cells of the patient, which escaped destruction during the pre-transplantation regimen of sub-lethal irradiation or cytotoxic medication, identify the transplanted donor cells as "foreign" and subsequently elicit an immune response leading to the rejection of the grafted bone marrow or hematopoietic stem cells.

Another even more severe form of failure of BMT/HSCT is the so called Graft versus Host Disease (GvHD) which in effect is a reaction of the grafted immune cells, originating from the bone marrow or hematopoietic stem cells transplanted from the donor, against the somatic cells of the patient (recipient). GvHD is mainly due to the difference in the MHC molecules expressed by all nucleated somatic cells and platelets. MHC stands for major histocompatibility complex molecules of which two primary classes are known. MHC class I molecules, which present or display peptide fragments of cytosolic proteins play a major role in GvHD. In humans, MHC is also called the HLA complex (human leukocyte antigen complex) and is located on chromosome 6.

The HLA complex is polygenic and based on highly polymorphic genes, which means that there are many different alleles (alternative forms of the same gene) in the different individuals of a population. Each human cell expresses six different MHC class I alleles (one HLA-A, -B, and -C allele from each parent) and an additional six to eight MHC class II alleles. In the BMT and HSCT setting, the MHC molecules themselves can act as antigens, i.e. they can be identified as "foreign" by the donor's immune cells. Thus the GvHD response is primarily based on a mismatch of the HLA/MHC molecule expression of donor and recipient. Accordingly, it is paramount to select the donor for the least amount of mismatch in regard to MHC class I and class II phenotype for least risk of GvHD.

Even though donor and patient are matched as closely as possible regarding their MHC I/II genotype, more than 50% of all patients still suffer from GvHD. One possible way of preventing patients from developing GvHD is the removal of T cells from the graft using for example anti-CD3 monoclonal antibodies or other antibodies specific for mature T cells since the donor's T cells elicit the GvHD by recognizing the patient's HLA molecules that differ from the donor's repertoire. Although BMT and HSCT are currently carried out in a HLA-matched setting, GvHD still occurs in a large number of patients resulting in a need to overcome this problem.

This is likely due to a mismatch in so called minor histocompatibility antigens (MiHA), which are inherited independently of the HLA genes. During the last years a large number of MiHAs have been identified (Frontiers in Immunology, Vol. 7, Article 100, March 2016) which can be encoded by the male-specific Y-chromosome (H-Y antigens) or other chromosomes (autosomal MiHA). Of the autosomal MiHAs, the antigens termed HA-1, 2, 3, 4 and 5 were the first antigens which were discovered and all of these are either presented in the context of HLA-A1 (HA-3) or in the context of HLA-A2 (HA-1, 2, 4 and 5). It is also known that the SNP variant (Single Nucleotide Polymorphism) defining the MiHAs of HA-1 is expressed in 69% of patients expressing HLA-A2, whereas HA-2 can be detected in 95%, HA-4 in 16% and HA-5 in about 7% of the population. In contrast, HA-3, which is presented in the context of HLA-A1 is found in 88% of patients expressing HLA-A1 (N Engl J Med. 1996 Feb. 1; 334 (5): 281-5).

Since HA-1 is expressed almost solely on hematopoietic cells and carcinoma cells, it represents a promising tumor specific target for adoptive T cell therapy (ACT). Previously, HLA-A2 restricted HA-1 specific cytotoxic T lymphocytes (T cells) have been successfully isolated or generated (Haematologica. 2005 October; 90 (10): 1415-21). HA-1 comprises an epitope in form of a nona-peptide (Science. 1998 Feb. 13; 279 (5353): 1054-7) having the amino-acid sequence VLHDDLLEA (SEQ ID NO: 2) and is derived from the allele (SNP variant) of the HMHA1 (KIAA0223) gene (rs number: rs1801284). The HMHA1 locus comprises two alleles, HA-1H and HA-1R, which differ in two nucleotides, resulting in a single amino acid substitution. The second nona-peptide epitope, namely VLRDDLLEA (SEQ ID NO: 4; Science 13 Feb. 1998: Vol. 279, Issue 5353, pp. 1054-1057) is presented less efficiently by HLA-A*02:01. Due to the allelic polymorphism and Mendelian segregation pattern, individuals can either be homozygous for HA-1$^{H/H}$, heterozygous HA-1$^{H/R}$ or homozygous HA-1$^{R/R}$.

OBJECTIVES AND SUMMARY OF THE INVENTION

One objective of the present invention was the provision of T cell receptors which specifically bind to only one allelic variant of the MiHA HA-1.

The present invention relates to T cell receptors (TCRs) being specific for only one allelic version of HA-1, namely HA-1$^H$. In a specific embodiment of the invention, T cell receptors are disclosed having binding specificity for HA-1$^H$ as presented by or in the context of HLA-A2 molecules. The invention also relates to the TCRs for use as a medicament or for the use in the therapy of malignancies. TCRs can be used for example in a setting wherein a BMT/HSCT patient is either homozygous for the HA-1 H-allele (presenting the peptide VLHDDLLEA (SEQ ID NO: 2) on a suitable MHC/HLA molecule), i.e. the patient is HA-1$^{H/H}$, or heterozygous, i.e. HA-1$^{H/R}$ and wherein the donor is homozygous for the R-allele, i.e. HA-1$^{R/R}$, and a part of the donor T cells have been isolated and transduced with one of the inventive TCRs, thus expressing a TCR having specificity for the HA-1$^{H}$ allele, and wherein the transduced donor T cells are infused into the patient and wherein the patient and donor are otherwise HLA-identical or HLA-matched. The infused recombinant donor T cells expressing HA-1$^{H}$ specific TCRs detect and deplete (via cytotoxic activity) any residual hematopoietic tumor cells of the patient expressing HA-1$^{H}$ in the context of a suitable MHC/HLA molecule. It is also envisioned to conserve such HA-11 specific donor T cells for future infusion to enable depletion of tumor cells of the patient reemerging during a relapse of the tumor. Another aspect of the present invention is the use of the inventive TCRs or recombinant T cells expressing the inventive TCRs for pre-conditioning treatment of patients scheduled for a BMT/HSCT. By such use of the inventive TCRs or recombinant T cells expressing such HA-1$^{H}$ specific TCRs, sub-lethal irradiation could be replaced or supported by the infusion of such recombinant T cells which are, due to the recombinant expression of the inventive TCR, alloreactive against the hematopoietic cells of the patient and would thus eradicate immune cells presenting HA-1$^{H}$ in a HLA-A2 context. The T cells can be derived from the donor of the BMT/HSCT.

The TCR according to the invention is isolated and/or purified and may be soluble or membrane bound.

In some embodiments, the amino acid sequence of the TCR may comprise one or more phenotypically silent substitutions. In addition, the TCRs of the invention can be labelled. Useful labels are known in the art and can be coupled to the TCR or TCR variant using routine methods, optionally via linkers of various lengths. The term "label" or "labelling group" refers to any detectable label. Additionally, or alternatively, the amino acid sequence may be modified to comprise a therapeutic agent or pharmacokinetic modifying moiety. The therapeutic agent may be selected from the group consisting of an immune effector molecule, a cytotoxic agent and a radionuclide. The immune effector molecule may for example be a cytokine. The pharmacokinetic modifying moiety may be at least one polyethylene glycol repeating unit, at least one glycol group, at least one sialyl group or a combination thereof.

The TCR, in particular a soluble form of the TCR according to the invention can be modified by attaching additional functional moieties, e.g. for reducing immunogenicity, increasing hydrodynamic size (size in solution) solubility and/or stability (e.g. by enhanced protection to proteolytic degradation) and/or extending serum half-life. Other useful functional moieties and modifications include "suicide" or "safety switches" that can be used to shut off or turn on effector host cells carrying an inventive TCR in a patient's body.

TCRs with an altered glycosylation pattern are also envisaged herein.

It is also conceivable to add a drug or a therapeutic entity, such as a small molecule compound to the TCR, in particular to a soluble form of the inventive TCR.

The TCR, in particular a soluble form of the inventive TCR can additionally be modified to introduce additional domains which aid in identification, tracking, purification and/or isolation of the respective molecule (tags).

In some embodiments, the TCR is of the single chain type, wherein the TCR α chain and the TCR β chain are linked by a linker sequence.

Another aspect of the invention refers to a polypeptide comprising a functional portion of the TCR as described herein, wherein the functional portion comprises at least one of the amino acid sequences selected from the group consisting of SEQ ID NOs: SEQ ID NO: 7, SEQ ID NO: 17, SEQ ID NO: 27, SEQ ID NO: 37, SEQ ID NO: 47 SEQ ID NO: 57, SEQ ID NO: 10, SEQ ID NO: 20, SEQ ID NO: 30, SEQ ID NO: 40 SEQ ID NO: 50 and SEQ ID NO: 60.

In specific embodiments, the functional portion comprises the TCR α variable chain and/or the TCR β variable chain.

Specific embodiments refer to a multivalent TCR complex comprising a least two TCRs as described herein. In a more specific embodiment, at least one of said TCRs is associated with a therapeutic agent.

Some embodiments refer to the inventive TCR expressed on an effector cell, especially on an immune effector cell as a functional polypeptide or functional multivalent polypeptide, wherein IFN-γ secretion is induced in the aforementioned effector cell expressing the TCR upon binding to the amino acid sequence SEQ ID NO: 2, which is presented by the HLA-A*02:01 encoded molecule.

Wherein presentation by the HLA-A*02:01 encoded molecule means that the peptide, in particular the epitope is binding to the binding-groove of the MHC molecule.

The MHC molecule presenting the epitope may be encoded by one of the HLA-A*02 alleles, such as the HLA-A*02:01 or the HLA-A*02:06 alleles, preferably the HLA-A*02:01 allel.

The IFN-γ secretion induced by binding of the inventive TCR expressed on an effector cell to the amino acid sequence of SEQ ID NO: 2, which is presented by the HLA-A*02:01 encoded molecule, may be at least 3 times higher, such as 10 times higher, 20 times higher, 100 times higher when compared to the binding to SEQ ID NO: 4, which is presented by the HLA-A*02:01 encoded molecule, at a HA-1 peptide concentration of 10$^{-7}$ [M]. Thus, for recognition of the HA-1$^{R}$-variant at least 1,000, preferred at least 5,000, more preferred at least 8,000, most preferred at least 10,0000 times higher peptide concentrations compared to HA-1$^{H}$ are needed for all of the HA-1$^{H}$-TCR-transgenic T cells.

In specific embodiments, for example when the ratio of TCR-transgenic T cells to T2 cells is 2:1, the IFN-γ secretion induced by binding of the inventive TCR expressed on an effector cell to the amino acid sequence of SEQ ID NO: 2, which is presented by the HLA-A*02:01 encoded molecule, may be more than 500 pg/ml, such as more than 1000 pg/ml, more preferably more than 2000 pg/ml, most preferably more than 3000 pg/ml at a HA-1 peptide concentration of 10$^{-7}$ [M].

The cytokine and chemokine release, such as IFN-γ secretion may be measured using T cell antibody immobilized magnetic beads by an in vitro assay in which K562 cells (Greiner et al. 2006, Blood. 2006 Dec. 15; 108 (13): 4109-17) are transduced to express the amino acid sequence of SEQ ID NOs: 2 or SEQ ID NOs: 4, respectively, are incubated with CD8$^{+}$ enriched and/or non-CD8$^{+}$-enriched PBMC expressing the TCR to be investigated or in an in vitro assay using T2 cells externally loaded with either the VLHDDLLEA peptide (SEQ ID NO: 2) or the peptide VLRDDLLEA (e.g. SEQ ID NO: 4) and subsequently co-incubated with CD8$^{+}$ enriched and/or non-CD8$^{+}$-enriched PBMC expressing the TCR to be investigated.

Another aspect of the invention refers to a nucleic acid encoding a TCR as described herein or encoding the polypeptide as described above.

A further aspect of the invention refers to a plasmid or vector comprising the nucleic acid of the present application as described above. Preferably, the vector is an expression vector or a vector suitable for the transduction or transfection of cells, especially eukaryotic cells. The vector may be for example a retroviral vector, for example a gamma-retroviral or lentiviral vector.

Another aspect of the invention refers to a cell expressing the TCR as described herein. The cell may be isolated or non-naturally occurring.

Another aspect of the invention refers to a cell comprising the nucleic acid as described above or the plasmid or vector as described above. More specifically, the cell may comprise:
a) an expression vector which comprises at least one nucleic acid as described above, or
b) a first expression vector which comprises a nucleic acid encoding the alpha chain of the TCR as described herein, and a second expression vector which comprises a nucleic acid encoding the beta chain of a TCR as described herein.

The cell may be a peripheral blood lymphocyte (PBL) or a peripheral blood mononuclear cell (PBMC). Typically, the cell is an immune effector cell, especially a T cell. Other suitable cell types include gamma-delta T cells, NK cells and NK-like T cells.

Another aspect refers to an antibody or antigen binding fragment thereof specifically binding to a portion of the TCR as described herein which mediates specificity for HA-1$^H$. In a specific embodiment, the portion of the TCR that mediates the HA-1$^H$ specificity comprises the CDR3 of the alpha chain of SEQ ID NO: 7, SEQ ID NO: 17, SEQ ID NO: 27, SEQ ID NO: 37, SEQ ID NO: 47, SEQ ID NO: 57 and/or the CDR3 of the beta chain of SEQ ID NO: 10, SEQ ID NO: 20, SEQ ID NO: 30, SEQ ID NO: 40, SEQ ID NO: 50 and SEQ ID NO: 60.

Another aspect of the invention refers to a pharmaceutical composition comprising the TCR as described herein, the polypeptide as described herein, the multivalent TCR complex as described herein, the nucleic acid as described herein, the vector as described herein, the cell as described herein, or the antibody as described herein.

Typically, the pharmaceutical composition comprises at least one pharmaceutically acceptable carrier.

Another aspect of the invention refers to TCR as described herein, the polypeptide as described herein, the multivalent TCR complex as described herein, the nucleic acid as described herein, the vector as described herein, the cell as described herein, or the antibody as described herein for use as a medicament, in particular for use in the treatment of cancer in particular in the treatment of hematological cancer in the setting of a HLA-matched bone-marrow and/or stem cell transplantation, wherein the patient has previously received an allo bone-marrow and/or stem cell transplant from an HLA matched donor, wherein the donor is HA-1$^H$ negative (and thus HA-1$^R$ homozygous and/or HLA-A2 negative) and wherein the patient (being homozygous HA-1$^H$ or heterozygous HA-1$^{H/R}$ and HLA-A2 positive) is suffering from a relapse or reoccurrence of hematological cancer cells or as a preventive measure (patient is treated post transplantation without signs of a relapse/reoccurrence). The patient suffering from a relapse of the hematological cancer cells is treated by isolating CD8$^+$ T cells post transplantation from the patient or the donor and transducing such isolated CD8$^+$ T cells ex vivo with the TCR according to the present invention. The hematological cancer may be selected from the group consisting of, non-Hodgkin's lymphoma (NHL), Hodgkin's lymphoma (HL), multiple myeloma, acute myeloid leukemia (AML) and acute lymphoblastic leukemia (ALL), mixed phenotype acute leukemia (MPAL), chronic myeloid leukemia (CML), B cell polymorphic lymphoma, hairy cell leukemia, chronic lymphocytic leukemia (CLL), small lymphocytic lymphoma (SLL), central nervous system lymphoma, CD37+ dendritic cell lymphoma, lymphoplasmatic lymphoma, splenic marginal zone lymphoma, plasma cell myeloma, extraosseous plasmacytoma, extra-nodal marginal zone B-cell lymphoma of mucosa-associated lymphoid tissue (MALT tissue), nodal marginal zone B-cell lymphoma, follicular lymphoma, mantel cell lymphoma, diffuse large B-cell lymphoma, mediastinal (thymic) large B-cell lymphoma, precursor B-lymphoblastic lymphoma, immunoblastic large cell lymphoma, intravascular large B-cell lymphoma, primary effusion lymphoma, Burkitt's lymphoma/leukemia, B-cell proliferations of uncertain malignant potential, lymphomatoid granulomatosis, post-transplant lymphoproliferative disorder. Other hematological cancers or disorders include myelodysplastic disorder.

FIGURE LEGENDS

FIG. 1 shows the HA-1$^H$-MHC-multimer binding of CD8$^+$ T cells transduced with different HA-1$^H$-reactive TCRs. CD8 T cells were isolated from PBMCs of a healthy donor and transduced with six different HA-1$^H$-TCRs and one control TCR that did not recognize HA-1$^H$. Transduced CD8 T cells were enriched by FACS using the murine constant beta region as a marker for transduction. After expansion of these cells, they were stained with an HA-1$^H$-MHC-multimer and antibodies against CD8 and the murine constant beta region (mCb) and analyzed by flow cytometry. Populations were gated on live CD8$^{30}$/mCb$^+$ cells and staining of multimer/CD8 is shown.

Figure 2:
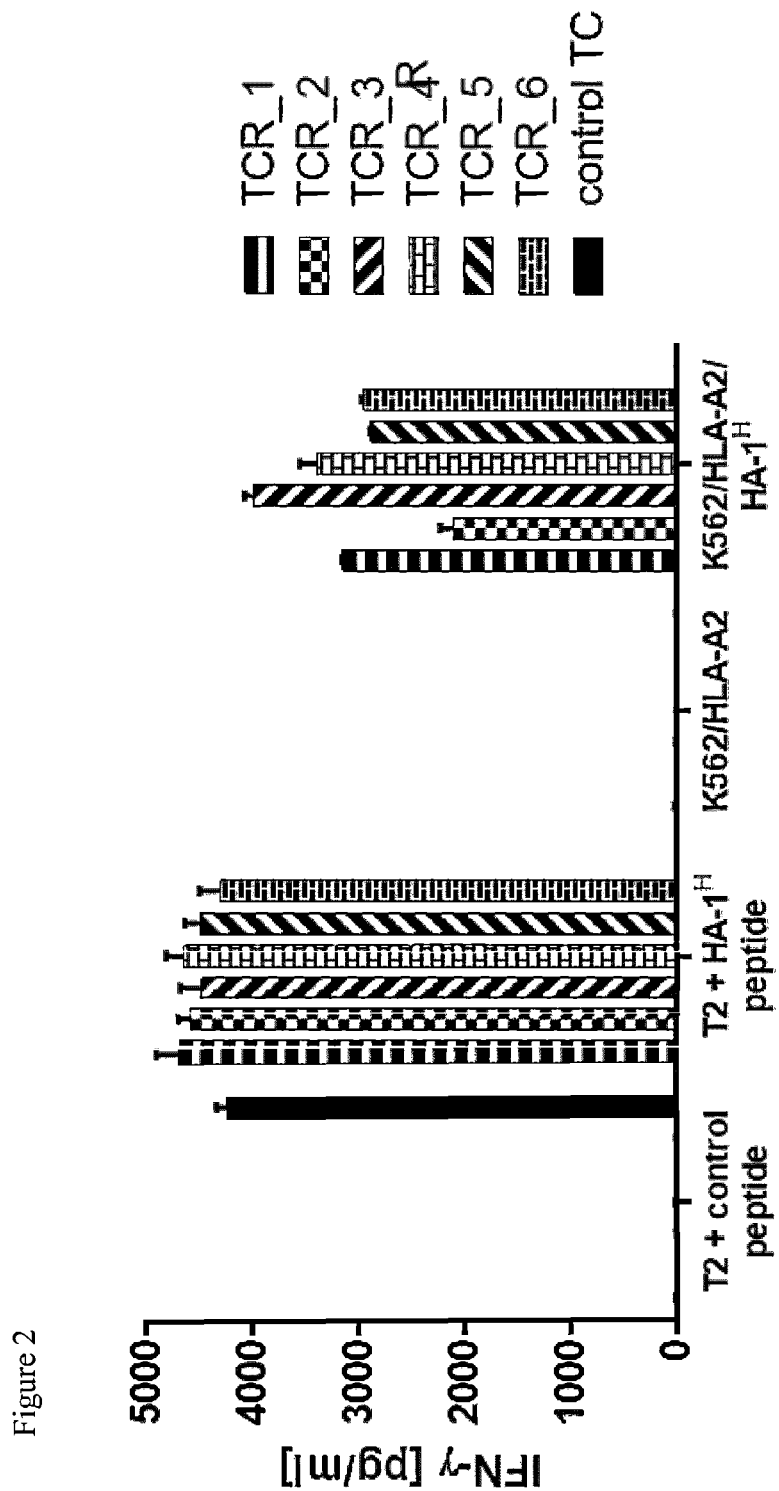

FIG. 2 shows that HA-1$^H$-TCR-transgenic T cells recognize HA-1$^H$-peptide presented on HLA-A2. Transgenic T cells were co-cultured with T2 cells externally loaded with HA-1$^H$-peptide or K562/HLA-A2 cells that had been transduced with part of HMHA1 gene encoding the HA-1$^H$-epitope. As negative controls T2 cells loaded with a control peptide and untransduced K562/HLA-A2 cells were used, respectively. Recognition of target cells was analyzed by measuring the IFN-γ concentration in co-culture supernatants by a standard ELISA.

Figure 3:
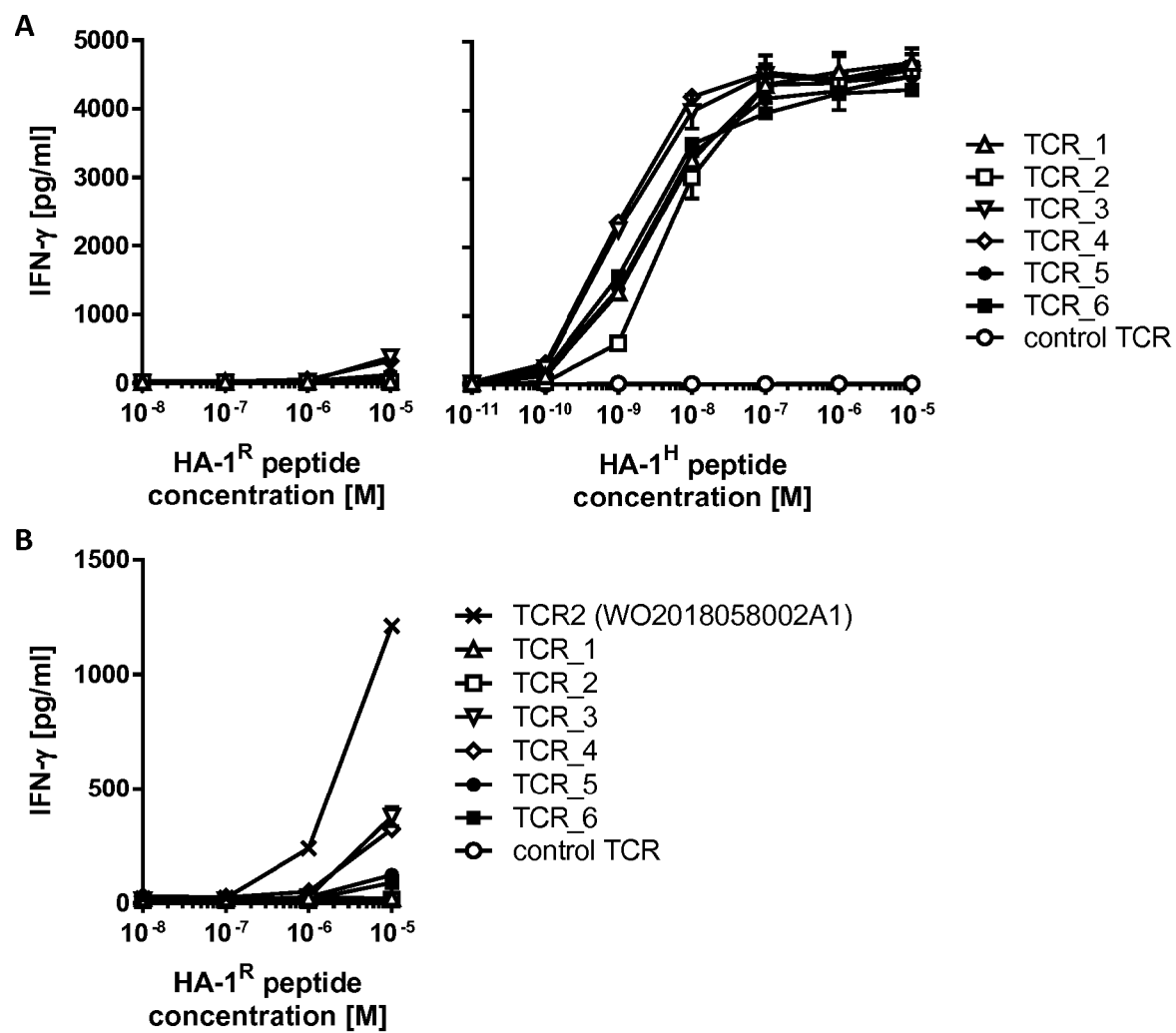

FIGS. 3A and 3B show the functional avidity of HA-1$^H$-TCR-transgenic T cells. (A) Transgenic T cells were co-cultured with T2 cells externally loaded with graded concentrations of HA-1$^H$-peptide ($10^{-11}$ M-$10^{-5}$ M) or HA-1$^R$-peptide ($10^{-8}$ M-$10^{-5}$ M). (B) Functional avidity against HA-1$^R$-peptide of HA-1$^H$-TCR-transgenic T cells was compared to T cells transduced with a HA-1-specific TCR (TCR2) as described in WO2018058002A1. Data for TCRs 1-6 according to the invention (TCR_1, TCR_2, TCR_3, TCR_4, TCR_5, TCR_6) are the same in FIGS. 3A and 3B.

Figure 4:
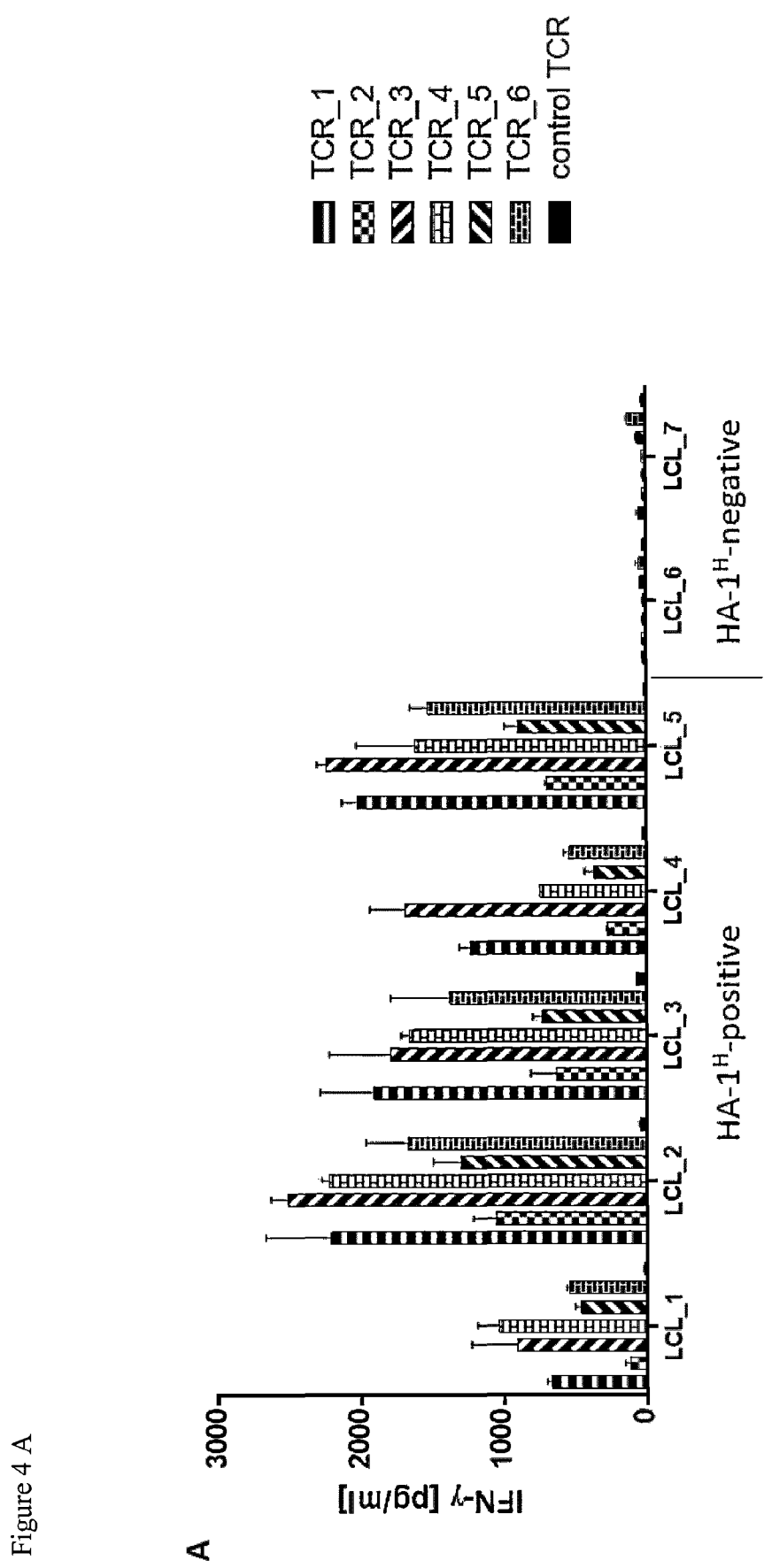
Figure 4:
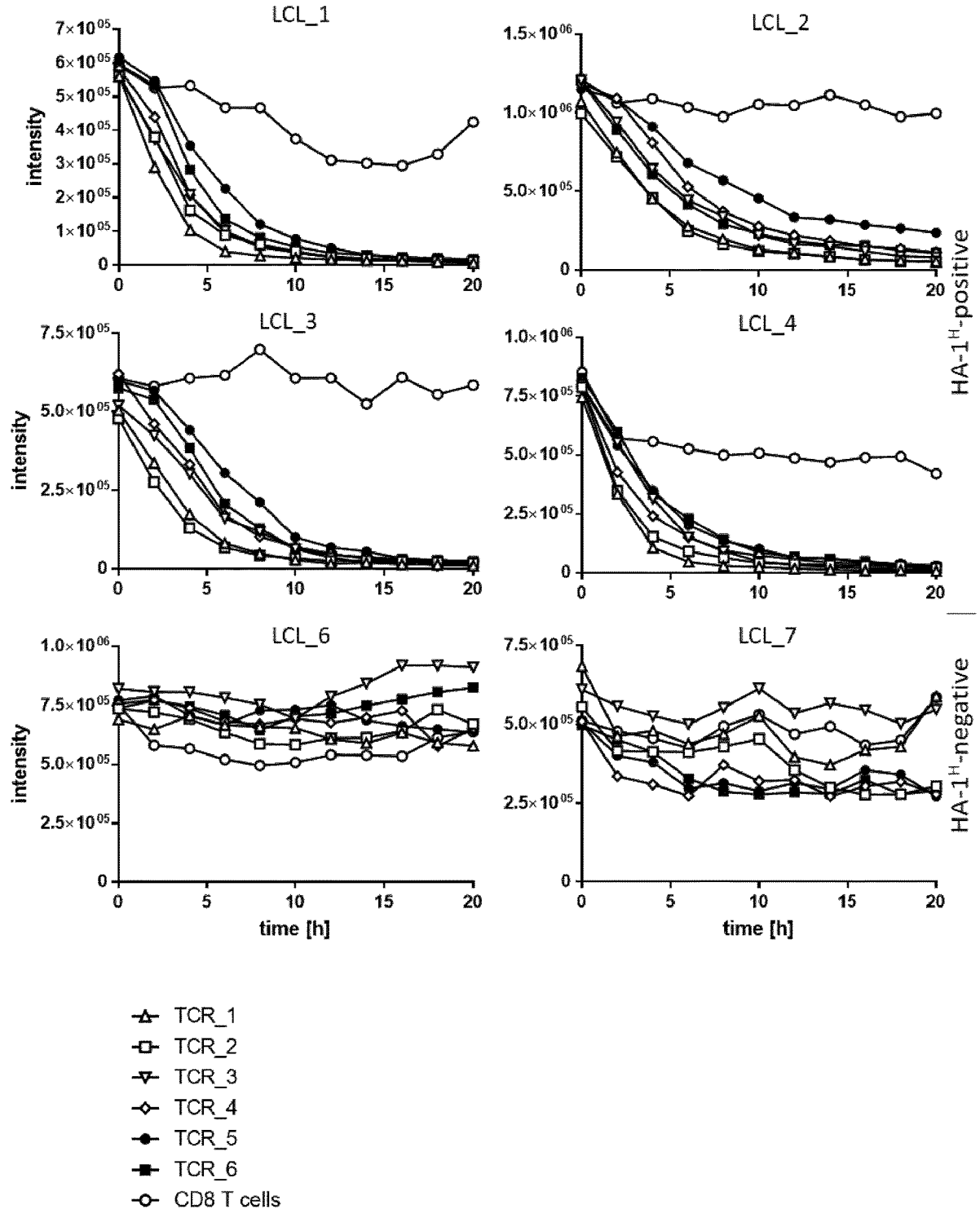

FIGS. 4A and 4B show the ability of HA-1$^H$-TCR-transgenic T cells to recognize HA-1$^H$ at physiological levels on unmodified target cells. Transgenic T cells were co-cultured with different lymphoblastoid cell lines (LCL), that were either HA-1$^H$-positive (LCL 1-5) or HA-1H-negative (LCL 6-7). (A) Cytokine release was analyzed by measuring the IFN-γ concentration in co-culture supernatants by a standard ELISA. T cells expressing a control TCR were used as a negative control. (B) Cytotoxicity against LCLs stably transduced with a fluorescence marker was measured with an IncuCyte® ZOOM (Essen BioScience) by taking pictures of the co-culture every two hours. Untransduced CD8 T cells were used as a negative control.

Figure 5:
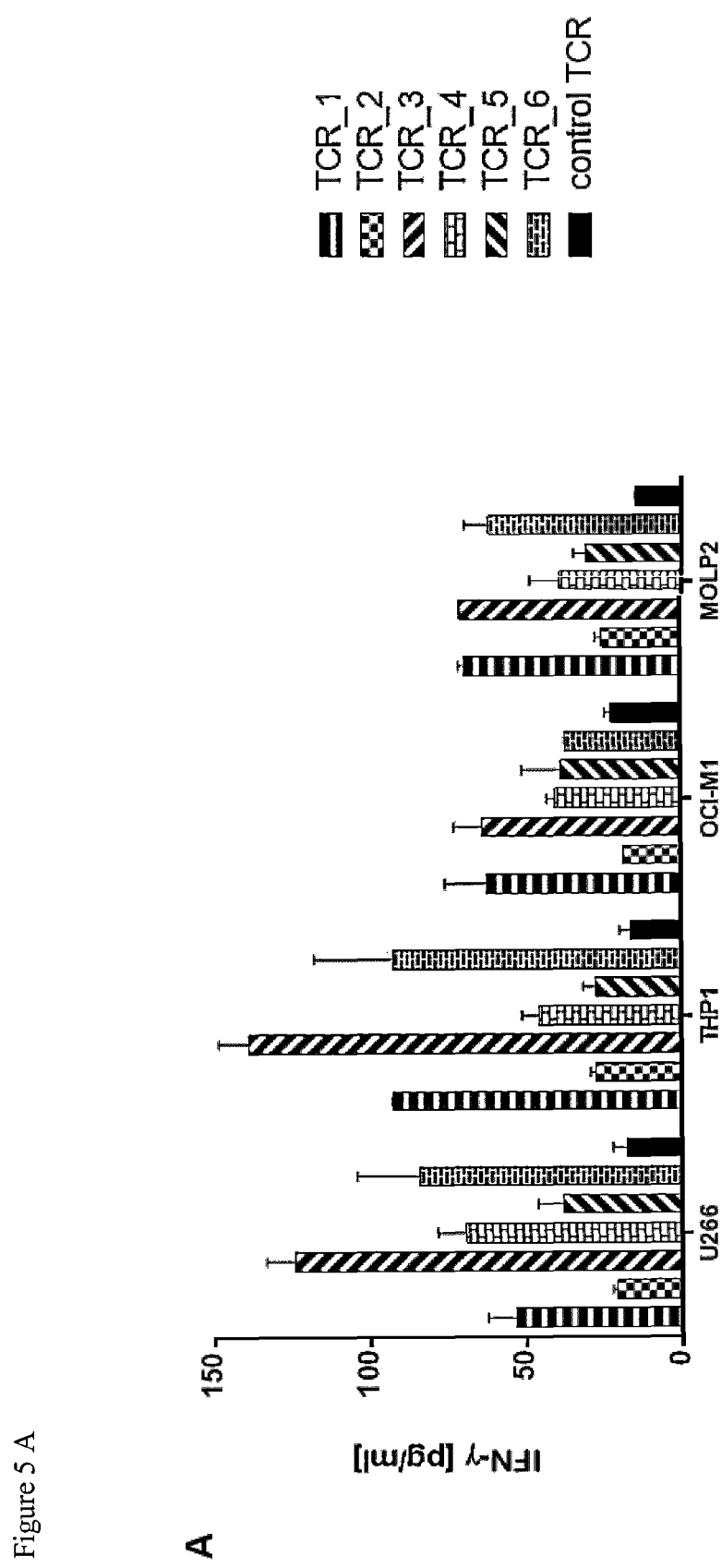
Figure 5:
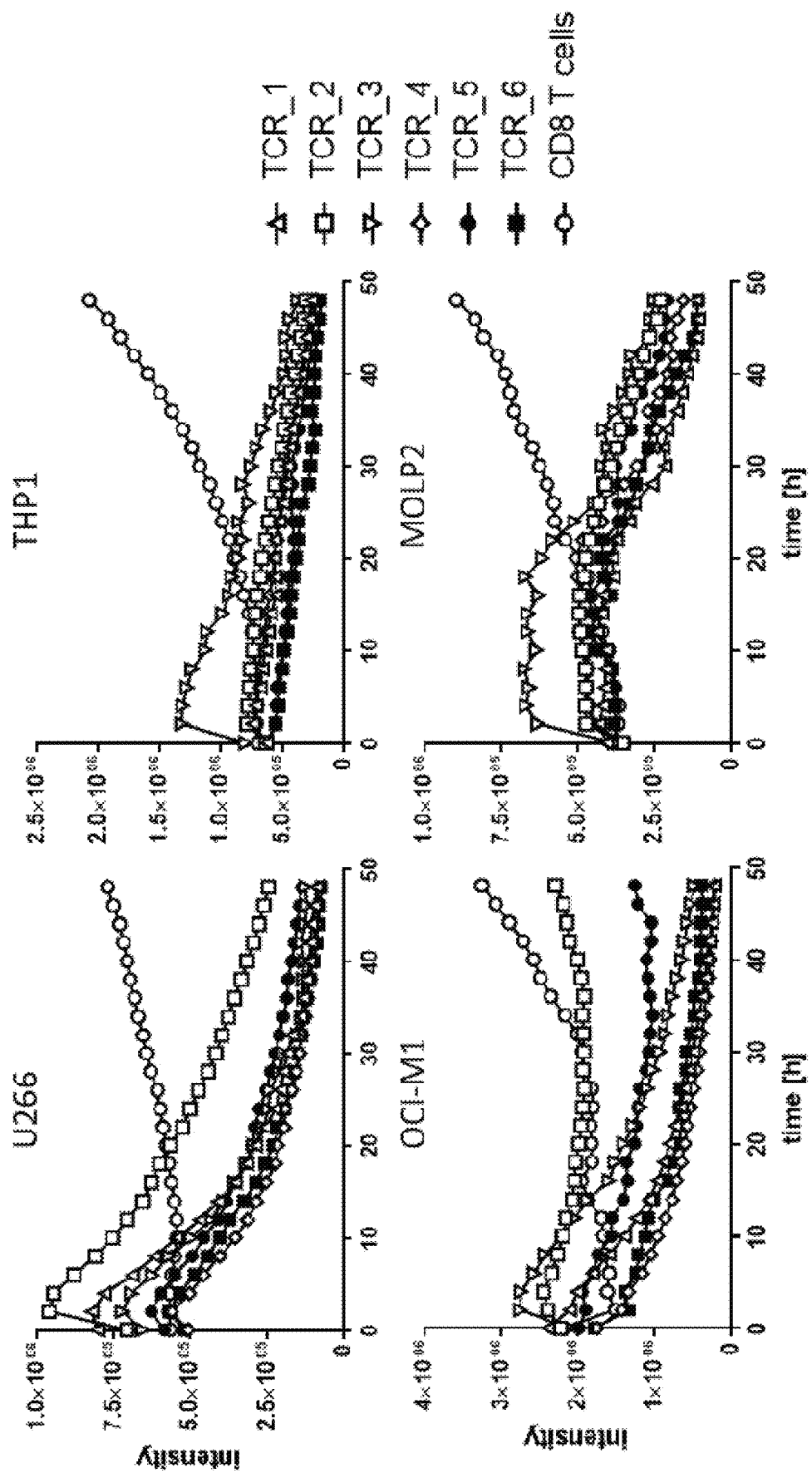

FIGS. 5A and 5B show the ability of HA-1$^H$-TCR-transgenic T cells to recognize HA-1$^H$ presented on tumor cell lines. Transgenic T cells were co-cultured with different HA-1$^H$ positive tumor cell lines. (A) Cytokine release was analyzed by measuring the IFN-γ concentration in co-culture supernatants by a standard ELISA. (B) Cytotoxicity against tumor cell lines stably transduced with a fluorescence marker was measured with an IncuCyte® ZOOM by taking pictures every two hours.

Figure 6:
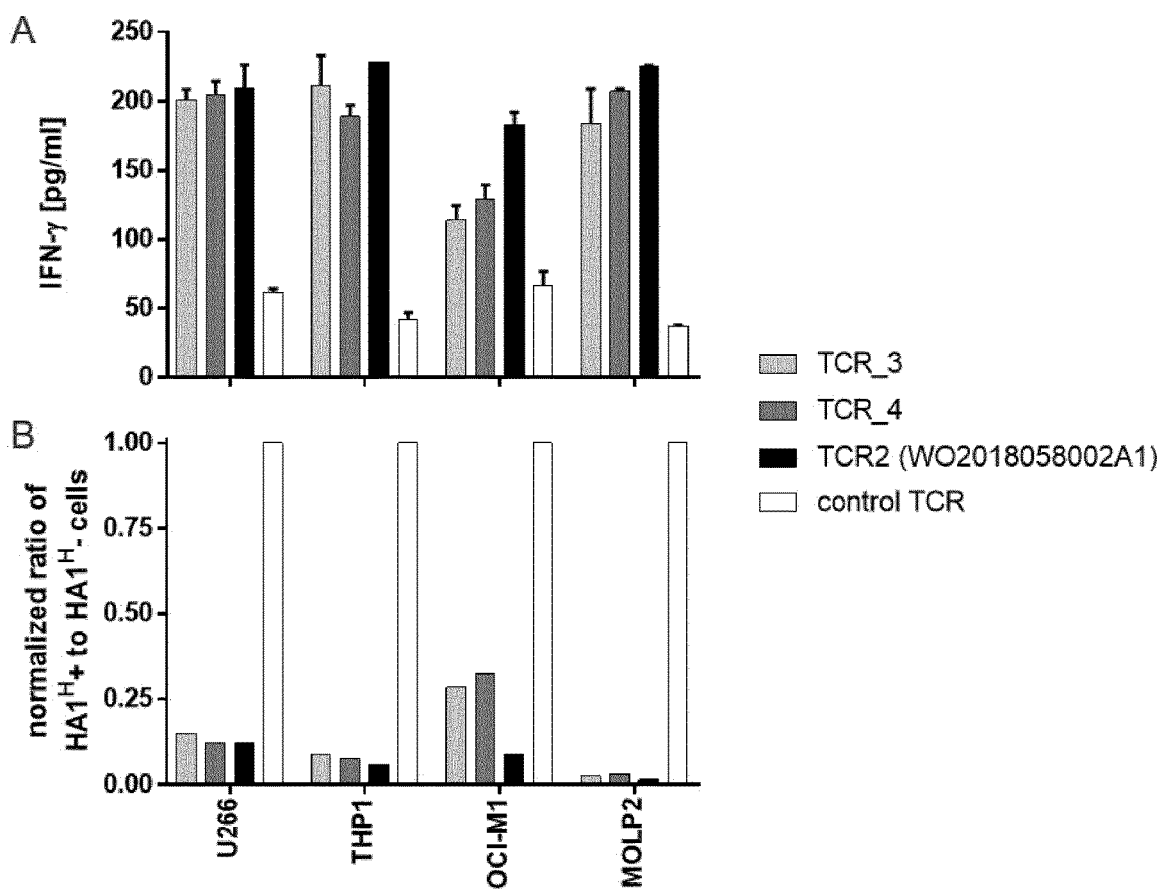

FIGS. 6A and 6B show the ability of T cells expressing TCR_3 or TCR_4 to recognize and lyse (kill) HA-1$^H$-positive tumor cell lines in comparison to TCR2 as described in WO2018058002A1. (A) Transgenic T cells were co-cultured with different HA-1$^H$-positive tumor cell lines. Cytokine release was analyzed by measuring the IFN-γ concentration in co-culture supernatants by a standard ELISA. (B) Cytotoxicity against HA-1$^H$-positive tumor cell lines was analyzed be flow cytometry. HA-1$^H$-negative/GFP-positive K562 cells and HA-1$^H$-positive/mCherry-positive cells of a tumor cell line were mixed at a ratio of 1:1 and co-cultured with TCR-transgenic T cells. The ratio of mCherry-positive (HA-1$^H$-positve) to GFP-positive (HA-1$^H$-negative) cells after 45 h was calculated and normalized to the ratio measured for the control TCR. Lower numbers indicate lysis of the HA-1$^H$-positve tumor cells due to T cell cytotoxicity.

Figure 7:
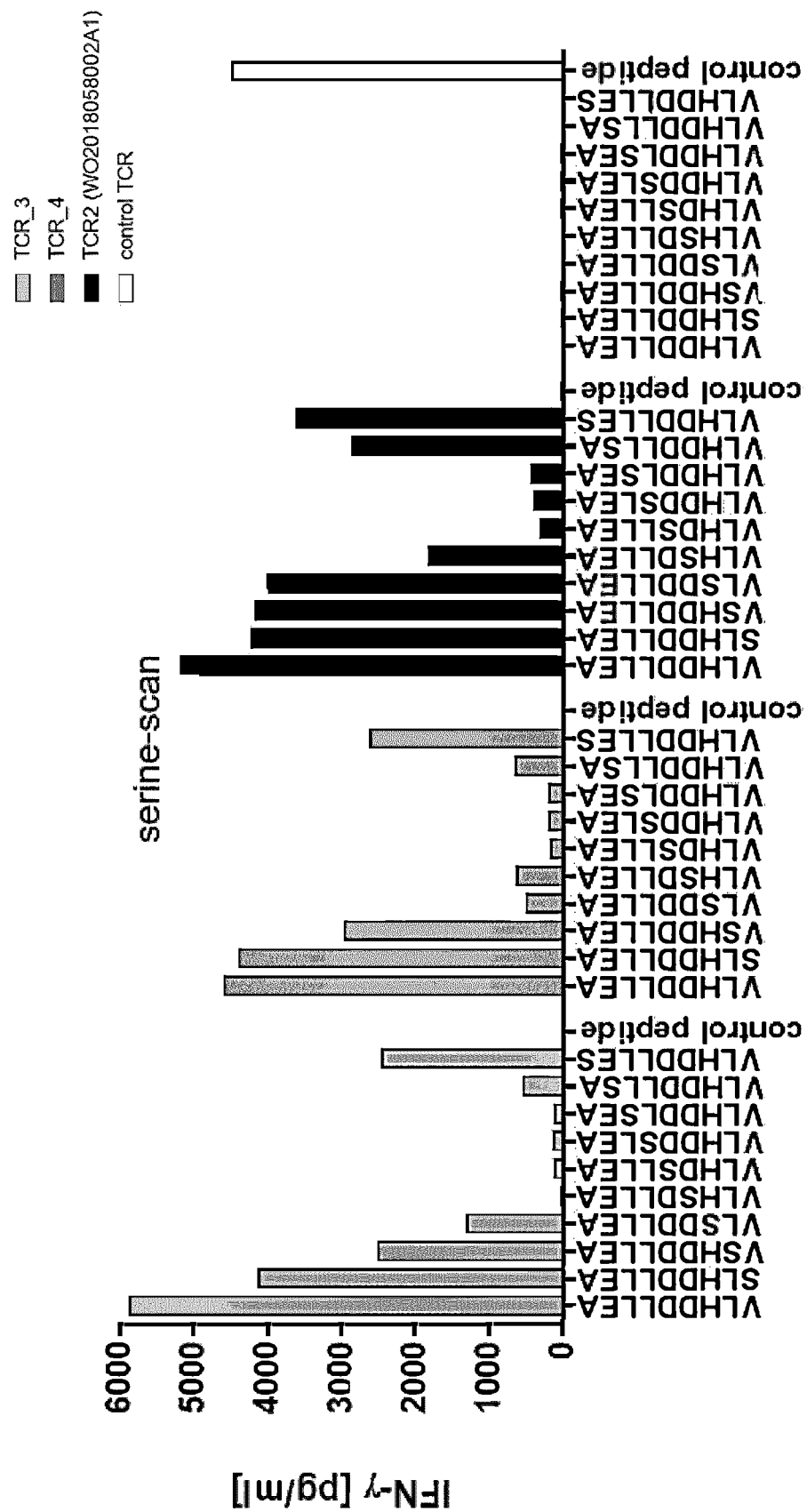

FIG. 7 shows the analysis of the recognition motifs of TCR_3 and TCR_4 in comparison to TCR2 as described in WO2018058002A1. Transgenic T cells were co-cultured with T2 cells externally loaded with HA-1$^H$-peptide, with peptides having each individual amino acid residue consecutively substituted by serine or with a control peptide.

Figure 8:
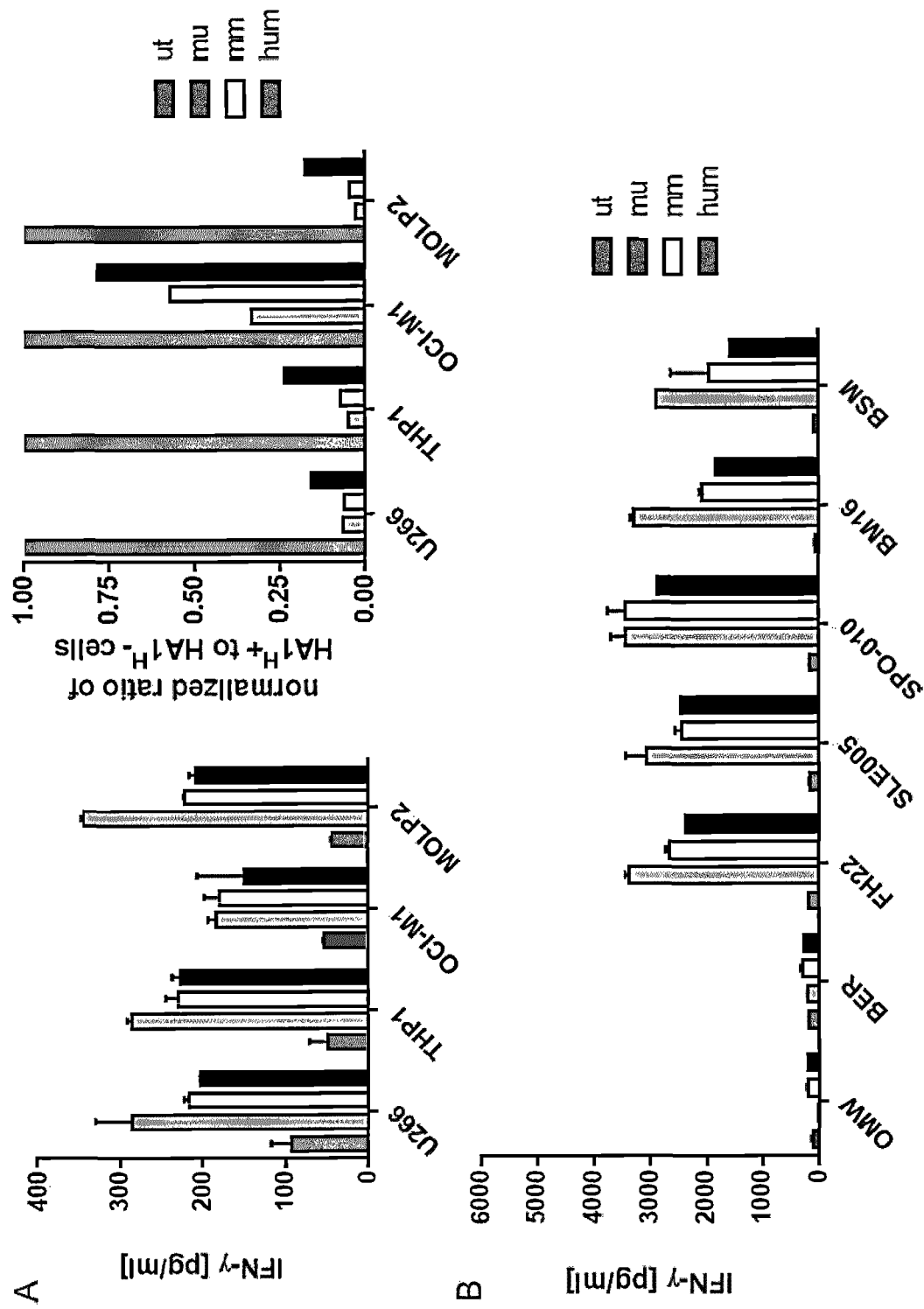

FIGS. 8A and 8B show the comparison of different constant TCR regions. TCR_3 was cloned either with murine, minimally murinized or human constant TCR regions. (A) Transgenic T cells were co-cultured with different HA-1$^H$-positive tumor cell lines. Cytokine release was analyzed by measuring the IFN-γ concentration in co-culture supernatants using standard ELISA. Cytotoxicity against HA-1$^H$-positive tumor cell lines was analyzed by flow cytometry. HA-1$^H$-negative/GFP-positive K562 cells and HA-1$^H$-positive/mCherry-positive cells of a tumor cell line were mixed in a ratio of 1:1 and co-cultured with TCR-transgenic T cells. After 45 h, the ratio of mCherry-positive (HA-1$^H$-positve) to GFP-positive (HA-1$^H$-negative) cells was calculated and normalized to the ratio measured for the control TCR. Lower numbers indicate lysis of the HA-1$^H$-positve tumor cells. (B) Transgenic T cells were co-cultured with different HA-1$^H$-negative (OMW, BER) and HA-1$^H$-positive (FH22, SLE005, SPO-010, BM16, BSM) LCL (lymphoblastoid cell lines). Cytokine release was analyzed by measuring the IFN-γ concentration in co-culture supernatants by a standard ELISA.

DETAILED DESCRIPTION OF THE INVENTION

Before the invention is described in detail with respect to some of its preferred embodiments, the following general definitions are provided.

The present invention as illustratively described in the following may suitably be practiced in the absence of any element or elements, limitation or limitations, not specifically disclosed herein.

The present invention will be described with respect to particular embodiments and with reference to certain figures but the invention is not limited thereto but only by the claims.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group which preferably consists only of these embodiments.

For the purposes of the present invention, the term "obtained" is considered to be a preferred embodiment of the term "obtainable". If hereinafter e.g. an antibody is defined to be obtainable from a specific source, this is also to be understood to disclose an antibody which is obtained from this source.

Where an indefinite or definite article is used when referring to a singular noun, e.g. "a", "an" or "the", this includes a plural of that noun unless something else is specifically stated. The terms "about" or "approximately" in the context of the present invention denote an interval of accuracy that the person skilled in the art will understand to still ensure the technical effect of the feature in question. The term typically indicates deviation from the indicated numerical value of +10%, and preferably of +5%.

Technical terms are used by their common sense or meaning to the person skilled in the art. If a specific meaning is conveyed to certain terms, definitions of terms will be given in the following in the context of which the terms are used.

TCR Background

A TCR is composed of two different and separate protein chains, namely the TCR alpha (α) and the TCR beta (β) chain. The TCR α chain comprises variable (V), joining (J) and constant (C) regions. The TCR β chain comprises variable (V), diversity (D), joining (J) and constant (C) regions. The rearranged V (D) J regions of both the TCR α and the TCR β chain contain hypervariable regions (CDR, complementarity determining regions), among which the CDR3 region determines the specific epitope recognition. At the C-terminal region both TCR α chain and TCR β chain contain a hydrophobic transmembrane domain and end in a short cytoplasmic tail.

Typically, the TCR is a heterodimer of one α chain and one β chain. This heterodimer can bind to MHC molecules presenting a peptide.

The term "variable TCR α region" or "TCR α variable chain" or "variable domain" in the context of the invention refers to the variable region of a TCR α chain. The term "variable TCR β region" or "TCR β variable chain" in the context of the invention refers to the variable region of a TCR β chain.

The TCR loci and genes are named using the International Immunogenetics (IMGT) TCR nomenclature (IMGT Database, Giudicelli, V., et al., IMGT/LIGM-DB, the IMGT® comprehensive database of immunoglobulin and T cell receptor nucleotide sequences, Nucl. Acids Res., 34, D781-D784 (2006). PMID: 16381979; T cell Receptor Factsbook, LeFranc and LeFranc, Academic Press ISBN 0-12-441352-8).

Target

A first aspect of the invention relates to an isolated TCR specific for one allelic variant of HA-1. This allelic variant is of the single nucleotide polymorphism type.

In particular, the TCR specifically recognizes the amino acid sequence of SEQ ID NO: 2 (VLHDDLLEA).

Typically, the TCR recognizes the peptide fragment of the antigen when it is presented by a major histocompatibility complex (MHC) molecule.

The human leukocyte antigen (HLA) system or complex is a gene complex encoding the major histocompatibility complex (MHC) proteins in humans. HLA-A*02 is one particular class I major histocompatibility complex (MHC) allele group at the HLA-A locus. HLA-A*02:01 is a specific HLA-A*02 suballele.

Thus in a specific embodiment, the TCR specifically recognizes the amino acid sequence of SEQ ID NO: 2, presented by the MHC molecules encoded by the HLA-A*02 alleles, preferably by the HLA-A*02:01 encoded molecule or HLA-A*02:06 encoded molecule, more preferably by the HLA-A02:01 encoded molecule.

The TCR is highly specific for HA-1$^H$ and exhibits substantially not cross-reactivity to other peptides, in particular to the allelic variation HA-1$^R$. That means that it does not recognize the HA-1 allelic variation. In other words, it does not recognize the amino acid sequence of SEQ ID NO: 4. The cross-reactivity may be measured by IFN-γ secretion as described herein.

The term "specific for" in the context of the invention means that the TCR is specifically binding to the target.

The terms "allelic variation" and "allelic version" are used herein are identical.

In preferred embodiments, the recognition motif of the TCR comprises at least the sequence set out in SEQ ID NO: 127. In specific embodiments, the recognition motif of the TCR consists of the sequence set out in SEQ ID NO: 127. Wherein the recognition motif may be determined by serine substitution.

The recognition motif defines the amino acids of the epitope that influence the activation of the TCR, for example determined in an IFN-γ secretion assay. In particular, the influence of an amino acid residue in the binding epitope can be determined by an amino acid substitution scan, such as a serine scan.

In the serine scan, epitope peptides having each individual amino acid residue consecutively substituted by serine are used. If a peptide leads to a significant decrease of TCR activation, e.g. determined by IFN-γ secretion indicates that the substituted position belongs to the recognition motif. A significant decrease may be a decrease of at least 3-fold, preferably at least 5-fold, more preferably of at least 10 fold IFN-γ secretion compared to the unsubstituted peptide sequence, i.e. unsubstituted epitope.

TCR Specific Sequence

The CDR3 of the TCR α chain of the TCR may have the amino acid sequence selected from the group consisting of SEQ ID NO: 7, SEQ ID NO: 17, SEQ ID NO: 27, SEQ ID NO: 37, SEQ ID NO: 47 and SEQ ID NO: 57

The CDR3 of the TCR β chain of the TCR may have the amino acid sequence selected from the group consisting of SEQ ID NO: 10, SEQ ID NO: 20, SEQ ID NO: 30, SEQ ID NO: 40 SEQ ID NO: 50 and SEQ ID NO: 60.

Some embodiments relate to an isolated TCR comprising a TCR α chain and a TCR β chain, wherein
- a)—the TCR α chain comprises a complementarity-determining region 3 (CDR3) having the sequence of SEQ ID NO: 7,
  the TCR β chain comprises a CDR3 having the amino acid sequence of SEQ ID NO: 10; or
- b)—the TCR α chain comprises a CDR3 having the sequence of SEQ ID NO: 17,
  the TCR β chain comprises a CDR3 having the amino acid sequence of SEQ ID NO: 20; or
- c)—the TCR α chain comprises a CDR3 having the sequence of SEQ ID NO: 27,
  the TCR β chain comprises a CDR3 having the amino acid sequence of SEQ ID NO: 30; or
- d)—the TCR α chain comprises a CDR3 having the sequence of SEQ ID NO: 37,
  the TCR β chain comprises a CDR3 having the amino acid sequence of SEQ ID NO: 40; or
- e)—the TCR α chain comprises a CDR3 having the sequence of SEQ ID NO: 47,
  the TCR β chain comprises a CDR3 having the amino acid sequence of SEQ ID NO: 50; or
- f)—the TCR α chain comprises a CDR3 having the sequence of SEQ ID NO: 57,
  the TCR β chain comprises a CDR3 having the amino acid sequence of SEQ ID NO: 60.

More specific embodiments relate to an isolated TCR, wherein the TCR comprises
- a)—a TCR α chain comprising a CDR1 having the amino acid sequence of SEQ ID NO: 5, a CDR 2 having the amino acid sequence of SEQ ID NO: 6 and a CDR 3 having the sequence of SEQ ID NO: 7,
  a TCR β chain comprising a CDR1 having the amino acid sequence of SEQ ID NO: 8, a CDR 2 having the amino acid sequence of SEQ ID NO: 9 and a CDR 3 having the sequence of SEQ ID NO: 10; or
- b)—a TCR α chain comprising a CDR1 having the amino acid sequence of SEQ ID NO: 15, a CDR 2 having the amino acid sequence of SEQ ID NO: 16 and a CDR 3 having the sequence of SEQ ID NO: 17,
  a TCR β chain comprising a CDR 1 having the amino acid sequence of SEQ ID NO: 18, a CDR 2 having the amino acid sequence of SEQ ID NO: 19 and a CDR 3 having the sequence of SEQ ID NO: 20; or
- c)—a TCR α chain comprising a CDR1 having the amino acid sequence of SEQ ID NO: 25, a CDR 2 having the amino acid sequence of SEQ ID NO: 26 and a CDR 3 having the sequence of SEQ ID NO: 27,
  a TCR β chain comprising a CDR 1 having the amino acid sequence of SEQ ID NO: 28, a CDR 2 having the amino acid sequence of SEQ ID NO: 29 and a CDR 3 having the sequence of SEQ ID NO: 30;
- d)—a TCR α chain comprising a CDR1 having the amino acid sequence of SEQ ID NO: 35, a CDR 2 having the amino acid sequence of SEQ ID NO: 36 and a CDR 3 having the sequence of SEQ ID NO: 37,
  a TCR β chain comprising a CDR 1 having the amino acid sequence of SEQ ID NO: 38, a CDR 2 having the amino acid sequence of SEQ ID NO: 39 and a CDR 3 having the sequence of SEQ ID NO: 40; or e)—a TCR α chain comprising a CDR1 having the amino acid sequence of SEQ ID NO: 45, a CDR 2 having the amino acid sequence of SEQ ID NO: 46 and a CDR 3 having the sequence of SEQ ID NO: 47,
a TCR β chain comprising a CDR 1 having the amino acid sequence of SEQ ID NO: 48, a CDR 2 having the amino acid sequence of SEQ ID NO: 49 and a CDR 3 having the sequence of SEQ ID NO: 50; or
f)—a TCR α chain comprising a CDR1 having the amino acid sequence of SEQ ID NO: 55, a CDR 2 having the amino acid sequence of SEQ ID NO: 56 and a CDR 3 having the sequence of SEQ ID NO: 57,
a TCR β chain comprising a CDR1 having the amino acid sequence of SEQ ID NO:58, a CDR 2 having the amino acid sequence of SEQ ID NO: 59 and a CDR 3 having the sequence of SEQ ID NO: 60

Preferred embodiments relate to isolated TCRs which are defined by the CDRs, in particular by the CDR3 of the TCR α and the TCR β chain as described above, wherein the recombinant TCR sequence is modified to contain murinized Cα and Cβ regions.

Some embodiments refer to an isolated TCR, wherein the TCR comprises
a) a variable TCR α region having an amino acid sequence which is at least 80% identical to SEQ ID NO: 11 and a variable TCR β region having an amino acid sequence which is at least 80% identical to SEQ ID NO: 12; or
b) a variable TCR α region having an amino acid sequence which is at least 80% identical to SEQ ID NO: 21 and a variable TCR β region having an amino acid sequence which is at least 80% identical to SEQ ID NO: 22; or
c) a variable TCR α region having an amino acid sequence which is at least 80% identical to SEQ ID NO: 31 and a variable TCR β region having an amino acid sequence which is at least 80% identical to SEQ ID NO: 32; or
d) a variable TCR α region having an amino acid sequence which is at least 80% identical to SEQ ID NO: 41 and a variable TCR β region having an amino acid sequence which is at least 80% identical to SEQ ID NO: 42; or
e) a variable TCR α region having an amino acid sequence which is at least 80% identical to SEQ ID NO: 51 and a variable TCR β region having an amino acid sequence which is at least 80% identical to SEQ ID NO: 52; or
f) a variable TCR α region having an amino acid sequence which is at least 80% identical to SEQ ID NO: 61 and a variable TCR β region having an amino acid sequence which is at least 80% identical to SEQ ID NO: 62.

"At least 80% identical", in particular "having an amino acid sequence which is at least 80% identical" as used herein includes that the amino acid sequence is at least 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence set out.

In some embodiments the TCR comprises a TCR α chain and a TCR β chain, wherein
a)—the variable TCR α region has an amino acid sequence which is at least 80% identical to SEQ ID NO: 11 and comprises a CDR3 region having an amino acid sequence set out in SEQ ID NO: 7,
the variable TCR β region has an amino acid sequence which is at least 80% identical to SEQ ID NO: 12 and comprises a CDR3 region having an amino acid sequence set out SEQ ID NO: 10 or
b)—the variable TCR α region has an amino acid sequence which is at least 80% identical to SEQ ID NO: 21 and comprises a CDR3 region having an amino acid sequence set out in SEQ ID NO: 17,
the variable TCR β region has an amino acid sequence which is at least 80% identical to SEQ ID NO: 22 and comprises a CDR3 region having an amino acid sequence set out SEQ ID NO: 20; or
c)—the variable TCR α region has an amino acid sequence which is at least 80% identical to SEQ ID NO: 31 and comprises a CDR3 region having an amino acid sequence set out in SEQ ID NO: 27;
the variable TCR β region has an amino acid sequence which is at least 80% identical to SEQ ID NO: 32 and comprises a CDR3 region having an amino acid sequence set out SEQ ID NO: 30; or
d)—the variable TCR α region has an amino acid sequence which is at least 80% identical to SEQ ID NO: 41 and comprises a CDR3 region having an amino acid sequence set out in SEQ ID NO: 37;
the variable TCR β region has an amino acid sequence which is at least 80% identical to SEQ ID NO: 42 and comprises a CDR3 region having an amino acid sequence set out SEQ ID NO: 40; or
e)—the variable TCR α region has an amino acid sequence which is at least 80% identical to SEQ ID NO: 51 and comprises a CDR3 region having an amino acid sequence set out in SEQ ID NO: 47;
the variable TCR β region has an amino acid sequence which is at least 80% identical to SEQ ID NO: 52 and comprises a CDR3 region having an amino acid sequence set out SEQ ID NO: 50; or
f)—the variable TCR α region has an amino acid sequence which is at least 80% identical to SEQ ID NO: 61 and comprises a CDR3 region having an amino acid sequence set out in SEQ ID NO: 57;
the variable TCR β region has an amino acid sequence which is at least 80% identical to SEQ ID NO: 62 and comprises a CDR3 region having an amino acid sequence set out SEQ ID NO: 60.

Exemplary embodiments refer to an isolated TCR, wherein the TCR comprises
a) a variable TCR α region having the amino acid sequence of SEQ ID NO: 11 and a variable TCR β region having the amino acid sequence of SEQ ID NO: 12; or
b) a variable TCR α region having the amino acid sequence of SEQ ID NO: 21 and a variable TCR β region having the amino acid sequence of SEQ ID NO: 22; or
c) a variable TCR α region having the amino acid sequence of SEQ ID NO: 31 and a variable TCR β region having the amino acid sequence of SEQ ID NO: 32; or
d) a variable TCR α region having the amino acid sequence of SEQ ID NO: 41 and a variable TCR β region having the amino acid sequence of SEQ ID NO: 42; or
e) a variable TCR α region having the amino acid sequence of SEQ ID NO: 51 and a variable TCR β region having the amino acid sequence of SEQ ID NO: 52; or f) a variable TCR α region having the amino acid sequence of SEQ ID NO: 61 and a variable TCR β region having the amino acid sequence of SEQ ID NO: 62.

The following table shows a summary of the exemplary TCRs of the invention

TABLE 1

Summary of exemplary TCRs of the invention

| TCR | CDR1_alpha | CDR2_alpha | CDR3_alpha | TRAV | TRAJ | CDR1_beta | CDR2_beta | CDR3_beta | TRBV | TRBJ |
|---|---|---|---|---|---|---|---|---|---|---|
| 1 | DSASNY (SEQ ID NO: 5) | IRSNVGE (SEQ ID NO: 6) | CAASDLNF (SEQ ID NO: 7) | 13-1 | 41 | SEHNR (SEQ ID NO: 8) | FQNEAQ (SEQ ID NO: 9) | CASSLVSRVDGYTF (SEQ ID NO: 10) | 7-9 | 1-2 |
| 2 | DSASNY (SEQ ID NO: 5) | IRSNVGE (SEQ ID NO: 6) | CAAHTPGYSTLTF (SEQ ID NO: 17) | 13-1 | 11 | SEHNR (SEQ ID NO: 8) | FQNEAQ (SEQ ID NO: 9) | CASSPRAGGETQYF (SEQ ID NO: 20) | 7-9 | 2-5 |
| 3 | TSINN (SEQ ID NO: 25) | IRSNERE (SEQ ID NO: 26) | CATGDQTGANNLFF (SEQ ID NO: 27) | 17 | 36 | SEHNR (SEQ ID NO: 8) | FQNEAQ (SEQ ID NO: 9) | CASSLTRTEKLFF (SEQ ID NO: 30) | 7-9 | 1-4 |
| 4 | DSASNY (SEQ ID NO: 5) | IRSNVGE (SEQ ID NO: 6) | CAGRGKLTF (SEQ ID NO: 37) | 13-1 | 48 | SEHNR (SEQ ID NO: 8) | FQNEAQ (SEQ ID NO: 9) | CASSLVRDEKLFF (SEQ ID NO: 40) | 7-9 | 1-4 |
| 5 | SVFSS (SEQ ID NO: 45) | VVTGGEV (SEQ ID NO: 46) | CAGAGNNDMRF (SEQ ID NO: 47) | 27 | 43 | SEHNR (SEQ ID NO: 8) | FQNEAQ (SEQ ID NO: 9) | CASSLVRGIEAFF (SEQ ID NO: 50) | 7-9 | 1-1 |
| 6 | DSSSTY (SEQ ID NO: 55) | IFSNMDM (SEQ ID NO: 56) | CAEKWIIF (SEQ ID NO: 57) | 5 | 30 | SEHNR (SEQ ID NO: 8) | FQNEAQ (SEQ ID NO: 9) | CASSLTTPDGYTF (SEQ ID NO: 60) | 7-9 | 1-2 |

As can be seen from the examples the TCRs according to the invention are specific for HA-1$^H$ and exhibit only very low cross-reactivity to other epitopes or antigens.

The determination of percent identity between multiple sequences is preferably accomplished using the AlignX application of the Vector NTI Advance™ 10 program (Invitrogen Corporation, Carlsbad CA, USA). This program uses a modified Clustal W algorithm (Thompson et al., 1994. Nucl Acids Res. 22: pp. 4673-4680; Invitrogen Corporation; Vector NTI Advance™ 10 DNA and protein sequence analysis software. User's Manual, 2004, pp. 389-662). The determination of percent identity is performed with the standard parameters of the AlignX application.

The TCR according to the invention is isolated or purified. "Isolated" in the context of the invention means that the TCR is not present in the context in which it originally occurred in nature. "Purified" in the context of the invention means e.g. that the TCR is free or substantially free of other proteins and non-protein parts of the cell it originally stems from.

In some embodiments, the amino acid sequence of the TCR may comprise one or more phenotypically silent substitutions.

"Phenotypically silent substitutions" are also named "conservative amino acid substitutions". The concept of "conservative amino acid substitutions" is understood by the skilled artisan, and preferably means that codons encoding positively-charged residues (H, K, and R) are substituted with codons encoding positively-charged residues, codons encoding negatively-charged residues (D and E) are substituted with codons encoding negatively-charged residues, codons encoding neutral polar residues (C, G, N, Q, S, T, and Y) are substituted with codons encoding neutral polar residues, and codons encoding neutral non-polar residues (A, F, I, L, M, P, V, and W) are substituted with codons encoding neutral non-polar residues. These variations can spontaneously occur, be introduced by random mutagenesis, or can be introduced by directed mutagenesis. Those changes can be made without destroying the essential characteristics of these polypeptides. The ordinarily skilled artisan can readily and routinely screen variant amino acids and/or the nucleic acids encoding them to determine if these variations substantially reduce or destroy the ligand binding capacity by methods known in the art.

The skilled person understands, that also the nucleic acid encoding the TCR may be modified. Useful modifications in the overall nucleic acid sequence include codon optimization of the sequence. Alterations may be made which lead to conservative substitutions within the expressed amino acid sequence. These variations can be made in complementarity determining and non-complementarity determining regions of the amino acid sequence of the TCR chain that do not affect function. Usually, additions and deletions should not be performed in the CDR3 region.

According to some embodiments of the invention the amino acid sequence of the TCR is modified to comprise a detectable label, a therapeutic agent or pharmacokinetic modifying moiety.

Non-limiting examples for detectable labels are radiolabels, fluorescent labels, nucleic acid probes, enzymes and contrast reagents. Therapeutic agents which may be associated with the TCRs include radioactive compounds, immunomodulators, enzymes or chemotherapeutic agents. The therapeutic agents could be enclosed by a liposome linked to TCR so that the compound can be released slowly at the target site. This will avoid damaging during the transport in the body and ensure that the therapeutic agent, e.g. toxin, has maximum effect after binding of the TCR to the relevant antigen presenting cells. Other examples for therapeutic agents are:

Peptide cytotoxins, i.e. proteins or peptides with the ability to kill mammalian cells, such as ricin, diphtheria toxin, pseudomonas bacterial exotoxin A, DNase and RNase. Small molecule cytotoxic agents, i.e. compounds with the ability to kill mammalian cells having a molecular weight of less than 700 Daltons. Such compounds could contain toxic metals capable of having a cytotoxic effect. Furthermore, it is to be understood that these small molecule cytotoxic agents also include pro-drugs, i.e. compounds that decay or are converted under physiological conditions to release cytotoxic agents. Such agents may for example include docetaxel, gemcitabine, cis-platin, maytansine derivatives, rachelmycin, calicheamicin, ctoposide, ifosfamide, irinotecan, porfimer sodium photofrin II, temozolomide, topotecan, trimetrexate glucoronate, mitoxantrone, auristatin E, vincristine and doxorubicin; radionuclides, such as, iodine 131, rhenium 186, indium 111, yttrium 90, bismuth 210 and 213, actinium 225 and astatine 213. The association of the radionuclides with the TCRs or derivatives thereof may for example be carried out by chelating agents; immunostimulators, also known as immunostimulants, i.e. immune effector molecules which stimulate immune response. Exemplary immunstimulators are cytokines such as IL-2 and IFN-γ, antibodies or fragments thereof, including anti-T cell or NK cell determinant antibodies (e.g anti-CD3, anti-CD28 or anti-CD16); alternative protein scaffolds with antibody like binding characteristics; Superantigens, i.e. antigens that cause non-specific activation of T cells resulting in polyclonal T cell activation and massive cytokine release, and mutants thereof; chemokines such as IL-8, platelet factor 4, melanoma growth stimulatory protein, etc. complement activators; xenogeneic protein domains, allogeneic protein domains, viral/bacterial protein domains, viral/bacterial peptides.

The antigen receptor molecules (T cell receptor molecules) on human T lymphocytes are non-covalently associated with the CD3 (T3) molecular complex on the cell surface. Perturbation of this complex with anti-CD3 monoclonal antibodies induces T cell activation. Thus, some embodiments refer to a TCR as described herein associated (usually by fusion to an N- or C-terminus of the alpha or beta chain) with an anti-CD3 antibody, or a functional fragment or variant of said anti-CD3 antibody. Antibody fragments and variants/analogues which are suitable for use in the compositions and methods described herein include minibodies, Fab fragments, F(ab<'>)2fragments, dsFv and scFv fragments, Nanobodies™ (Ablynx (Belgium), molecules comprising synthetic single immunoglobulin variable heavy chain domain derived from a camelid (e.g. camel or llama) antibody) and Domain Antibodies (comprising an affinity matured single immunoglobulin variable heavy chain domain or immunoglobulin variable light chain domain (Domantis (Belgium)) or alternative protein scaffolds that exhibit antibody-like binding characteristics such as Affibodies (comprising engineered protein A scaffold Affibody (Sweden)) or Anticalins (comprising engineered anticalins Pieris (Germany)).

The therapeutic agent may preferably be selected from the group consisting of an immune effector molecule, a cytotoxic agent and a radionuclide. Preferably, the immune effector molecule is a cytokine.

The pharmacokinetic modifying moiety may be for example at least one polyethylene glycol repeating unit, at least one glycol group, at least one sialyl group or a combination thereof. The association of at least one polyethylene glycol repeating unit, at least one glycol group, at least one sialyl group may be caused in a number of ways known to those skilled in the art. In a preferred embodiment the units are covalently linked to the TCR. The TCRs according to the invention can be modified by one or several pharmacokinetic modifying moieties. In particular, the soluble form of the TCR is modified by one or several pharmacokinetic modifying moieties. The pharmacokinetic modifying moiety may achieve beneficial changes to the pharamacokinetic profile of the therapeutic, for example improved plasma half-life, reduced or enhanced immunogenicity, and improved solubility.

The TCR according to the invention may be soluble or membrane bound. The term "soluble" refers to a TCR being in soluble form (i.e. having no transmembrane or cytoplasmic domains), for example for use as a targeting agent for delivering therapeutic agents to the antigen presenting cell. For stability, soluble αβ heterodimeric TCRs preferably have an introduced disulfide bond between residues of the respective constant domains, as described, for example, in WO 03/020763. One or both of the constant domains present in an αβ heterodimer of the invention may be truncated at the C terminus or C termini, for example by up to 15, or up to 10 or up to 8 or fewer amino acids. For use in adoptive therapy, an αβ heterodimeric TCR may, for example, be transfected as full-length chains having both cytoplasmic and transmembrane domains. TCRs may contain a disulfide bond corresponding to that found in nature between the respective alpha and beta constant domains, additionally or alternatively a non-native disulfide bond may be present.

The TCR, in particular a soluble form of the TCR according to the invention can thus be modified by attaching additional functional moieties, e.g. for reducing immunogenicity, increasing hydrodynamic size (size in solution) solubility and/or stability (e.g. by enhanced protection to proteolytic degradation) and/or extending serum half-life.

Other useful functional moieties and modifications include "suicide" or "safety switches" that can be used to shut off effector host cells carrying an inventive TCR in a patient's body. An example is the inducible Caspase 9 (iCasp9) "safety switch" described by Gargett and Brown Front Pharmacol. 2014; 5:235. Briefly, effector host cells are modified by well-known methods to express a Caspase 9 domain whose dimerization depends on a small molecule dimerizer drug such as AP1903/CIP, and results in rapid induction of apoptosis in the modified effector cells. The system is for instance described in EP2173869 (A2). Examples for other "suicide" "safety switches" are known in the art, e.g. Herpes Simplex Virus thymidine kinase (HSV-TK), expression of CD20 and subsequent depletion using anti-CD20 antibody, expression of truncated EGFR and subsequent depletion using anti-EGFR antibody (Wang et al, Blood, 2011 Aug. 4; 118 (5): 1255-63) or myc tags (Kieback et al, Proc Natl Acad Sci USA. 2008 Jan. 15; 105 (2): 623-8).

TCRs with an altered glycosylation pattern are also envisaged herein. As is known in the art, glycosylation patterns can depend on the amino acid sequence (e.g., the presence or absence of particular glycosylation amino acid residues, discussed below) and/or the host cell or organism in which the protein is produced. Glycosylation of polypeptides is typically either N-linked or O-linked. N-linked refers to the attachment of the carbohydrate moiety to the side chain of an asparagine residue. Addition of N-linked glycosylation sites to the binding molecule is conveniently accomplished by altering the amino acid sequence such that it contains one or more tri-peptide sequences selected from asparagine-X-serine and asparagine-X-threonine (where X is any amino acid except proline). O-linked glycosylation sites may be introduced by the addition of or substitution by, one or more serine or threonine residues to the starting sequence.

Another means of glycosylation of TCRs is by chemical or enzymatic coupling of glycosides to the protein. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. Similarly, deglycosylation (i.e., removal of carbohydrate moieties present on the binding molecule) may be accomplished chemically, e.g. by exposing the TCRs to trifluoromethanesulfonic acid, or enzymatically by employing endo- and exo-glycosidases.

It is also conceivable to add a drug such as a small molecule compound to the TCR, in particular a soluble form of the inventive TCR. Linkage can be achieved via covalent bonds, or non-covalent interactions such as through electrostatic forces. Various linkers, known in the art, can be employed in order to form the drug conjugates.

The TCR, in particular a soluble form of the inventive TCR can additionally be modified to introduce additional domains which aid in identification, tracking, purification and/or isolation of the respective molecule (tags). Thus in some embodiments, the TCR α chain or the TCR β chain may be modified to comprise an epitope tag.

Epitope tags are useful examples of tags that can be incorporated into the TCR of the invention. Epitope tags are short stretches of amino acids that allow for binding of a specific antibody and therefore enable identification and tracking of the binding and movement of soluble TCRs or host cells within the patient's body or cultivated (host) cells. Detection of the epitope tag, and hence, the tagged TCR, can be achieved using a number of different techniques.

Tags can further be employed for stimulation and expansion of host cells carrying an inventive TCR by cultivating the cells in the presence of binding molecules (antibodies) specific for said tag.

In general, the TCR can be modified in some instances with various mutations that modify the affinity and the off-rate of the TCR with the target antigen. In particular, the mutations may increase the affinity and/or reduce the off-rate. Thus, the TCR may be mutated in at least one CDR and the variable domain framework region thereof.

However, in a preferred embodiment the CDR regions of the TCR are not modified or in vitro affinity maturated such as for the TCR receptors in the examples. This means that the CDR regions have naturally occurring sequences. This can be advantageous, since in vitro affinity maturation may lead to immunogenicity to the TCR molecule. This may lead to the production of anti-drug antibodies decreasing or inactivating the therapeutic effect and the treatment and/or induce adverse effects.

The mutation may be one or more substitution(s), deletion(s) or insertions(s). These mutations may be introduced by any suitable method known in the art, such as polymerase chain reaction, restriction enzyme based cloning, ligation independent cloning procedures, which are described for Example in Sambrook, Molecular Cloning-4th Edition (2012) Cold Spring Harbor Laboratory Press.

Theoretically, unpredictable TCR specificity with the risk for cross-reactivity can occur due to mispairing between endogenous and exogenous TCR chains. To avoid mispairing of TCR sequences, the recombinant TCR sequence may be modified to contain murinized Cα and Cβ regions, a technology that has been shown to efficiently enhance correct pairing of several different transduced TCR chains. Murinization of TCRs (i.e. exchanging the human constant regions in the alpha and beta chain by their murine counterparts) is a technique that is commonly applied in order to improve cell surface expression of TCRs in host cells. Without wishing to be bound by specific theory, it is thought that murinized TCRs associate more effectively with CD3 co-receptors; and/or that preferentially pair with each other and are less prone to form mixed TCRs on human T cells genetically modified ex vivo to express the TCRs of desired antigenic specificity, but still retaining and expressing their "original", i.e. endogenous, TCRs. Nine amino acids responsible for the improved expression of murinized TCRs have been identified (Sommermeyer and Uckert, J Immunol. 2010 Jun. 1; 184 (11): 6223-31) and it is envisaged to substitute at least one or all of the amino acid residues in the TCRs alpha and/or beta chain constant region for their murine counterpart residues. This technique is also referred to as "minimal murinization", and offers the advantage of enhancing cell surface expression while, at the same time, reducing the number of "foreign" amino acid residues in the amino acid sequence and, thereby, the risk of immunogenicity. Thus, in some embodiments the TCR sequence may be modified to contain minimal murinized Cα and Cβ regions.

Some embodiments refer to an isolated TCR as described herein, wherein the TCR is of the single chain type, wherein the TCR α chain and the TCR β chain are linked by a linker sequence.

A suitable single chain TCR form comprises a first segment constituted by an amino acid sequence corresponding to a variable TCR α region, a second segment constituted by an amino acid sequence corresponding to a variable TCR β region fused to the N terminus of an amino acid sequence corresponding to a TCR β chain constant region extracellular sequence, and a linker sequence linking the C terminus of the first segment to the N terminus of the second segment. Alternatively, the first segment may be constituted by an amino acid sequence corresponding to a TCR β chain variable region, the second segment may be constituted by an amino acid sequence corresponding to a TCR α chain variable region sequence fused to the N terminus of an amino acid sequence corresponding to a TCR α chain constant region extracellular sequence. The above single chain TCRs may further comprise a disulfide bond between the first and second chains, and wherein the length of the linker sequence and the position of the disulfide bond being such that the variable domain sequences of the first and second segments are mutually orientated substantially as in native TCRs. More specifically the first segment may be constituted by an amino acid sequence corresponding to a TCR α chain variable region sequence fused to the N terminus of an amino acid sequence corresponding to a TCR α chain constant region extracellular sequence, the second segment may be constituted by an amino acid sequence corresponding to a TCR β chain variable region fused to the N terminus of an amino acid sequence corresponding to TCR β chain constant region extracellular sequence, and a disulfide bond may be provided between the first and second chains. The linker sequence may be any sequence which does not impair the function of the TCR.

In the context of the present invention, a "functional" TCR α and/or β chain fusion protein shall mean a TCR or TCR variant, for example modified by addition, deletion or substitution of amino acids, that maintains at least substantial biological activity. In the case of the a and/or B chain of a TCR, this shall mean that both chains remain able to form a T-cell receptor (either with a non-modified a and/or β chain or with another inventive fusion protein a and/or β chain) which exerts its biological function, in particular binding to the specific peptide-MHC complex of said TCR, and/or functional signal transduction upon specific peptide:MHC interaction.

In specific embodiments the TCR may be modified, to be a functional TCR α and/or β chain fusion protein, wherein said epitope-tag has a length of between 6 to 15 amino acids, preferably 9 to 11 amino acids. In another embodiment the TCR may be modified to be a functional TCR α and/or β chain fusion protein wherein said TCR α and/or β chain fusion protein comprises two or more epitope-tags, either spaced apart or directly in tandem. Embodiments of the fusion protein can contain 2, 3, 4, 5 or even more epitope-tags, as long as the fusion protein maintains its biological activity/activities ("functional").

Preferred is a functional TCR α and/or β chain fusion protein according to the present invention, wherein said epitope-tag is selected from, but not limited to, CD20 or Her2/neu tags, or other conventional tags such as a myc-tag, FLAG-tag, T7-tag, HA (hemagglutinin)-tag, His-tag, S-tag, GST-tag, or GFP-tag, myc, T7, GST, GFP tags are epitopes derived from existing molecules. In contrast, FLAG is a synthetic epitope tag designed for high antigenicity (scc, e.g., U.S. Pat. Nos. 4,703,004 and 4,851,341). The myc tag can preferably be used because high quality reagents are available to be used for its detection. Epitope tags can of course have one or more additional functions, beyond recognition by an antibody. The sequences of these tags are described in the literature and well known to the person of skill in art.

TCR Fragments and Variants

Another aspect of the invention refers to a polypeptide comprising a functional portion of the TCR of as described herein. The functional portion may comprise at least one of the amino acid sequences selected from the group consisting of SEQ ID NOs: SEQ ID NO: 7, SEQ ID NO: 17, SEQ ID NO: 27, SEQ ID NO: 37, SEQ ID NO: 47 SEQ ID NO: 57, SEQ ID NO: 10, SEQ ID NO: 20, SEQ ID NO: 30, SEQ ID NO: 40 SEQ ID NO: 50 and SEQ ID NO: 60.

In specific embodiments the polypeptide may be the functional portion of the TCR alone, e.g. in a soluble form. Alternatively, the polypeptide may be combined with other domains.

The functional portion may mediate the binding of the TCR to the antigen, in particular to the antigen-MHC complex.

In one embodiment, the functional portion comprises the TCR α variable chain and/or the TCR β variable chain as described herein.

The TCR variant molecule, i.e. a molecule combining a polypeptide comprising a functional portion of the TCR with other domains, may have the binding properties of the TCR receptor but may be combined with signaling domains of effectors cells (other than T cells), in particular with signaling domains of NK cells. Therefore, some embodiments refer to a protein comprising a functional portion of the TCR as described herein in combination with the signaling domains of an effector cell, such as a NK cell.

"Binding" refers to the ability to specifically and non-covalently associate, unite or bind with the target.

Another aspect of the invention refers to a multivalent TCR complex comprising at least two TCRs as described herein. In one embodiment of this aspect, at least two TCR molecules are linked via linker moieties to form multivalent complexes. Preferably, the complexes are water soluble, so the linker moiety should be selected accordingly. It is preferable that the linker moiety is capable of attaching to defined positions on the TCR molecules, so that the structural diversity of the complexes formed is minimized. One embodiment of the present aspect is provided by a TCR complex of the invention wherein the polymer chain or peptidic linker sequence extends between amino acid residues of each TCR which are not located in a variable region sequence of the TCR. Since the complexes of the invention may be for use in medicine, the linker moieties should be chosen with due regard to their pharmaceutical suitability, for example their immunogenicity. Examples of linker moieties which fulfil the above desirable criteria are known in the art, for example the art of linking antibody fragments.

Examples for linkers are hydrophilic polymers and peptide linkers. An example for hydrophilic polymers are polyalkylene glycols. The most commonly used of this class are based on polyethylene glycol or PEG. However, others are based on other suitable, optionally substituted, polyalkylene glycols which include polypropylene glycol, and copolymers of ethylene glycol and propylene glycol. Peptide linkers are comprised of chains of amino acids, and function to produce simple linkers or multimerization domains onto which TCR molecules can be attached.

One embodiment refers to a multivalent TCR complex, wherein at least one of said TCRs is associated with a therapeutic agent.

Cytokine and Chemokine Release

Some embodiments refer to the isolated TCR as described herein, polypeptide as described herein, multivalent TCR complex as described herein, wherein IFN-γ secretion is induced by binding of the inventive TCR expressed on an effector cell to the amino acid sequence of SEQ ID NO: 2, which is presented by the HLA-A*02:01 encoded molecule.

The IFN-γ secretion induced by binding of the inventive TCR expressed on an effector cell to the amino acid sequence of SEQ ID NO: 2, which is presented by the HLA-A*02:01 encoded molecule, may be at least 3 times higher, preferably at least 10 times higher, more preferably at least 20 times higher, even more preferably at least 50 times higher, most preferably at least 100 times higher when binding to the amino acid sequence of SEQ ID NO: 2, which is presented by the HLA-A*02:01 encoded molecule, compared to binding to SEQ ID NO: 4, which is presented by the HLA-A*02:01 encoded molecule, at a HA-1 peptide concentration of $10^{-7}$ [M].

The IFN-γ secretion induced by binding of the inventive TCR expressed on an effector cell to the amino acid sequence of SEQ ID NO: 2, which is presented by the HLA-A*02:01 encoded molecule, may be at least 3 times higher, preferably at least 10 times higher, more preferably at least 20 times higher, even more preferably at least 50 times higher, most preferably at least 100 times higher when binding to the amino acid sequence of SEQ ID NO: 2, which is presented by the HLA-A*02:01 encoded molecule, compared to binding to SEQ ID NO: 4, which is presented by the HLA-A*02:01 encoded molecule, at a HA-1 peptide concentration of $10^{-6}$ [M].

The IFN-γ secretion induced by binding of the inventive TCR expressed on an effector cell to the amino acid sequence of SEQ ID NO: 2, which is presented by the HLA-A*02:01 encoded molecule, may be at least 3 times higher, such as 10 times higher, preferably at least 10 times higher, such as at least 20 times higher, at least 50 times higher, at least 100 times higher when binding to the amino acid sequence of SEQ ID NO: 2, which is presented by the HLA-A*02:01 encoded molecule, compared to binding to SEQ ID NO: 4, which is presented by the HLA-A*02:01 encoded molecule, at a HA-1 peptide concentration of 105 [M].

Thus, for recognition of the HA-1$^R$-variant at least 1,000, preferred at least 5,000, more preferred at least 8,000, most preferred at least 10,0000 times higher peptide concentrations compared to HA-1$^H$ are needed for all of the HA-1$^H$-TCR-transgenic T cells.

In specific embodiments, for example when the ratio of TCR-transgenic T cells to T2 cells is 2:1, the IFN-γ secretion induced by binding of the inventive TCR expressed on an effector cell to the amino acid sequence of SEQ ID NO: 2, which is presented by the HLA-A*02:01 encoded molecule, may be more than 500 pg/ml, such as more than 1000 pg/ml, more preferably more than 2000 pg/ml, most preferably more than 3000 pg/ml at a HA-1 peptide concentration of $10^{-7}$ [M].

The "effector cell" may be a peripheral blood lymphocyte (PBL) or a peripheral blood mononuclear cell (PBMC). Typically, the effector cell is an immune effector cell, especially a T cell. Other suitable cell types include gamma-delta T cells and NK-like T cells.

The invention relates also to methods for identifying a TCR or a fragment thereof that binds to the target amino acid sequence of SEQ ID NO: 2 or the HLA-A2 bound form thereof, preferably to SEQ ID NO: 2, which is presented by the HLA-A*02:01 encoded molecule or HLA-A*02:06 encoded molecule, preferably by the HLA-A*02:01 encoded molecule or HLA-A*02:06 encoded molecule wherein the method comprises contacting the candidate TCR or fragment thereof with the amino acid sequence SEQ ID NO: 2 or the HLA-A02 bound form thereof, preferably to SEQ ID NO: 2, which is presented by the HLA-A*02:01 encoded molecule or HLA-A*02:06 encoded molecule, preferably by the HLA-A*02:01 encoded molecule, and determining whether the candidate TCR or fragment thereof binds to the target and/or mediates an immune response.

Whether the candidate TCR or fragment thereof mediates an immune response can be determined for example by the measurement of cytokine secretion, such as IFN-γ secretion. As described above cytokine secretion may be measured by an in vitro assay in which K562 cells (or other APCs) transfected with ivtRNA coding the amino acid sequence SEQ ID NO: 2, are incubated with CD8+ enriched PBMC expressing the TCR or a molecule comprising a fragment of the TCR to be investigated.

Nucleic Acids, Vectors

Another aspect of the invention refers to a nucleic acid encoding a TCR as described herein or encoding the polynucleotide encoding a TCR as described herein.

The following table indicates the nucleotide sequences encoding the respective peptide sequences:

| peptide sequence SEQ ID NO | nucleotide sequence SEQ ID NO | description |
| --- | --- | --- |
| 5 | 66 | TCR_1 α chain CDR1 |
| 6 | 67 | TCR_1 α chain CDR2 |
| 7 | 68 | TCR_1 α chain CDR3 |
| 8 | 69 | TCR_1 β chain CDR1 |
| 9 | 70 | TCR_1 β chain CDR2 |
| 10 | 71 | TCR_1 β chain CDR3 |
| 11 | 72 | TCR_1 α chain variable region |
| 12 | 73 | TCR_1 β chain variable region |
| 13 | 74 | TCR_1 α chain complete |
| 14 | 75 | TCR_1 β chain complete |
| 15 | 76 | TCR_2 α chain CDR1 |
| 16 | 77 | TCR_2 α chain CDR2 |
| 17 | 78 | TCR_2 α chain CDR3 |
| 18 | 79 | TCR_2 β chain CDR1 |
| 19 | 80 | TCR_2 β chain CDR2 |
| 20 | 81 | TCR_2 β chain CDR3 |
| 21 | 82 | TCR_2 α chain variable region |
| 22 | 83 | TCR_2 β chain variable region |
| 23 | 84 | TCR_2 α chain complete |
| 24 | 85 | TCR_2 β chain complete |
| 25 | 86 | TCR_3 α chain CDR1 |
| 26 | 87 | TCR_3 α chain CDR2 |
| 27 | 88 | TCR_3 α chain CDR3 |
| 28 | 89 | TCR_3 β chain CDR1 |
| 29 | 90 | TCR_3 β chain CDR2 |
| 30 | 91 | TCR_3 β chain CDR3 |
| 31 | 92 | TCR_3 α chain variable region |
| 32 | 93 | TCR_3 β chain variable region |
| 33 | 94 | TCR_3 α chain complete |
| 34 | 95 | TCR_3 β chain complete |
| 35 | 96 | TCR_4 α chain CDR1 |
| 36 | 97 | TCR_4 α chain CDR2 |
| 37 | 98 | TCR_4 α chain CDR3 |
| 38 | 99 | TCR_4 β chain CDR1 |
| 39 | 100 | TCR_4 β chain CDR2 |
| 40 | 101 | TCR_4 β chain CDR3 |
| 41 | 102 | TCR_4 α chain variable |
| 42 | 103 | TCR_4 β chain variable |
| 43 | 104 | TCR_4 α chain complete |
| 44 | 105 | TCR_4 β chain complete |
| 45 | 106 | TCR_5 α chain CDR1 |
| 46 | 107 | TCR_5 α chain CDR2 |
| 47 | 108 | TCR_5 α chain CDR3 |
| 48 | 109 | TCR_5 β chain CDR1 |
| 49 | 110 | TCR_5 β chain CDR2 |
| 50 | 111 | TCR_5 β chain CDR3 |
| 51 | 112 | TCR_5 a variable region |
| 52 | 113 | TCR_5 β chain variable region |
| 53 | 114 | TCR_5 α chain complete |
| 54 | 115 | TCR_5 β chain complete |
| 55 | 116 | TCR_6 α chain CDR1 |
| 56 | 117 | TCR_6 α chain CDR2 |
| 57 | 118 | TCR_6 α chain CDR3 |
| 58 | 119 | TCR_6 β chain CDR1 |
| 59 | 120 | TCR_6 β chain CDR2 |
| 60 | 121 | TCR_6 β chain CDR3 |
| 61 | 122 | TCR_6 α chain variable |
| 62 | 123 | TCR_6 β chain variable region |
| 63 | 124 | TCR_6 α chain complete |
| 64 | 125 | TCR_6 β chain complete |

"Nucleic acid molecule" and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. Preferably, the nucleic acids described herein are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication. The nucleic acids can be constructed based on chemical synthesis and/or enzymatic ligation reactions using procedures known in the art or commercially available (e.g. from Genscript, Thermo Fisher and similar companies). See, for example Sambrook et al., a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). The nucleic acid can comprise any nucleotide sequence which encodes any of the recombinant TCRs, polypeptides, or proteins, or functional portions or functional variants thereof.

The present disclosure also provides variants of the isolated or purified nucleic acids wherein the variant nucleic acids comprise a nucleotide sequence that has at least 75%, 80%, 81%, 82%, 83%, 84%, 85%, 86%, 87%, 88%, 89%, 90%, 91%, 92%, 93%, 94%, 95%, 96%, 97%, 98%, or 99% identical to the nucleotide sequence encoding the TCR described herein. Such variant nucleotide sequence encodes a functional TCR that specifically recognizes HA-1" antigen.

The disclosure also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the TCRs described herein. It is generally appreciated that conditions can be rendered more stringent by the addition of increasing amounts of formamide.

As already described elsewhere herein, the nucleic acid encoding the TCR may be modified. Useful modifications in the overall nucleic acid sequence may be codon optimization. Alterations may be made which lead to conservative substitutions within the expressed amino acid sequence. These variations can be made in complementarity determining and non-complementarity determining regions of the amino acid sequence of the TCR chain that do not affect function. Usually, additions and deletions should not be performed in the CDR3 region. Another embodiment refers to a vector comprising the nucleic acid encoding the TCR as described herein.

The vector is preferably a plasmid, shuttle vector, phagemide, cosmid, expression vector, retroviral vector, adenoviral vector or particle and/or vector to be used in gene therapy.

A "vector" is any molecule or composition that has the ability to carry a nucleic acid sequence into a suitable host cell where synthesis of the encoded polypeptide can take place. Typically, and preferably, a vector is a nucleic acid that has been engineered, using recombinant DNA techniques that are known in the art, to incorporate a desired nucleic acid sequence (e.g. a nucleic acid of the invention). The vector may comprise DNA or RNA and/or comprise liposomes. The vector may be a plasmid, shuttle vector, phagemide, cosmid, expression vector, retroviral vector, lentiviral vector, adenoviral vector or particle and/or vector to be used in gene therapy. A vector may include nucleic acid sequences that permit it to replicate in a host cell, such as an origin of replication. A vector may also include one or more selectable marker genes and other genetic elements known to those of ordinary skill in the art. A vector preferably is an expression vector that includes a nucleic acid according to the present invention operably linked to sequences allowing for the expression of said nucleic acid.

Preferably, the vector is an expression vector. More preferably, the vector is a retroviral, more specifically a gamma-retroviral or lentiviral vector.

Cells, Cell Lines

Another aspect of the invention refers to a cell expressing the TCR as described herein.

In some embodiments, the cell is isolated or non-naturally occurring.

In specific embodiments, the cell may comprise the nucleic acid encoding the TCR as described herein or the vector comprising said nucleic acid.

In the cell the above described vector comprising a nucleic acid sequence coding for the above described TCR may be introduced or ivtRNA coding for said TCR may be introduced. The cell may be a peripheral blood lymphocyte such as a T cell. The method of cloning and exogenous expression of the TCR is for example described in Engels et al. (Relapse or eradication of cancer is predicted by peptide-major histocompatibility complex affinity. Cancer Cell, 23 (4), 516-26. 2013). The transduction of primary human T cells with a lentiviral vector is, for example, described in Cribbs "simplified production and concentration of lentiviral vectors to achieve high transduction in primary human T cells" BMC Biotechnol. 2013; 13:98.

The term "transfection" and "transduction" are interchangeable and refer to the process by which an exogenous nucleic acid sequence is introduced in a host cell, e.g. in a eukaryotic host cell. It is noted that introduction or transfer of nucleic acid sequences is not limited to the mentioned methods but can be achieved by any number of means including electroporation, microinjection, gene gun delivery, lipofection, superfection and the mentioned infection by retroviruses or other suitable viruses for transduction or transfection.

Some embodiments refer to a cell comprising:
a) an expression vector which comprises at least one nucleic acid as described herein, or
b) a first expression vector which comprises a nucleic acid encoding the alpha chain of the TCR as described herein, and a second expression vector which comprises a nucleic acid encoding the beta chain of a TCR as described herein.

In some embodiments, the cell is a peripheral blood lymphocyte (PBL) or a peripheral blood mononuclear cell (PBMC). The cell may be a natural killer cell or a T cell. Preferably, the cell is a T cell. The T cell may be a CD4+ or a CD8+ T cell.

In some embodiments the cell is a stem cell like memory T cell.

Stem cell-like memory T cells (TSCM) are a less-differentiated subpopulation of CD8+ T cells, which are characterized by the capacity of self-renewal and to persist long-term. Once these cells encounter their antigen in vivo, they differentiate further into central memory T cells (TCM), effector memory T cells (TEM) and terminally differentiated effector memory T cells (TEMRA) with some TSCM remaining quiescent (Flynn et al., Clinical & Translational Immunology (2014). These remaining TSCM cells show the capacity to build a durable immunological memory in vivo and therefore are considered an important T cell subpopulation for adoptive T cell therapy (Lugli et al., Nature Protocols 8, 33-42 (2013) Gattinoni et al., Nat. Med. 2011 October; 17 (10): 1290-1297). Immune-magnetic selection can be used in order to restrict the T cell pool to the stem cell memory T cell subtype see (Riddell et al. 2014, Cancer Journal 20 (2): 141-44)

Antibodies Targeting TCR

Another aspect of the invention refers to an antibody or antigen binding fragment thereof specifically binding to a portion of the TCR as described herein that mediates specificity for HA-1$^H$. In one embodiment, the portion of the TCR that mediates the HA-1$^H$ specificity comprises the CDR3 of the alpha chain of SEQ ID NO: 7, SEQ ID NO: 17, SEQ ID NO: 27. SEQ ID NO: 37, SEQ ID NO: 47 and SEQ ID NO: 57 and/or the CDR3 of the beta chain of SEQ ID NO: 10, SEQ ID NO: 20, SEQ ID NO: 30, SEQ ID NO: 40 SEQ ID NO: 50 and SEQ ID NO: 60.

The antibody or antigen binding fragment thereof may modulate the activity of the TCR. It may block or may not block the binding of the TCR with HA-1$^H$. It could be used for modulating the therapeutic activity of the TCR or for diagnostic purposes.

Pharmaceutical Compositions, Medical Treatments and Kits

Another aspect of the invention refers to pharmaceutical composition comprising the TCR as described herein, the polypeptide comprising a functional portion of said TCR, the multivalent TCR complex as described herein, the nucleic acid encoding the TCR, the vector comprising said nucleic acid, the cell comprising said TCR, or the antibody specifically binding to a portion of the TCR as described herein.

Those active components of the present invention are preferably used in such a pharmaceutical composition, in doses mixed with an acceptable carrier or carrier material, that the disease can be treated or at least alleviated. Such a composition can (in addition to the active component and the carrier) include filling material, salts, buffer, stabilizers, solubilizers and other materials, which are known state of the art.

The term "pharmaceutically acceptable" defines a non-toxic material, which does not interfere with effectiveness of the biological activity of the active component. The choice of the carrier is dependent on the application.

The pharmaceutical composition may contain additional components which enhance the activity of the active component or which supplement the treatment. Such additional components and/or factors can be part of the pharmaceutical composition to achieve synergistic effects or to minimize adverse or unwanted effects.

Techniques for the formulation or preparation and application/medication of active components of the present invention are published in "Remington's Pharmaceutical Sciences", Mack Publishing Co., Easton, PA, latest edition. An appropriate application is a parenteral application, for example intramuscular, subcutaneous, intramedular injections as well as intrathecal, direct intraventricular, intravenous, intranodal, intraperitoneal or intratumoral injections. The intravenous injection is the preferred treatment of a patient.

According to a preferred embodiment, the pharmaceutical composition is an infusion or an injection.

An injectable composition is a pharmaceutically acceptable fluid composition comprising at least one active ingredient, e.g. an expanded T cell population (for example autologous or allogenic to the patient to be treated) expressing a TCR. The active ingredient is usually dissolved or suspended in a physiologically acceptable carrier, and the composition can additionally comprise minor amounts of one or more non-toxic auxiliary substances, such as emulsifying agents, preservatives, and pH buffering agents and the like. Such injectable compositions that are useful for use with the fusion proteins of this disclosure are conventional; appropriate formulations are well known to those of ordinary skill in the art.

Typically, the pharmaceutical composition comprises at least one pharmaceutically acceptable carrier.

Accordingly, another aspect of the invention refers to the TCR as described herein, the polypeptide comprising a functional portion of said TCR, the multivalent TCR complex according as described herein, the nucleic acid encoding said TCR, the vector comprising said nucleic acid, the cell comprising said TCR, or the antibody specifically binding to a portion of the TCR as described herein for use as a medicament.

Some embodiments refer to the TCR as described herein, the polypeptide comprising a functional portion of said TCR, the multivalent TCR complex according as described herein, the nucleic acid encoding said TCR, the vector comprising said nucleic acid, the cell comprising said TCR for use in the treatment of cancer.

In one embodiment the cancer is a hematological cancer.

Hematological cancers also called blood cancers which do not form solid tumors and therefore are primarily dispersed in the body.

The hematological cancer may be selected from the group consisting of, non-Hodgkin's lymphoma (NHL), Hodgkin's lymphoma (HL), multiple myeloma, acute myeloid leukemia (AML) and acute lymphoblastic leukemia (ALL), mixed phenotype acute leukemia (MPAL), chronic myeloid leukemia (CML), B cell polymorphic lymphoma, hairy cell leukemia, chronic lymphocytic leukemia (CLL), small lymphocytic lymphoma (SLL), central nervous system lymphoma, CD37+ dendritic cell lymphoma, lymphoplasmatic lymphoma, splenic marginal zone lymphoma, plasma cell myeloma, extraosscuos plasmacytoma, extra-nodal marginal zone B-cell lymphoma of mucosa-associated lymphoid tissue (MALT tissue), nodal marginal zone B-cell lymphoma, follicular lymphoma, mantel cell lymphoma, diffuse large B-cell lymphoma, mediastinal (thymic) large B-cell lymphoma, precursor B-lymphoblastic lymphoma, immunoblastic large cell lymphoma, intravascular large B-cell lymphoma, primary effusion lymphoma, Burkitt's lymphoma/leukemia, B-cell proliferations of uncertain malignant potential, lymphomatoid granulomatosis, post-transplant lymphoproliferative disorder. Other hematological cancers or disorders include myelodysplastic disorder.

Also contemplated herein are pharmaceutical compositions and kits containing one or more of (i) an isolated TCR as described herein; (ii) viral particles comprising a nucleic acid encoding a recombinant TCR; (iii) immune cells, such as T cells or NK cells, modified to express a recombinant TCR as described herein; (iv) nucleic acids encoding a recombinant TCR as described herein. In some embodiments, the present disclosure provides compositions comprising lentiviral vector particles comprising a nucleotide sequence encoding a recombinant TCR described herein (or T cells that have been modified using the vector particles described herein to express a recombinant TCR). Such compositions can be administered to subjects in the methods of the present disclosure as described further herein.

Compositions comprising the modified T cells as described herein can be utilized in methods and compositions for adoptive immunotherapy in accordance with known techniques, or variations thereof that will be apparent to those skilled in the art based on the instant disclosure.

In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin.

The number of cells for an effective treatment in the composition is typically greater than 10 cells, and up to $10^6$, up to and including $10^8$ or $10^9$ cells and can be more than $10^{10}$ cells. The number of cells will depend upon the ultimate use for which the composition is intended as will the type of cells included therein. For example, if cells that are specific for a particular antigen are desired, then the population will contain greater than 70%, generally greater than 80%, 85% and 90-95% of such cells. For uses provided herein, the cells are generally in a volume of a liter or less, can be 500 ml or less, even 250 ml or 100 ml or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^9$, $10^{10}$ or $10^{11}$ cells. Pharmaceutical compositions provided herein can be in various forms, e.g., in solid, liquid, powder, aqueous, or lyophilized form. Examples of suitable pharmaceutical carriers are known in the art. Such carriers and/or additives can be formulated by conventional methods and can be administered to the subject at a suitable dose. Stabilizing agents such as lipids, nuclease inhibitors, polymers, and chelating agents can preserve the compositions from degradation within the body. In a composition intended to be administered by injection, one or more of a surfactant, preservative, wetting agent, dispersing agent, suspending agent, buffer, stabilizer and isotonic agent may be included.

The recombinant TCRs as described herein, or the viral vector particles comprising a nucleotide sequence encoding a recombinant TCR provided herein, can be packaged as kits. Kits can optionally include one or more components such as instructions for use, devices, and additional reagents, and components, such as tubes, containers and syringes for practice of the methods. Exemplary kits can include the nucleic acids encoding the recombinant TCRs, the recombinant TCR polypeptides, or viruses provided herein, and can optionally include instructions for use, a device for detecting a virus in a subject, a device for administering the compositions to a subject, and a device for administering the compositions to a subject.

Kits comprising polynucleotides encoding a gene of interest (e.g., a recombinant TCR) are also contemplated herein. Kits comprising a viral vector encoding a sequence of interest (e.g., a recombinant TCR) and optionally, a polynucleotide sequence encoding an immune checkpoint inhibitor are also contemplated herein.

Kits contemplated herein also include kits for carrying out the methods for detecting the presence of polynucleotides encoding any one or more of the TCRs disclosed herein. In particular, such diagnostic kits may include sets of appropriate amplification and detection primers and other associated reagents for performing deep sequencing to detect the polynucleotides encoding TCRs disclosed herein. In further embodiments, the kits herein may comprise reagents for detecting the TCRs disclosed herein, such as antibodies or other binding molecules. Diagnostic kits may also contain instructions for determining the presence of the polynucleotides encoding the TCRs disclosed herein or for determining the presence of the TCRs disclosed herein. A kit may also contain instructions. Instructions typically include a tangible expression describing the components included in the kit, and methods for administration, including methods for determining the proper state of the subject, the proper dosage amount, and the proper administration method. Instructions can also include guidance for monitoring the subject over the duration of the treatment time.

Kits provided herein also can include a device for administering a composition described herein to a subject. Any of a variety of devices known in the art for administering medications or vaccines can be included in the kits provided herein. Exemplary devices include, but are not limited to, a hypodermic needle, an intravenous needle, a catheter, a needle-less injection device, an inhaler, and a liquid dispenser, such as an eyedropper. Typically, the device for administering a virus of the kit will be compatible with the virus of the kit; for example, a needle-less injection device such as a high pressure injection device can be included in kits with viruses not damaged by high pressure injection, but is typically not included in kits with viruses damaged by high pressure injection.

Kits provided herein also can include a device for administering a compound, such as a T cell activator or stimulator, or a TLR agonist, such as a TLR4 agonist to a subject. Any of a variety of devices known in the art for administering medications to a subject can be included in the kits provided herein. Exemplary devices include a hypodermic needle, an intravenous needle, a catheter, a needle-less injection, but are not limited to, a hypodermic needle, an intravenous needle, a catheter, a needle-less injection device, an inhaler, and a liquid dispenser such as an eyedropper. Typically, the device for administering the compound of the kit will be compatible with the desired method of administration of the compound.

Experiments

EXAMPLES

Example 1: HA-1$^H$-TCR-Transgenic T Cells Bind HA-1$^H$-Multimers

An in vitro priming approach to isolate HA-1$^H$-reactive T-cell clones was used. The priming system uses mature dendritic cells (mDCs) of an HLA-A*02:01 positive donor as antigen-presenting cells and autologous CD8+-enriched T cells as responding cells. In vitro transcribed RNA (ivtRNA) encoding 31 amino acids of the human HMHA1 gene (ARFAEGLEKLKECVLHDDLLEARRPRAHECL; SEQ ID NO: 126) serves as the source of specific antigen. After electroporation into the mDCs, the HMHA1-encoding ivtRNA is translated into protein, which is subsequently processed and presented as peptides by HLA-A*02:01 molecules on the mDCs. In vitro co-cultures of T cells with the ivtRNA-transfected mDCs from the same donor lead to de novo induction of antigen-specific T cells that serve as the source of corresponding TCRs. Antigen-specific T cells can be enriched by a variety of methods and are cloned by limiting dilution or FACS-based single cell sorting. Sequences of TCR alpha and TCR beta chains of HA-1$^H$-reactive T-cell clones are identified by Next Generation Sequencing and after exchanging the constant TCR regions by their murine counterparts cloned into the retroviral vector pES. 12-6. PBMCs of a healthy donor are isolated by ficoll gradient centrifugation. CD8 T-cells are enriched by negative magnetic selection (Miltenyi) and stimulated in non-tissue culture 24-well plates with anti-CD3 and anti-CD28 mAb (BD Pharmingen, Heidelberg, Germany). Amphotropic retroviral particles are produced by transfection of HEK293T cells with the respective TCR encoding retroviral plasmid and two expression plasmids. On day two after stimulation, CD8 T cells are transduced and on day twelve enriched for transduced CD8+ cells by FACS using the murine constant beta region as a marker for transduction and then expanded by the rapid expansion protocol (Riddell S R, Science, 1992 Jul. 10; 257 (5067): 238-41).
Results:
CD8 T cells were transduced with six different TCRs isolated from HA-1$^H$-reactive T-cell clones and one control TCR that did not recognize HA-1$^H$. The nucleotide sequences of the isolated TCRs were codon optimized using the GeneOptimizer™ algorithm (ThermoFisher) and the constant regions were murinized. Codon optimized and murinized TCRs were used for all further experiments described herein. They were stained with an HA-1$^H$-MHC-multimer (immunAware) and antibodies against CD8 and the murine constant beta region. All but one of the HA-1$^H$-TCR-transgenic T cell populations bound the HA-1$^H$-MHC-multimer very efficiently (>90%); only TCR_6 showed a lower percentage of HA-1$^H$-MHC-multimer-positive cells (37%). No HA-1$^H$-MHC-multimer-staining was observed with the control TCR. These results show that TCRs isolated from HA-1$^H$-reactive T-cell clones can be transgenically expressed in T cells of a healthy donor. (FIG. 1)

Example 2: HA-1$^H$-TCR-Transgenic T Cells Recognize HA-1$^H$-Positive Target Cells HA-1$^H$ specificity of TCR-transgenic T cells was confirmed according to the following protocol:
As target cells, T2 cells (HLA-A*02:01$^{pos}$) are loaded with saturating amounts (105 M) of HA-1$^H$ peptide (SEQ ID NO: 2) or the control peptide Astn1 P1268L (KLYGLD-WAEL (SEQ ID NO: 65)). In addition, K562 cells are transduced with HLA-A*02:01 and part of the HMHA1 gene encoding the HA-1$^H$-epitope. K562 cells transduced only with HLA-A*02:01 are used as a control. Each target cell line is co-cultured with TCR-transgenic T cells at a ratio of 2:1 using 20,000 T cells and 10,000 target cells. After 20-24 h, IFN-γ concentrations in co-culture supernatants are analyzed by standard sandwich ELISA (BD human IFN-γ ELISA set).
Results:
HA-1$^H$-TCR-transgenic T cells recognized HA-1$^H$-loaded T2 and HMHA1-transduced K562 cells but none of the control target cells. T cells expressing the control TCR only recognized T2 cells loaded with the control peptide. These results show that TCRs isolated from HA-1$^H$-reactive T-cell clones are functional when transferred to T cells of a healthy donor. (FIG. 2)

Example 3: HA-1$^H$-TCR-Transgenic T Cells do not Recognize HA-1$^R$-Peptide-Loaded Target Cells To analyze the difference in recognizing the two variants HA-1$^H$ and HA-1$^R$, the functional avidity of HA-1$^H$-TCR-transgenic T cells against the two variants loaded on HLA-A*02:01 was analyzed:

T2 cells are externally loaded with different concentrations ($10^{-11}$ M-$10^{-5}$ M) for the HA-1$^H$-peptide and ($10^{-8}$ M-$10^{-5}$ M) for the HA-1$^R$ peptide and co-cultured with TCR-transgenic T cells at a ratio of 2:1 using 20,000 T cells and 10,000 T2 cells. After 20-24 h, IFN-γ concentrations in co-culture supernatants are analyzed by standard sandwich ELISA (BD human IFN-γ ELISA set).
Results:
The highest functional avidity against HA-1$^H$-peptide loaded on HLA-A*02:01 encoded molecules was shown by TCR_3 and TCR_4, and the lowest functional avidity by TCR_2. Only very little recognition of HA-1$^R$ by some of the HA-1$^H$-TCR-transgenic T cells was observed at unphysiologically high peptide concentrations ($10^{-5}$ M) and for recognition of the HA-1$^R$-variant at least 10,0000 times higher peptide concentrations compared to HA-1$^H$ were needed for all of the HA-1$^H$-TCR-transgenic T cells. These results show that the HA-1$^H$-TCRs are highly specific for the HA-1$^H$-variant. In addition, the functional avidity against HA-1$^R$-peptide loaded on HLA-A*02:01 encoded molecules was compared with a TCR (TCR2) as described in WO2018058002A1. In contrast to the TCRs described herein, this TCR recognizes HA-1$^R$-peptide also at a concentration of $10^{-6}$ M and released significantly more IFN-γ at a concentration of $10^{-5}$ M, showing that all TCRs described herein are more specific than the TCR as described in WO2018058002A1. (FIGS. 3A and 3B)

Example 4: HA-1$^H$-TCR-Transgenic T Cells Recognize HA-1$^H$-Positive LCL

To analyze the ability of HA-1$^H$-TCR-transgenic T cells to recognize HA-1$^H$ at physiological levels on unmodified target cells, T cells were co-cultured with different lymphoblastoid cell lines (LCL) and cytokine release and cytotoxicity of TCR-transgenic T cells was analyzed:
DNA of seven LCL is isolated (Quick Extract DNA Extract Solution, Illumina) and the part of the HMHA1 gene encoding HA-1 was amplified by PCR. The PCR product is isolated from an agarose gel send for sequencing (Eurofins Genomics). Based on the sequencing results LCLs were assigned to either the HA-1$^H$-positive (HA-1$^{H/H}$ and HA-1$^{H/R}$) or HA-1$^H$-negative (HA-1$^{R/R}$) group. To analyze cytokine release, TCR-transgenic T cells and LCLs are co-cultured at a ratio of 2:1 using 20,000 T cells and 10,000 T2 cells. After 20-24 h, IFN-γ concentrations in co-culture supernatants are analyzed by standard sandwich ELISA (BD human IFN-γ ELISA set). For cytotoxicity assays, the co-cultures are set-up at an effector-to-target ratio of 5:1, with 100,000 TCR-transgenic T cells and 20,000 LCLs that have been transduced with a fluorescent marker gene. A decrease of fluorescent target cells (Total Integrated Intensity in RCU×μm²/Image, RCU=red calibration unit) is measured every two hours over a total time period of 20 hours using live-cell monitoring (IncuCyte® ZOOM).
Results:
All HA-1$^H$-TCR-transgenic T cells released IFN-γ when co-cultured with HA-1$^H$-positive LCLs (LCL 1-5), but not after co-culture with HA-1$^H$-negative LCLs (LCL 6-7). T cells expressing the control TCR did not recognize any of the LCLs. In addition, HA-1$^H$-positive LCLs were lyzed by HA-1$^H$-TCR-transgenic T cells. Untransduced CD8 T cells were used as a negative control and did not lyze LCLs. These results show that the HA-1$^H$-TCRs can recognize HA-1$^H$-loaded on HLA-A*02:01 encoded molecules at physiological levels. (FIGS. 4A and 4B)

Example 5: HA-1$^H$-TCR-Transgenic T Cells Recognize HA-1$^H$-Positive Tumor Cell Lines To analyze the ability of HA-1$^H$-TCR-transgenic T cells to recognize HA-1$^H$ presented on tumor cell lines, T cells were co-cultured with different HA-1$^H$-positive tumor cell lines.

DNA of tumor cell lines is isolated (Quick Extract DNA Extract Solution, Illumina) and the part of the HMHA1 gene encoding HA-1 was amplified by PCR. The PCR product is isolated from an agarose gel and extracted from the gel for subsequent sequencing (Eurofins Genomics). HA-1$^H$-positive (HA-1$^{H/H}$ and HA-1$^{H/R}$) tumor cell lines are used for the experiment. To analyze cytokine release, TCR-transgenic T cells and tumor cell lines are co-cultured at a ratio of 2:1 using 20,000 T cells and 10,000 T2 cells. After 20-24 h, IFN-γ concentrations in co-culture supernatants are analyzed by standard sandwich ELISA (BD human IFN-γ ELISA set). For cytotoxicity assays, the co-cultures are set-up at an effector-to-target ratio of about 5:1, with 100,000 TCR-transgenic T cells and 20,000 tumor cells that have been transduced with a fluorescent marker gene. A decrease of fluorescent target cells (Total Integrated Intensity in RCU× μm²/Image, RCU=red calibration unit) is measured every two hours over a total time period of 20 hours using live-cell monitoring (IncuCyte® ZOOM).
Results:

All HA-1$^H$-TCR-transgenic T cells but TCR_2 released IFN-γ when co-cultured with the tumor cell lines. T cells expressing the control TCR did not recognize the tumor cell lines. HA-1$^H$-TCR-transgenic T cells also show cytotoxic activity against the tumor cell lines. Consistent with the cytokine release data, TCR_2 lyzed the target cells less efficiently. Untransduced CD8 T cells were used as a negative control. (FIGS. 5A and 5B)

Example 6: T Cells Expressing TCR_3 and TCR_4 Recognize HA-1$^H$-Positive Tumor Cell Lines at Comparable Levels as a Previously Described TCR To compare the recognition of HA-1$^H$-positive tumor cell lines by HA-1$^H$-TCR-transgenic T cells to T cells expressing TCR2 described in WO2018058002A1, 20,000 T cells and 10,000 tumor cells are co-cultured. After 20 h, IFN-γ concentrations in co-culture supernatants are analyzed by standard sandwich ELISA (BD human IFN-γ ELISA set). For cytotoxicity assays, 10,000 HA-1$^H$-negative/GFP-positive K562 cells and 10,000 cells of a mCherry expressing tumor cell line are co-cultured with 20,000 TCR-transgenic T cells. After 45 h, samples are analyzed by flow cytometry and the ratio of mCherry-positive (HA-1$^H$-positive) to GFP-positive (HA-1$^H$-negative) cells is calculated and normalized to the ratio measured for the control TCR.
Results:

T cells expressing TCR_3 and TCR_4 released similar amounts of IFN-γ after co-culture with HA-1$^H$-positive tumor cell lines as T cells expressing TCR2 described in WO2018058002A1 (FIG. 6A). T cells expressing TCR_3 and TCR_4 also show comparable cytotoxic activity against different tumor cell lines as TCR2 (FIG. 6B).

Example 7: TCR Recognition Motif

For the analysis of the TCRs' specific recognition motifs, a serine-substitution scan is performed. By single substitutions of the epitope's original amino acids by serine, positions within the peptide that are essential for TCR-mediated recognition can be identified. To define the recognition motif, effector T cells expressing different HA-1 TCRs (TCR_3, TCR_4 and TCR2 as described in WO2018058002A1) ae co-cultured with T2 cells loaded with the HA-1$^H$ peptide (SEQ ID NO: 2), with peptides having each individual amino acid residue consecutively substituted by serine or with a control peptide. T2 cells are separately loaded with saturating concentrations (105 M) of the peptides, washed and co-cultured with the effectors at an E:T of 1:1. Supernatants are harvested after ~20 h of co-culture and secreted IFN-γ is analyzed by ELISA. T cells expressing a control TCR are used as a negative control.
Results:

TCR_3 and TCR_4 show a more specific recognition pattern in the serine compared to TCR2 (WO2018058002A1), as less peptides were recognized.
Comparison of Different Constant TCR Regions To compare the effect of different constant TCR regions, TCR_3 is cloned with murine, minimally murinized (Sommermeyer and Uckert, 2010, J. Immunol.) and human constant regions. Recognition of HA-1$^H$-positive tumor cell lines or LCL by HA-1$^H$-TCR-transgenic T cells with different constant TCR regions is tested by co-culture of 20,000 T cells 10,000 tumor cells. After 20-24 h, IFN-γ concentrations in co-culture supernatants are analyzed by standard sandwich ELISA (BD human IFN-γ ELISA set). For cytotoxicity assays, 10,000 HA-1$^H$-negative/GFP-positive K562 cells and 10,000 cells of a mCherry expressing tumor cell line are co-cultured with 20,000 TCR-transgenic T cells. After 45 h, the samples are analyzed by flow cytometry and the ratio of mCherry-positive (HA-1$^H$-positve) to GFP-positive (HA-1$^H$-negative) cells is calculated and normalized to the ratio measured for the control TCR.
Results:

As expected, the reactivity of HA-1$^H$-TCR-transgenic T cells slightly decreases when minimally murinized or human constant TCR regions are used instead of murinized constant regions (FIGS. 8A and B). However, even with human constant TCR regions, T cells still specifically release IFN-γ and show cytotoxic effects after co-culture with HA-1$^H$-positive target cells.

The description further comprises the following embodiments:

Embodiment 1

Isolated T cell receptor (TCR) specific for one allelic variant of minor histocompatibility antigen 1 (HA-1).

Embodiment 2

Isolated TCR according to embodiment 1, wherein the allelic variant of HA-1 is HA-1$^H$

Embodiment 3

Isolated TCR according to any one of the preceding embodiments, wherein the TCR specifically recognizes the amino acid sequence SEQ ID NO: 2 or a fragment thereof.

Embodiment 4

Isolated TCR according to any one of the preceding embodiments, wherein the TCR does not recognize the amino acid sequence SEQ ID NO: 4 or a fragment thereof.

Embodiment 5

Isolated TCR according to any one of the preceding embodiments, wherein recognition motif of the TCR comprises at least the sequence set out in SEQ ID NO: 127.

Embodiment 6

Isolated TCR according to any one of the preceding embodiments, wherein the TCR specifically recognizes the HLA-A2 bound form of the amino acid sequence of SEQ ID NO: 2.

Embodiment 7

Isolated TCR according to any of the preceding embodiments, wherein the TCR specifically recognizes the amino acid sequence of SEQ ID NO: 2, which is presented by the HLA-A*02:01 encoded molecule.

Embodiment 8

Isolated TCR according to any of the preceding embodiments, wherein the TCR comprises a TCR α chain comprising a complementarity-determining region 3 (CDR3) having the amino acid sequence selected from the group consisting of SEQ ID NO: 7, SEQ ID NO: 17, SEQ ID NO: 27, SEQ ID NO: 37, SEQ ID NO: 47 and SEQ ID NO: 57.

Embodiment 9

Isolated TCR according to any one of the preceding embodiments, wherein the TCR comprises a TCR β chain comprising a CDR3 having the amino acid sequence selected from the group consisting of SEQ ID NO: 10, SEQ ID NO: 20, SEQ ID NO: 30, SEQ ID NO: 40 SEQ ID NO: 50 and SEQ ID NO: 60.

Embodiment 10

Isolated TCR according to any one of the preceding embodiments, wherein the TCR comprises
- a)—a TCR α chain comprising a CDR1 having the amino acid sequence of SEQ ID NO: 5, a CDR 2 having the amino acid sequence of SEQ ID NO: 6 and a CDR 3 having the sequence of SEQ ID NO: 7,
  a TCR β chain comprising a CDR1 having the amino acid sequence of SEQ ID NO: 8, a CDR 2 having the amino acid sequence of SEQ ID NO: 9 and a CDR 3 having the sequence of SEQ ID NO: 10; or
- b)—a TCR α chain comprising a CDR1 having the amino acid sequence of SEQ ID NO: 15, a CDR 2 having the amino acid sequence of SEQ ID NO: 16 and a CDR 3 having the sequence of SEQ ID NO: 17,
  a TCR β chain comprising a CDR1 having the amino acid sequence of SEQ ID NO: 18, a CDR 2 having the amino acid sequence of SEQ ID NO: 19 and a CDR 3 having the sequence of SEQ ID NO: 20; or
- c)—a TCR α chain comprising a CDR1 having the amino acid sequence of SEQ ID NO: 25, a CDR 2 having the amino acid sequence of SEQ ID NO: 26 and a CDR 3 having the sequence of SEQ ID NO: 27,
  a TCR β chain comprising a CDR1 having the amino acid sequence of SEQ ID NO: 28, a CDR 2 having the amino acid sequence of SEQ ID NO: 29 and a CDR 3 having the sequence of SEQ ID NO: 30;
- d)—a TCR α chain comprising a CDR1 having the amino acid sequence of SEQ ID NO: 35, a CDR 2 having the amino acid sequence of SEQ ID NO: 36 and a CDR 3 having the sequence of SEQ ID NO: 37,
  a TCR β chain comprising a CDR1 having the amino acid sequence of SEQ ID NO: 38, a CDR 2 having the amino acid sequence of SEQ ID NO: 39 and a CDR 3 having the sequence of SEQ ID NO: 40; or
- e)—a TCR α chain comprising a CDR1 having the amino acid sequence of SEQ ID NO: 45, a CDR 2 having the amino acid sequence of SEQ ID NO: 46 and a CDR 3 having the sequence of SEQ ID NO: 47,
  a TCR β chain comprising a CDR1 having the amino acid sequence of SEQ ID NO: 48, a CDR 2 having the amino acid sequence of SEQ ID NO: 49 and a CDR 3 having the sequence of SEQ ID NO: 50; or
- f)—a TCR α chain comprising a CDR1 having the amino acid sequence of SEQ ID NO: 55, a CDR 2 having the amino acid sequence of SEQ ID NO: 56 and a CDR 3 having the sequence of SEQ ID NO: 57.
  a TCR β chain comprising a CDR1 having the amino acid sequence of SEQ ID NO:58, a CDR 2 having the amino acid sequence of SEQ ID NO: 59 and a CDR 3 having the sequence of SEQ ID NO: 60.

Embodiment 11

Isolated TCR according to any one of the preceding embodiments, wherein the TCR comprises a TCR α chain and a TCR β chain, wherein
- a)—the variable TCR α region has an amino acid sequence which is at least 80% identical to SEQ ID NO: 11 and comprises a CDR3 region having an amino acid sequence set out in SEQ ID NO: 7,
  the variable TCR β region has an amino acid sequence which is at least 80% identical to SEQ ID NO: 12 and comprises a CDR3 region having an amino acid sequence set out SEQ ID NO: 10 or
- b)—the variable TCR α region has an amino acid sequence which is at least 80% identical to SEQ ID NO: 21 and comprises a CDR3 region having an amino acid sequence set out in SEQ ID NO: 17,
  the variable TCR β region has an amino acid sequence which is at least 80% identical to SEQ ID NO: 22 and comprises a CDR3 region having an amino acid sequence set out SEQ ID NO: 20; or
- c)—the variable TCR α region has an amino acid sequence which is at least 80% identical to SEQ ID NO: 31 and comprises a CDR3 region having an amino acid sequence set out in SEQ ID NO: 27;
  the variable TCR β region has an amino acid sequence which is at least 80% identical to SEQ ID NO: 32 and comprises a CDR3 region having an amino acid sequence set out SEQ ID NO: 30; or
- d)—the variable TCR α region has an amino acid sequence which is at least 80% identical to SEQ ID NO: 41 and comprises a CDR3 region having an amino acid sequence set out in SEQ ID NO: 37;
  the variable TCR β region has an amino acid sequence which is at least 80% identical to SEQ ID NO: 42 and comprises a CDR3 region having an amino acid sequence set out SEQ ID NO: 40; or
- e)—the variable TCR α region has an amino acid sequence which is at least 80% identical to SEQ ID NO: 51 and comprises a CDR3 region having an amino acid sequence set out in SEQ ID NO: 47;

the variable TCR β region has an amino acid sequence which is at least 80% identical to SEQ ID NO: 52 and comprises a CDR3 region having an amino acid sequence set out SEQ ID NO: 50; or f)—the variable TCR α region has an amino acid sequence which is at least 80% identical to SEQ ID NO: 61 and comprises a CDR3 region having an amino acid sequence set out in SEQ ID NO: 57;

the variable TCR β region has an amino acid sequence which is at least 80% identical to SEQ ID NO: 62 and comprises a CDR3 region having an amino acid sequence set out SEQ ID NO: 60.

Embodiment 12

Isolated TCR according to any one of the preceding embodiments, wherein the TCR comprises
- a) a variable TCR α region having an amino acid sequence which is at least 80% identical to SEQ ID NO: 11 and a variable TCR β region having an amino acid sequence which is at least 80% identical to SEQ ID NO: 12; or
- b) a variable TCR α region having an amino acid sequence which is at least 80% identical to SEQ ID NO: 21 and a variable TCR β region having an amino acid sequence which is at least 80% identical to SEQ ID NO: 22; or
- c) a variable TCR α region having an amino acid sequence which is at least 80% identical to SEQ ID NO: 31 and a variable TCR β region having an amino acid sequence which is at least 80% identical to SEQ ID NO: 32; or
- d) a variable TCR α region having an amino acid sequence which is at least 80% identical to SEQ ID NO: 41 and a variable TCR β region having an amino acid sequence which is at least 80% identical to SEQ ID NO: 42; or
- e) a variable TCR α region having an amino acid sequence which is at least 80% identical to SEQ ID NO: 51 and a variable TCR β region having an amino acid sequence which is at least 80% identical to SEQ ID NO: 52; or
- f) a variable TCR α region having an amino acid sequence which is at least 80% identical to SEQ ID NO: 61 and a variable TCR β region having an amino acid sequence which is at least 80% identical to SEQ ID NO: 62.

Embodiment 13

Isolated TCR according to any one of the preceding embodiments, wherein the TCR comprises a) a variable TCR α region having the amino acid sequence of SEQ ID NO: 11 and a variable TCR β region having the amino acid sequence of SEQ ID NO: 12; or
- b) a variable TCR α region having the amino acid sequence of SEQ ID NO: 21 and a variable TCR β region having the amino acid sequence of SEQ ID NO: 22; or
- c) a variable TCR α region having the amino acid sequence of SEQ ID NO: 31 and a variable TCR β region having the amino acid sequence of SEQ ID NO: 32; or
- d) a variable TCR α region having the amino acid sequence of SEQ ID NO: 41 and a variable TCR β region having the amino acid sequence of SEQ ID NO: 42; or
- e) a variable TCR α region having the amino acid sequence of SEQ ID NO: 51 and a variable TCR β region having the amino acid sequence of SEQ ID NO: 52; or
- f) a variable TCR α region having the amino acid sequence of SEQ ID NO: 61 and a variable TCR β region having the amino acid sequence of SEQ ID NO: 62.

Embodiment 14

Isolated TCR according to any one of the preceding embodiments, wherein the TCR is purified.

Embodiment 15

Isolated TCR according to any one of the preceding embodiments, wherein its amino acid sequence comprises one or more phenotypically silent substitutions.

Embodiment 16

Isolated TCR according to any one of the preceding embodiments, wherein its amino acid sequence is modified to comprise a detectable label, a therapeutic agent or pharmacokinetic modifying moiety.

Embodiment 17

Isolated TCR according to embodiment 16, wherein the therapeutic agent is selected from the group consisting of an immune effector molecule, a cytotoxic agent and a radionuclide.

Embodiment 18

Isolated TCR according to embodiment 17, wherein the immune effector molecule is a cytokine.

Embodiment 19

Isolated TCR according to any one of the preceding embodiments, wherein the TCR is soluble or membrane bound.

Embodiment 20

Isolated TCR according to embodiment 16, wherein the pharmacokinetic modifying moiety is at least one polyethylene glycol repeating unit, at least one glycol group, at least one sialyl group or a combination thereof.

Embodiment 21

Isolated TCR according to any one of the preceding embodiments, wherein the TCR is of the single chain type, wherein the TCR α chain and the TCR β chain are linked by a linker sequence.

Embodiment 22

Isolated TCR according to any one of the preceding embodiments, wherein the TCR α chain or the TCR β chain is modified to comprise an epitope tag.

Embodiment 23

Isolated TCR according to any one of the preceding embodiments, wherein the recombinant TCR sequence may be modified to contain minimal murinized Cox and CB regions.

Embodiment 24

Isolated polypeptide comprising a functional portion of the TCR of any of embodiments 1 to 21, wherein the functional portion comprises at least one of the amino acid sequences of SEQ ID NO: 7, SEQ ID NO: 17, SEQ ID NO: 27, SEQ ID NO: 37, SEQ ID NO: 47, SEQ ID NO: 57, SEQ ID NO: 10, SEQ ID NO: 20, SEQ ID NO: 30, SEQ ID NO: 40, SEQ ID NO: 50 and SEQ ID NO: 60.

Embodiment 25

Isolated polypeptide according to embodiment 24, wherein the functional portion comprises the TCR α variable chain and/or the TCR β variable chain.

Embodiment 26

Multivalent TCR complex, comprising a least two TCRs as embodied in any one of embodiments 1 to 23.

Embodiment 27

Multivalent TCR complex, wherein at least one of said TCRs is associated with a therapeutic agent.

Embodiment 28

Isolated TCR according to embodiments 1 to 23, polypeptide according to embodiments 24 and 25, multivalent TCR complex according to embodiments 25 and 26, wherein IFN-γ secretion is induced by binding to the amino acid sequence of SEQ ID NO: 2, which is presented by the HLA-A*02:01 encoded molecule.

Embodiment 29

Nucleic acid encoding a TCR according to any one of embodiments 1 to 22 or encoding the polypeptide according to embodiments 24 to 25.

Embodiment 30

Nucleic acid according to embodiment 29, wherein the nucleic acid is codon optimized.

Embodiment 31

Vector comprising the nucleic acid of embodiment 29 or 30.

Embodiment 32

Vector according to embodiment 31, wherein the vector is an expression vector.

Embodiment 33

Vector according to embodiment 31 or 32, wherein the vector is a retroviral vector.

Embodiment 34

Vector according to embodiment 31 or 32, wherein the vector is a lentiviral vector.

Embodiment 35

Cell expressing the TCR according to embodiments 1 to 23.

Embodiment 36

Cell according to embodiment 34, wherein the cell is isolated or non-naturally occurring.

Embodiment 37

Cell comprising the nucleic acid according to embodiments 29 or 30 or the vector according to embodiments 31 to 35.

Embodiment 38

Cell according to embodiments 35 to 37, wherein the cell comprises:
a) an expression vector which comprises at least one nucleic acid as embodied in embodiment 29 or 30.
b) a first expression vector which comprises a nucleic acid encoding the alpha chain of the TCR as embodied in any one of the embodiments 1 to 23, and a second expression vector which comprises a nucleic acid encoding the beta chain of a TCR as embodied in any one of the embodiments 1 to 23.

Embodiment 39

Cell according to any one of embodiments 35 to 38, wherein the cell is a peripheral blood lymphocyte (PBL) or a peripheral blood mononuclear cell (PBMC).

Embodiment 40

Cell according to any one of embodiments 35 to 38, wherein the cell is a T cell.

Embodiment 41

Antibody or antigen binding fragment thereof specifically binding to a portion of the TCR according to embodiments 1 to 23 that mediates specificity for one allelic variant of HA-1.

Embodiment 42

Antibody or antigen binding fragment thereof according to embodiment 40, wherein the portion of the TCR that mediates the specificity for one allelic variant of HA-1 comprises the CDR3 of the alpha chain of SEQ ID NO: 7, SEQ ID NO: 17, SEQ ID NO: 27, SEQ ID NO: 37, SEQ ID NO: 47, SEQ ID NO: 57, and/or the CDR3 of the beta chain of SEQ ID NO: 10, SEQ ID NO: 20, SEQ ID NO: 30, SEQ ID NO: 40, SEQ ID NO: 50 and SEQ ID NO: 60.

Embodiment 43

Antibody or antigen binding fragment thereof according to embodiment 41 or 42, wherein the allelic variant of HA-1 is HA-1$^H$.

Embodiment 44

Pharmaceutical composition comprising the TCR according to embodiments 1 to 22, the polypeptide according to embodiments 24 to 25, the multivalent TCR complex according to any one of embodiments 27 to 28, the nucleic acid according to embodiment 29 or 30, the vector according to embodiments 31 to 34, the cell according to any one of embodiments 35 to 40, or the antibody according to embodiments 41 to 42.

Embodiment 45

Pharmaceutical composition according to embodiment 44, wherein the pharmaceutical composition comprises at least one pharmaceutically acceptable carrier.

Embodiment 46

The TCR according to embodiments 1 to 23, the polypeptide according to embodiments 24 to 25, the multivalent TCR complex according to any one of embodiments 27 to 28, the nucleic acid according to embodiment 29 or 30, the vector according to embodiments 31 to 34, the cell according to any one of embodiments 34 to 39, or the antibody according to embodiments 41 to 43 for use as a medicament.

Embodiment 47

The TCR according to embodiments 1 to 23, the polypeptide according to embodiments 24 to 25, the multivalent TCR complex according to any one of embodiments 26 to 27 the nucleic acid according to embodiment 29 or 30, or the cell according to any one of embodiments 35 to 40 for use in the treatment of cancer.

Embodiment 48

The TCR, the polypeptide, the multivalent TCR complex, the nucleic acid or the cell for use according to embodiment 45, wherein the cancer is a hematological cancer.

Embodiment 49

The TCR, the polypeptide, the multivalent TCR complex, the nucleic acid or the cell for use according to embodiment 45, wherein the hematological cancer is selected from the group consisting of non-Hodgkin's lymphoma (NHL), Hodgkin's lymphoma (HL), multiple myeloma, acute myeloid leukemia (AML), acute lymphoblastic leukemia (ALL), mixed phenotype acute leukemia (MPAL), chronic myeloid leukemia (CML), B cell polymorphic lymphoma, hairy cell leukemia, chronic lymphocytic leukemia (CLL), small lymphocytic lymphoma (SLL), central nervous system lymphoma, CD37+ dendritic cell lymphoma, lymphoplasmatic lymphoma, splenic marginal zone lymphoma, plasma cell myeloma, extraosseuos plasmacytoma, extra-nodal marginal zone B-cell lymphoma of mucosa-associated lymphoid tissue (MALT tissue), nodal marginal zone B-cell lymphoma, follicular lymphoma, mantel cell lymphoma, diffuse large B-cell lymphoma, mediastinal (thymic) large B-cell lymphoma, precursor B-lymphoblastic lymphoma, immunoblastic large cell lymphoma, intravascular large B-cell lymphoma, primary effusion lymphoma, Burkitt's lymphoma/leukemia, B-cell proliferations of uncertain malignant potential, lymphomatoid granulomatosis, post-transplant lymphoproliferative disorder and myelodysplastic disorder.

The invention claimed is:

1. An isolated T cell receptor (TCR) specific for one allelic variant of minor histocompatibility antigen 1 (HA-1), wherein the TCR comprises
   a TCR α chain comprising
   a CDR 1 (Complementarity Determining Region 1) having the amino acid sequence of SEQ ID NO: 25,
   a CDR 2 (Complementarity Determining Region 2) having the amino acid sequence of SEQ ID NO: 26, and
   a CDR 3 (Complementarity Determining Region 3) having the amino acid sequence of SEQ ID NO: 27 and
   a TCR β chain comprising
   a CDR 1 (Complementarity Determining Region 1) having the amino acid sequence of SEQ ID NO: 28,
   a CDR 2 (Complementarity Determining Region 2) having the amino acid sequence of SEQ ID NO: 29, and
   a CDR 3 (Complementarity Determining Region 3) having the amino acid sequence of SEQ ID NO: 30,
   wherein the TCR recognizes the amino acid sequence of SEQ ID NO: 2, and
   wherein the TCR comprises a variable TCR α region comprising the amino acid sequence of SEQ ID NO: 31 and a variable TCR β region comprising the amino acid sequence of SEQ ID NO: 32.

2. The isolated TCR according to claim 1, wherein the allelic variant of HA-1 is HA-1$^H$.

3. The isolated TCR according to claim 1, wherein the TCR does not recognize the amino acid sequence of SEQ ID NO:4.

4. The isolated TCR according to claim 1, wherein recognition motif of the TCR comprises the amino acid sequence of SEQ ID NO: 127.

5. A multivalent TCR complex, comprising a least two TCRs as claimed in claim 1.

6. A nucleic acid encoding a TCR according to claim 1.

7. A vector comprising the nucleic acid of claim 6.

8. A cell expressing the TCR according to claim 1.

* * * * *

SEQUENCE LISTING

```
<160> NUMBER OF SEQ ID NOS: 127

<210> SEQ ID NO 1
<211> LENGTH: 1136
<212> TYPE: PRT
<213> ORGANISM: Homo sapiens

<400> SEQUENCE: 1

Met Phe Ser Arg Lys Lys Arg Glu Leu Met Lys Thr Pro Ser Ile Ser
1               5                   10                  15

Lys Lys Asn Arg Ala Gly Ser Pro Ser Pro Gln Pro Ser Gly Glu Leu
            20                  25                  30

Pro Arg Lys Asp Gly Ala Asp Ala Val Phe Pro Gly Pro Ser Leu Glu
        35                  40                  45

Pro Pro Ala Gly Ser Ser Gly Val Lys Ala Thr Gly Thr Leu Lys Arg
    50                  55                  60

Pro Thr Ser Leu Ser Arg His Ala Ser Ala Ala Gly Phe Pro Leu Ser
65                  70                  75                  80

Gly Ala Ala Ser Trp Thr Leu Gly Arg Ser His Arg Ser Pro Leu Thr
                85                  90                  95

Ala Ala Ser Pro Gly Glu Leu Pro Thr Glu Gly Ala Gly Pro Asp Val
            100                 105                 110
```

```
Val Glu Asp Ile Ser His Leu Leu Ala Asp Val Ala Arg Phe Ala Glu
    115                 120                 125

Gly Leu Glu Lys Leu Lys Glu Cys Val Leu His Asp Asp Leu Leu Glu
130                 135                 140

Ala Arg Arg Pro Arg Ala His Glu Cys Leu Gly Glu Ala Leu Arg Val
145                 150                 155                 160

Met His Gln Ile Ile Ser Lys Tyr Pro Leu Leu Asn Thr Val Glu Thr
                165                 170                 175

Leu Thr Ala Ala Gly Thr Leu Ile Ala Lys Val Lys Ala Phe His Tyr
                180                 185                 190

Glu Ser Asn Asn Asp Leu Glu Lys Gln Glu Phe Glu Lys Ala Leu Glu
            195                 200                 205

Thr Ile Ala Val Ala Phe Ser Ser Thr Val Ser Glu Phe Leu Met Gly
        210                 215                 220

Glu Val Asp Ser Ser Thr Leu Leu Ala Val Pro Pro Gly Asp Ser Ser
225                 230                 235                 240

Gln Ser Met Glu Ser Leu Tyr Gly Pro Gly Ser Glu Gly Thr Pro Pro
                245                 250                 255

Ser Leu Glu Asp Cys Asp Ala Gly Cys Leu Pro Ala Glu Glu Val Asp
                260                 265                 270

Val Leu Leu Gln Arg Cys Glu Gly Gly Val Asp Ala Ala Leu Leu Tyr
            275                 280                 285

Ala Lys Asn Met Ala Lys Tyr Met Lys Asp Leu Ile Ser Tyr Leu Glu
        290                 295                 300

Lys Arg Thr Thr Leu Glu Met Glu Phe Ala Lys Gly Leu Gln Lys Ile
305                 310                 315                 320

Ala His Asn Cys Arg Gln Ser Val Met Gln Glu Pro His Met Pro Leu
                325                 330                 335

Leu Ser Ile Tyr Ser Leu Ala Leu Glu Gln Asp Leu Glu Phe Gly His
                340                 345                 350

Ser Met Val Gln Ala Val Gly Thr Leu Gln Thr Gln Thr Phe Met Gln
            355                 360                 365

Pro Leu Thr Leu Arg Arg Leu Glu His Glu Lys Arg Arg Lys Glu Ile
        370                 375                 380

Lys Glu Ala Trp His Arg Ala Gln Arg Lys Leu Gln Glu Ala Glu Ser
385                 390                 395                 400

Asn Leu Arg Lys Ala Lys Gln Gly Tyr Val Gln Arg Cys Glu Asp His
                405                 410                 415

Asp Lys Ala Arg Phe Leu Val Ala Lys Ala Glu Glu Glu Gln Ala Gly
                420                 425                 430

Ser Ala Pro Gly Ala Gly Ser Thr Ala Thr Lys Thr Leu Asp Lys Arg
            435                 440                 445

Arg Arg Leu Glu Glu Glu Ala Lys Asn Lys Ala Glu Glu Ala Met Ala
        450                 455                 460

Thr Tyr Arg Thr Cys Val Ala Asp Ala Lys Thr Gln Lys Gln Glu Leu
465                 470                 475                 480

Glu Asp Thr Lys Val Thr Ala Leu Arg Gln Ile Gln Glu Val Ile Arg
                485                 490                 495

Gln Ser Asp Gln Thr Ile Lys Ser Ala Thr Ile Ser Tyr Tyr Gln Met
                500                 505                 510

Met His Met Gln Thr Ala Pro Leu Pro Val His Phe Gln Met Leu Cys
            515                 520                 525
```

```
Glu Ser Ser Lys Leu Tyr Asp Pro Gly Gln Gln Tyr Ala Ser His Val
    530                 535                 540

Arg Gln Leu Gln Arg Asp Gln Glu Pro Asp Val His Tyr Asp Phe Glu
545                 550                 555                 560

Pro His Val Ser Ala Asn Ala Trp Ser Pro Val Met Arg Ala Arg Lys
                565                 570                 575

Ser Ser Phe Asn Val Ser Asp Val Ala Arg Pro Glu Ala Ala Gly Ser
            580                 585                 590

Pro Pro Glu Glu Gly Gly Cys Thr Glu Gly Thr Pro Ala Lys Asp His
        595                 600                 605

Arg Ala Gly Arg Gly His Gln Val His Lys Ser Trp Pro Leu Ser Ile
    610                 615                 620

Ser Asp Ser Asp Ser Gly Leu Asp Pro Gly Pro Gly Ala Gly Asp Phe
625                 630                 635                 640

Lys Lys Phe Glu Arg Thr Ser Ser Ser Gly Thr Met Ser Ser Thr Glu
                645                 650                 655

Glu Leu Val Asp Pro Asp Gly Gly Ala Gly Ala Ser Ala Phe Glu Gln
            660                 665                 670

Ala Asp Leu Asn Gly Met Thr Pro Glu Leu Pro Val Ala Val Pro Ser
        675                 680                 685

Gly Pro Phe Arg His Glu Gly Leu Ser Lys Ala Ala Arg Thr His Arg
    690                 695                 700

Leu Arg Lys Leu Arg Thr Pro Ala Lys Cys Arg Glu Cys Asn Ser Tyr
705                 710                 715                 720

Val Tyr Phe Gln Gly Ala Glu Cys Glu Glu Cys Cys Leu Ala Cys His
                725                 730                 735

Lys Lys Cys Leu Glu Thr Leu Ala Ile Gln Cys Gly His Lys Lys Leu
            740                 745                 750

Gln Gly Arg Leu Gln Leu Phe Gly Gln Asp Phe Ser His Ala Ala Arg
        755                 760                 765

Ser Ala Pro Asp Gly Val Pro Phe Ile Val Lys Lys Cys Val Cys Glu
    770                 775                 780

Ile Glu Arg Arg Ala Leu Arg Thr Lys Gly Ile Tyr Arg Val Asn Gly
785                 790                 795                 800

Val Lys Thr Arg Val Glu Lys Leu Cys Gln Ala Phe Glu Asn Gly Lys
                805                 810                 815

Glu Leu Val Glu Leu Ser Gln Ala Ser Pro His Asp Ile Ser Asn Val
            820                 825                 830

Leu Lys Leu Tyr Leu Arg Gln Leu Pro Glu Pro Leu Ile Ser Phe Arg
        835                 840                 845

Leu Tyr His Glu Leu Val Gly Leu Ala Lys Asp Ser Leu Lys Ala Glu
    850                 855                 860

Ala Glu Ala Lys Ala Ala Ser Arg Gly Arg Gln Asp Gly Ser Glu Ser
865                 870                 875                 880

Glu Ala Val Ala Val Ala Leu Ala Gly Arg Leu Arg Glu Leu Leu Arg
                885                 890                 895

Asp Leu Pro Pro Glu Asn Arg Ala Ser Leu Gln Tyr Leu Leu Arg His
            900                 905                 910

Leu Arg Arg Ile Val Glu Val Glu Gln Asp Asn Lys Met Thr Pro Gly
        915                 920                 925

Asn Leu Gly Ile Val Phe Gly Pro Thr Leu Leu Arg Pro Arg Pro Thr
    930                 935                 940

Glu Ala Thr Val Ser Leu Ser Ser Leu Val Asp Tyr Pro His Gln Ala
```

```
                945                 950                 955                 960
Arg Val Ile Glu Thr Leu Ile Val His Tyr Gly Leu Val Phe Glu Glu
                    965                 970                 975
Glu Pro Glu Glu Thr Pro Gly Gly Gln Asp Glu Ser Ser Asn Gln Arg
                980                 985                 990
Ala Glu Val Val Val Gln Val Pro Tyr Leu Glu Ala Gly Glu Ala Val
                    995                 1000                1005
Val Tyr Pro Leu Gln Glu Ala Ala Asp Gly Cys Arg Glu Ser
    1010                1015                1020
Arg Val Val Ser Asn Asp Ser Asp Ser Asp Leu Glu Glu Ala Ser
    1025                1030                1035
Glu Leu Leu Ser Ser Ser Glu Ala Ser Ala Leu Gly His Leu Ser
    1040                1045                1050
Phe Leu Glu Gln Gln Gln Ser Glu Ala Ser Leu Glu Val Ala Ser
    1055                1060                1065
Gly Ser His Ser Gly Ser Glu Gln Leu Glu Ala Thr Ala Arg
    1070                1075                1080
Glu Asp Gly Asp Gly Asp Glu Asp Gly Pro Ala Gln Gln Leu Ser
    1085                1090                1095
Gly Phe Asn Thr Asn Gln Ser Asn Asn Val Leu Gln Ala Pro Leu
    1100                1105                1110
Pro Pro Met Arg Leu Arg Gly Gly Arg Met Thr Leu Gly Ser Cys
    1115                1120                1125
Arg Glu Arg Gln Pro Glu Phe Val
    1130                1135

<210> SEQ ID NO 2
<211> LENGTH: 9
<212> TYPE: PRT
<213> ORGANISM: Homo sapiens

<400> SEQUENCE: 2

Val Leu His Asp Asp Leu Leu Glu Ala
1               5

<210> SEQ ID NO 3
<211> LENGTH: 1136
<212> TYPE: PRT
<213> ORGANISM: Homo sapiens

<400> SEQUENCE: 3

Met Phe Ser Arg Lys Lys Arg Glu Leu Met Lys Thr Pro Ser Ile Ser
1               5                   10                  15
Lys Lys Asn Arg Ala Gly Ser Pro Ser Pro Gln Pro Ser Gly Glu Leu
                20                  25                  30
Pro Arg Lys Asp Gly Ala Asp Ala Val Phe Pro Gly Pro Ser Leu Glu
            35                  40                  45
Pro Pro Ala Gly Ser Ser Gly Val Lys Ala Thr Gly Thr Leu Lys Arg
        50                  55                  60
Pro Thr Ser Leu Ser Arg His Ala Ser Ala Ala Gly Phe Pro Leu Ser
65                  70                  75                  80
Gly Ala Ala Ser Trp Thr Leu Gly Arg Ser His Arg Ser Pro Leu Thr
                85                  90                  95
Ala Ala Ser Pro Gly Glu Leu Pro Thr Glu Gly Ala Gly Pro Asp Val
            100                 105                 110
Val Glu Asp Ile Ser His Leu Leu Ala Asp Val Ala Arg Phe Ala Glu
```

-continued

```
            115                 120                 125
Gly Leu Glu Lys Leu Lys Glu Cys Val Leu Arg Asp Asp Leu Leu Glu
    130                 135                 140

Ala Arg Arg Pro Arg Ala His Glu Cys Leu Gly Glu Ala Leu Arg Val
145                 150                 155                 160

Met His Gln Ile Ile Ser Lys Tyr Pro Leu Asn Thr Val Glu Thr
                165                 170                 175

Leu Thr Ala Ala Gly Thr Leu Ile Ala Lys Val Lys Ala Phe His Tyr
            180                 185                 190

Glu Ser Asn Asn Asp Leu Glu Lys Gln Glu Phe Glu Lys Ala Leu Glu
                195                 200                 205

Thr Ile Ala Val Ala Phe Ser Ser Thr Val Ser Glu Phe Leu Met Gly
    210                 215                 220

Glu Val Asp Ser Ser Thr Leu Leu Ala Val Pro Pro Gly Asp Ser Ser
225                 230                 235                 240

Gln Ser Met Glu Ser Leu Tyr Gly Pro Gly Ser Glu Gly Thr Pro Pro
                245                 250                 255

Ser Leu Glu Asp Cys Asp Ala Gly Cys Leu Pro Ala Glu Glu Val Asp
            260                 265                 270

Val Leu Leu Gln Arg Cys Glu Gly Val Asp Ala Ala Leu Leu Tyr
    275                 280                 285

Ala Lys Asn Met Ala Lys Tyr Met Lys Asp Leu Ile Ser Tyr Leu Glu
290                 295                 300

Lys Arg Thr Thr Leu Glu Met Glu Phe Ala Lys Gly Leu Gln Lys Ile
305                 310                 315                 320

Ala His Asn Cys Arg Gln Ser Val Met Gln Glu Pro His Met Pro Leu
                325                 330                 335

Leu Ser Ile Tyr Ser Leu Ala Leu Glu Gln Asp Leu Glu Phe Gly His
            340                 345                 350

Ser Met Val Gln Ala Val Gly Thr Leu Gln Thr Gln Thr Phe Met Gln
    355                 360                 365

Pro Leu Thr Leu Arg Arg Leu Glu His Glu Lys Arg Arg Lys Glu Ile
370                 375                 380

Lys Glu Ala Trp His Arg Ala Gln Arg Lys Leu Gln Glu Ala Glu Ser
385                 390                 395                 400

Asn Leu Arg Lys Ala Lys Gln Gly Tyr Val Gln Arg Cys Glu Asp His
                405                 410                 415

Asp Lys Ala Arg Phe Leu Val Ala Lys Ala Glu Glu Gln Ala Gly
            420                 425                 430

Ser Ala Pro Gly Ala Gly Ser Thr Ala Thr Lys Thr Leu Asp Lys Arg
    435                 440                 445

Arg Arg Leu Glu Glu Glu Ala Lys Asn Lys Ala Glu Glu Ala Met Ala
450                 455                 460

Thr Tyr Arg Thr Cys Val Ala Asp Ala Lys Thr Gln Lys Gln Glu Leu
465                 470                 475                 480

Glu Asp Thr Lys Val Thr Ala Leu Arg Gln Ile Gln Glu Val Ile Arg
                485                 490                 495

Gln Ser Asp Gln Thr Ile Lys Ser Ala Thr Ile Ser Tyr Tyr Gln Met
            500                 505                 510

Met His Met Gln Thr Ala Pro Leu Pro Val His Phe Gln Met Leu Cys
    515                 520                 525

Glu Ser Ser Lys Leu Tyr Asp Pro Gly Gln Gln Tyr Ala Ser His Val
530                 535                 540
```

```
Arg Gln Leu Gln Arg Asp Gln Glu Pro Asp Val His Tyr Asp Phe Glu
545                 550                 555                 560

Pro His Val Ser Ala Asn Ala Trp Ser Pro Val Met Arg Ala Arg Lys
                565                 570                 575

Ser Ser Phe Asn Val Ser Asp Val Ala Arg Pro Glu Ala Ala Gly Ser
            580                 585                 590

Pro Pro Glu Glu Gly Gly Cys Thr Glu Gly Thr Pro Ala Lys Asp His
        595                 600                 605

Arg Ala Gly Arg Gly His Gln Val His Lys Ser Trp Pro Leu Ser Ile
610                 615                 620

Ser Asp Ser Asp Ser Gly Leu Asp Pro Gly Pro Gly Ala Gly Asp Phe
625                 630                 635                 640

Lys Lys Phe Glu Arg Thr Ser Ser Ser Gly Thr Met Ser Ser Thr Glu
                645                 650                 655

Glu Leu Val Asp Pro Asp Gly Ala Gly Ala Ser Ala Phe Glu Gln
                660                 665                 670

Ala Asp Leu Asn Gly Met Thr Pro Glu Leu Pro Val Ala Val Pro Ser
            675                 680                 685

Gly Pro Phe Arg His Glu Gly Leu Ser Lys Ala Ala Arg Thr His Arg
690                 695                 700

Leu Arg Lys Leu Arg Thr Pro Ala Lys Cys Arg Glu Cys Asn Ser Tyr
705                 710                 715                 720

Val Tyr Phe Gln Gly Ala Glu Cys Glu Glu Cys Leu Ala Cys His
                725                 730                 735

Lys Lys Cys Leu Glu Thr Leu Ala Ile Gln Cys Gly His Lys Lys Leu
            740                 745                 750

Gln Gly Arg Leu Gln Leu Phe Gly Gln Asp Phe Ser His Ala Ala Arg
            755                 760                 765

Ser Ala Pro Asp Gly Val Pro Phe Ile Val Lys Lys Cys Val Cys Glu
        770                 775                 780

Ile Glu Arg Arg Ala Leu Arg Thr Lys Gly Ile Tyr Arg Val Asn Gly
785                 790                 795                 800

Val Lys Thr Arg Val Glu Lys Leu Cys Gln Ala Phe Glu Asn Gly Lys
                805                 810                 815

Glu Leu Val Glu Leu Ser Gln Ala Ser Pro His Asp Ile Ser Asn Val
                820                 825                 830

Leu Lys Leu Tyr Leu Arg Gln Leu Pro Glu Pro Leu Ile Ser Phe Arg
            835                 840                 845

Leu Tyr His Glu Leu Val Gly Leu Ala Lys Asp Ser Leu Lys Ala Glu
            850                 855                 860

Ala Glu Ala Lys Ala Ala Ser Arg Gly Arg Gln Asp Gly Ser Glu Ser
865                 870                 875                 880

Glu Ala Val Ala Val Ala Leu Ala Gly Arg Leu Arg Glu Leu Leu Arg
                885                 890                 895

Asp Leu Pro Pro Glu Asn Arg Ala Ser Leu Gln Tyr Leu Leu Arg His
            900                 905                 910

Leu Arg Arg Ile Val Glu Val Glu Gln Asp Asn Lys Met Thr Pro Gly
            915                 920                 925

Asn Leu Gly Ile Val Phe Gly Pro Thr Leu Leu Arg Pro Arg Pro Thr
        930                 935                 940

Glu Ala Thr Val Ser Leu Ser Ser Leu Val Asp Tyr Pro His Gln Ala
945                 950                 955                 960
```

```
Arg Val Ile Glu Thr Leu Ile Val His Tyr Gly Leu Val Phe Glu Glu
            965                 970                 975

Glu Pro Glu Glu Thr Pro Gly Gly Gln Asp Glu Ser Ser Asn Gln Arg
            980                 985                 990

Ala Glu Val Val Gln Val Pro Tyr Leu Glu Ala Gly Glu Ala Val
        995                 1000                1005

Val Tyr Pro Leu Gln Glu Ala Ala Asp Gly Cys Arg Glu Ser
    1010                1015                1020

Arg Val Val Ser Asn Asp Ser Asp Ser Asp Leu Glu Glu Ala Ser
    1025                1030                1035

Glu Leu Leu Ser Ser Ser Glu Ala Ser Ala Leu Gly His Leu Ser
    1040                1045                1050

Phe Leu Glu Gln Gln Gln Ser Glu Ala Ser Leu Glu Val Ala Ser
    1055                1060                1065

Gly Ser His Ser Gly Ser Glu Glu Gln Leu Glu Ala Thr Ala Arg
    1070                1075                1080

Glu Asp Gly Asp Gly Asp Glu Asp Gly Pro Ala Gln Gln Leu Ser
    1085                1090                1095

Gly Phe Asn Thr Asn Gln Ser Asn Asn Val Leu Gln Ala Pro Leu
    1100                1105                1110

Pro Pro Met Arg Leu Arg Gly Gly Arg Met Thr Leu Gly Ser Cys
    1115                1120                1125

Arg Glu Arg Gln Pro Glu Phe Val
    1130                1135

<210> SEQ ID NO 4
<211> LENGTH: 9
<212> TYPE: PRT
<213> ORGANISM: Homo sapiens

<400> SEQUENCE: 4

Val Leu Arg Asp Asp Leu Leu Glu Ala
1               5

<210> SEQ ID NO 5
<211> LENGTH: 6
<212> TYPE: PRT
<213> ORGANISM: Homo sapiens

<400> SEQUENCE: 5

Asp Ser Ala Ser Asn Tyr
1               5

<210> SEQ ID NO 6
<211> LENGTH: 7
<212> TYPE: PRT
<213> ORGANISM: Homo sapiens

<400> SEQUENCE: 6

Ile Arg Ser Asn Val Gly Glu
1               5

<210> SEQ ID NO 7
<211> LENGTH: 8
<212> TYPE: PRT
<213> ORGANISM: Homo sapiens

<400> SEQUENCE: 7

Cys Ala Ala Ser Asp Leu Asn Phe
1               5
```

```
<210> SEQ ID NO 8
<211> LENGTH: 5
<212> TYPE: PRT
<213> ORGANISM: Homo sapiens

<400> SEQUENCE: 8

Ser Glu His Asn Arg
1               5

<210> SEQ ID NO 9
<211> LENGTH: 6
<212> TYPE: PRT
<213> ORGANISM: Homo sapiens

<400> SEQUENCE: 9

Phe Gln Asn Glu Ala Gln
1               5

<210> SEQ ID NO 10
<211> LENGTH: 14
<212> TYPE: PRT
<213> ORGANISM: Homo sapiens

<400> SEQUENCE: 10

Cys Ala Ser Ser Leu Val Ser Arg Val Asp Gly Tyr Thr Phe
1               5                   10

<210> SEQ ID NO 11
<211> LENGTH: 127
<212> TYPE: PRT
<213> ORGANISM: Homo sapiens

<400> SEQUENCE: 11

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Gly Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Ser
            100                 105                 110

Asp Leu Asn Phe Gly Lys Gly Thr Ser Leu Leu Val Thr Pro His
        115                 120                 125

<210> SEQ ID NO 12
<211> LENGTH: 134
<212> TYPE: PRT
<213> ORGANISM: Homo sapiens

<400> SEQUENCE: 12

Met Gly Thr Ser Leu Leu Cys Trp Met Ala Leu Cys Leu Leu Gly Ala
1               5                   10                  15

Asp His Ala Asp Thr Gly Val Ser Gln Asn Pro Arg His Lys Ile Thr
            20                  25                  30
```

```
Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
 50                  55                  60

Leu Thr Tyr Phe Gln Asn Glu Ala Gln Leu Glu Lys Ser Arg Leu Leu
 65                  70                  75                  80

Ser Asp Arg Phe Ser Ala Glu Arg Pro Lys Gly Ser Phe Ser Thr Leu
                 85                  90                  95

Glu Ile Gln Arg Thr Glu Gln Gly Asp Ser Ala Met Tyr Leu Cys Ala
                100                 105                 110

Ser Ser Leu Val Ser Arg Val Asp Gly Tyr Thr Phe Gly Ser Gly Thr
            115                 120                 125

Arg Leu Thr Val Val Glu
        130
```

<210> SEQ ID NO 13
<211> LENGTH: 263
<212> TYPE: PRT
<213> ORGANISM: Artificial Sequence
<220> FEATURE:
<223> OTHER INFORMATION: Human with murinized constant region

<400> SEQUENCE: 13

```
Met Thr Ser Ile Arg Ala Val Phe Ile Phe Leu Trp Leu Gln Leu Asp
 1               5                  10                  15

Leu Val Asn Gly Glu Asn Val Glu Gln His Pro Ser Thr Leu Ser Val
                 20                  25                  30

Gln Glu Gly Asp Ser Ala Val Ile Lys Cys Thr Tyr Ser Asp Ser Ala
            35                  40                  45

Ser Asn Tyr Phe Pro Trp Tyr Lys Gln Glu Leu Gly Lys Gly Pro Gln
 50                  55                  60

Leu Ile Ile Asp Ile Arg Ser Asn Val Gly Glu Lys Lys Asp Gln Arg
 65                  70                  75                  80

Ile Ala Val Thr Leu Asn Lys Thr Ala Lys His Phe Ser Leu His Ile
                 85                  90                  95

Thr Glu Thr Gln Pro Glu Asp Ser Ala Val Tyr Phe Cys Ala Ala Ser
            100                 105                 110

Asp Leu Asn Phe Gly Lys Gly Thr Ser Leu Leu Val Thr Pro His Ile
            115                 120                 125

Gln Asn Pro Glu Pro Ala Val Tyr Gln Leu Lys Asp Pro Arg Ser Gln
        130                 135                 140

Asp Ser Thr Leu Cys Leu Phe Thr Asp Phe Asp Ser Gln Ile Asn Val
145                 150                 155                 160

Pro Lys Thr Met Glu Ser Gly Thr Phe Ile Thr Asp Lys Thr Val Leu
                165                 170                 175

Asp Met Lys Ala Met Asp Ser Lys Ser Asn Gly Ala Ile Ala Trp Ser
            180                 185                 190

Asn Gln Thr Ser Phe Thr Cys Gln Asp Ile Phe Lys Glu Thr Asn Ala
        195                 200                 205

Thr Tyr Pro Ser Ser Asp Val Pro Cys Asp Ala Thr Leu Thr Glu Lys
    210                 215                 220

Ser Phe Glu Thr Asp Met Asn Leu Asn Phe Gln Asn Leu Ser Val Met
225                 230                 235                 240

Gly Leu Arg Ile Leu Leu Leu Lys Val Ala Gly Phe Asn Leu Leu Met
                245                 250                 255
```

```
Thr Leu Arg Leu Trp Ser Ser
            260

<210> SEQ ID NO 14
<211> LENGTH: 306
<212> TYPE: PRT
<213> ORGANISM: Artificial Sequence
<220> FEATURE:
<223> OTHER INFORMATION: Human with murinized constant region

<400> SEQUENCE: 14

Met Gly Thr Ser Leu Leu Cys Trp Met Ala Leu Cys Leu Leu Gly Ala
1               5                   10                  15

Asp His Ala Asp Thr Gly Val Ser Gln Asn Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Leu Val Ser Arg Val Asp Gly Tyr Thr Phe Gly Ser Gly Thr
        115                 120                 125

Arg Leu Thr Val Val Glu Asp Leu Arg Asn Val Thr Pro Pro Lys Val
    130                 135                 140

Thr Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
    210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr His Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Gly Leu Val Leu Met Ala Met Val Lys Lys Lys
    290                 295                 300

Asn Ser
305

<210> SEQ ID NO 15
<211> LENGTH: 6
<212> TYPE: PRT
<213> ORGANISM: Homo sapiens
```

```
<400> SEQUENCE: 15

Asp Ser Ala Ser Asn Tyr
1               5

<210> SEQ ID NO 16
<211> LENGTH: 7
<212> TYPE: PRT
<213> ORGANISM: Homo sapiens

<400> SEQUENCE: 16

Ile Arg Ser Asn Val Gly Glu
1               5

<210> SEQ ID NO 17
<211> LENGTH: 13
<212> TYPE: PRT
<213> ORGANISM: Homo sapiens

<400> SEQUENCE: 17

Cys Ala Ala His Thr Pro Gly Tyr Ser Thr Leu Thr Phe
1               5                   10

<210> SEQ ID NO 18
<211> LENGTH: 5
<212> TYPE: PRT
<213> ORGANISM: Homo sapiens

<400> SEQUENCE: 18

Ser Glu His Asn Arg
1               5

<210> SEQ ID NO 19
<211> LENGTH: 6
<212> TYPE: PRT
<213> ORGANISM: Homo sapiens

<400> SEQUENCE: 19

Phe Gln Asn Glu Ala Gln
1               5

<210> SEQ ID NO 20
<211> LENGTH: 14
<212> TYPE: PRT
<213> ORGANISM: Homo sapiens

<400> SEQUENCE: 20

Cys Ala Ser Ser Pro Arg Ala Gly Gly Glu Thr Gln Tyr Phe
1               5                   10

<210> SEQ ID NO 21
<211> LENGTH: 132
<212> TYPE: PRT
<213> ORGANISM: Homo sapiens

<400> SEQUENCE: 21

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
                20                  25                  30

Gln Glu Gly Asp Ser Ala Val Ile Lys Cys Thr Tyr Ser Asp Ser Ala
            35                  40                  45

Ser Asn Tyr Phe Pro Trp Tyr Lys Gln Glu Leu Gly Lys Gly Pro Gln
```

```
                50                  55                  60
Leu Ile Ile Asp Ile Arg Ser Asn Val Gly Glu Lys Lys Asp Gln Arg
 65                  70                  75                  80

Ile Ala Val Thr Leu Asn Lys Thr Ala Lys His Phe Ser Leu His Ile
                 85                  90                  95

Thr Glu Thr Gln Pro Glu Asp Ser Ala Val Tyr Phe Cys Ala Ala His
                100                 105                 110

Thr Pro Gly Tyr Ser Thr Leu Thr Phe Gly Lys Gly Thr Met Leu Leu
                115                 120                 125

Val Ser Pro Asp
        130

<210> SEQ ID NO 22
<211> LENGTH: 134
<212> TYPE: PRT
<213> ORGANISM: Homo sapiens

<400> SEQUENCE: 22

Met Gly Thr Ser Leu Leu Cys Trp Met Ala Leu Cys Leu Leu Gly Ala
  1               5                  10                  15

Asp His Ala Asp Thr Gly Val Ser Gln Asn Pro Arg His Lys Ile Thr
                 20                  25                  30

Lys Arg Gly Gln Asn Val Thr Phe Arg Cys Asp Pro Ile Ser Glu His
             35                  40                  45

Asn Arg Leu Tyr Trp Tyr Arg Gln Thr Leu Gly Gln Gly Pro Glu Phe
         50                  55                  60

Leu Thr Tyr Phe Gln Asn Glu Ala Gln Leu Glu Lys Ser Arg Leu Leu
 65                  70                  75                  80

Ser Asp Arg Phe Ser Ala Glu Arg Pro Lys Gly Ser Phe Ser Thr Leu
                 85                  90                  95

Glu Ile Gln Arg Thr Glu Gln Gly Asp Ser Ala Met Tyr Leu Cys Ala
                100                 105                 110

Ser Ser Pro Arg Ala Gly Gly Glu Thr Gln Tyr Phe Gly Pro Gly Thr
                115                 120                 125

Arg Leu Leu Val Leu Glu
        130

<210> SEQ ID NO 23
<211> LENGTH: 268
<212> TYPE: PRT
<213> ORGANISM: Artificial Sequence
<220> FEATURE:
<223> OTHER INFORMATION: Human with murinized constant region

<400> SEQUENCE: 23

Met Thr Ser Ile Arg Ala Val Phe Ile Phe Leu Trp Leu Gln Leu Asp
  1               5                  10                  15

Leu Val Asn Gly Glu Asn Val Glu Gln His Pro Ser Thr Leu Ser Val
                 20                  25                  30

Gln Glu Gly Asp Ser Ala Val Ile Lys Cys Thr Tyr Ser Asp Ser Ala
             35                  40                  45

Ser Asn Tyr Phe Pro Trp Tyr Lys Gln Glu Leu Gly Lys Gly Pro Gln
         50                  55                  60

Leu Ile Ile Asp Ile Arg Ser Asn Val Gly Glu Lys Lys Asp Gln Arg
 65                  70                  75                  80

Ile Ala Val Thr Leu Asn Lys Thr Ala Lys His Phe Ser Leu His Ile
                 85                  90                  95
```

```
Thr Glu Thr Gln Pro Glu Asp Ser Ala Val Tyr Phe Cys Ala Ala His
            100                 105                 110

Thr Pro Gly Tyr Ser Thr Leu Thr Phe Gly Lys Gly Thr Met Leu Leu
            115                 120                 125

Val Ser Pro Asp Ile Gln Asn Pro Glu Pro Ala Val Tyr Gln Leu Lys
130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
            195                 200                 205

Lys Glu Thr Asn Ala Thr Tyr Pro Ser Ser Asp Val Pro Cys Asp Ala
210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Leu Lys Val Ala Gly
                245                 250                 255

Phe Asn Leu Leu Met Thr Leu Arg Leu Trp Ser Ser
                260                 265

<210> SEQ ID NO 24
<211> LENGTH: 306
<212> TYPE: PRT
<213> ORGANISM: Artificial Sequence
<220> FEATURE:
<223> OTHER INFORMATION: Human with murinized constant region

<400> SEQUENCE: 24

Met Gly Thr Ser Leu Leu Cys Trp Met Ala Leu Cys Leu Leu Gly Ala
1               5                   10                  15

Asp His Ala Asp Thr Gly Val Ser Gln Asn Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Pro Arg Ala Gly Gly Glu Thr Gln Tyr Phe Gly Pro Gly Thr
            115                 120                 125

Arg Leu Leu Val Leu Glu Asp Leu Arg Asn Val Thr Pro Pro Lys Val
130                 135                 140

Thr Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Ser Thr Asp
            180                 185                 190
```

```
            Pro Gln Ala Tyr Lys Glu Ser Asn Tyr Ser Tyr Cys Leu Ser Ser Arg
                    195                 200                 205

Leu Arg Val Ser Ala Thr Phe Trp His Asn Pro Arg Asn His Phe Arg
                210                 215                 220

Cys Gln Val Gln Phe His Gly Leu Ser Glu Glu Asp Lys Trp Pro Glu
            225                 230                 235                 240

Gly Ser Pro Lys Pro Val Thr Gln Asn Ile Ser Ala Glu Ala Trp Gly
                            245                 250                 255

Arg Ala Asp Cys Gly Ile Thr Ser Ala Ser Tyr His Gln Gly Val Leu
                        260                 265                 270

Ser Ala Thr Ile Leu Tyr Glu Ile Leu Leu Gly Lys Ala Thr Leu Tyr
                    275                 280                 285

Ala Val Leu Val Ser Gly Leu Val Leu Met Ala Met Val Lys Lys Lys
                290                 295                 300

Asn Ser
            305

<210> SEQ ID NO 25
            <211> LENGTH: 5
            <212> TYPE: PRT
            <213> ORGANISM: Homo sapiens

<400> SEQUENCE: 25

Thr Ser Ile Asn Asn
            1               5

<210> SEQ ID NO 26
            <211> LENGTH: 7
            <212> TYPE: PRT
            <213> ORGANISM: Homo sapiens

<400> SEQUENCE: 26

Ile Arg Ser Asn Glu Arg Glu
            1               5

<210> SEQ ID NO 27
            <211> LENGTH: 14
            <212> TYPE: PRT
            <213> ORGANISM: Homo sapiens

<400> SEQUENCE: 27

Cys Ala Thr Gly Asp Gln Thr Gly Ala Asn Asn Leu Phe Phe
            1               5                   10

<210> SEQ ID NO 28
            <211> LENGTH: 5
            <212> TYPE: PRT
            <213> ORGANISM: Homo sapiens

<400> SEQUENCE: 28

Ser Glu His Asn Arg
            1               5

<210> SEQ ID NO 29
            <211> LENGTH: 6
            <212> TYPE: PRT
            <213> ORGANISM: Homo sapiens

<400> SEQUENCE: 29

Phe Gln Asn Glu Ala Gln
            1               5
```

<210> SEQ ID NO 30
<211> LENGTH: 13
<212> TYPE: PRT
<213> ORGANISM: Homo sapiens

<400> SEQUENCE: 30

Cys Ala Ser Ser Leu Thr Arg Thr Glu Lys Leu Phe Phe
1               5                   10

<210> SEQ ID NO 31
<211> LENGTH: 133
<212> TYPE: PRT
<213> ORGANISM: Homo sapiens

<400> SEQUENCE: 31

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Leu Leu Ile
                85                  90                  95

Thr Ala Ser Arg Ala Ala Asp Thr Ala Ser Tyr Phe Cys Ala Thr Gly
                100                 105                 110

Asp Gln Thr Gly Ala Asn Asn Leu Phe Phe Gly Thr Gly Thr Arg Leu
            115                 120                 125

Thr Val Ile Pro Tyr
        130

<210> SEQ ID NO 32
<211> LENGTH: 133
<212> TYPE: PRT
<213> ORGANISM: Homo sapiens

<400> SEQUENCE: 32

Met Gly Thr Ser Leu Leu Cys Trp Met Ala Leu Cys Leu Leu Gly Ala
1               5                   10                  15

Asp His Ala Asp Thr Gly Val Ser Gln Asn Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
                100                 105                 110

Ser Ser Leu Thr Arg Thr Glu Lys Leu Phe Phe Gly Ser Gly Thr Gln
            115                 120                 125

Leu Ser Val Leu Glu
    130

<210> SEQ ID NO 33
<211> LENGTH: 269
<212> TYPE: PRT
<213> ORGANISM: Artificial Sequence
<220> FEATURE:
<223> OTHER INFORMATION: Human with murinized constant region

<400> SEQUENCE: 33

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Ser Leu Leu Ile
                85                  90                  95

Thr Ala Ser Arg Ala Ala Asp Thr Ala Ser Tyr Phe Cys Ala Thr Gly
            100                 105                 110

Asp Gln Thr Gly Ala Asn Asn Leu Phe Phe Gly Thr Gly Thr Arg Leu
        115                 120                 125

Thr Val Ile Pro Tyr Ile Gln Asn Pro Glu Pro Ala Val Tyr Gln Leu
    130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175

Thr Asp Lys Thr Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
        195                 200                 205

Phe Lys Glu Thr Asn Ala Thr Tyr Pro Ser Ser Asp Val Pro Cys Asp
    210                 215                 220

Ala Thr Leu Thr Glu Lys Ser Phe Glu Thr Asp Met Asn Leu Asn Phe
225                 230                 235                 240

Gln Asn Leu Ser Val Met Gly Leu Arg Ile Leu Leu Leu Lys Val Ala
                245                 250                 255

Gly Phe Asn Leu Leu Met Thr Leu Arg Leu Trp Ser Ser
            260                 265

<210> SEQ ID NO 34
<211> LENGTH: 305
<212> TYPE: PRT
<213> ORGANISM: Artificial Sequence
<220> FEATURE:
<223> OTHER INFORMATION: Human with murinized constant region

<400> SEQUENCE: 34

Met Gly Thr Ser Leu Leu Cys Trp Met Ala Leu Cys Leu Leu Gly Ala
1               5                   10                  15

Asp His Ala Asp Thr Gly Val Ser Gln Asn Pro Arg His Lys Ile Thr
            20                  25                  30

```
Lys Arg Gly Gln Asn Val Thr Phe Arg Cys Asp Pro Ile Ser Glu His
        35                  40                  45
Asn Arg Leu Tyr Trp Tyr Arg Gln Thr Leu Gly Gln Gly Pro Glu Phe
 50                  55                  60
Leu Thr Tyr Phe Gln Asn Glu Ala Gln Leu Glu Lys Ser Arg Leu Leu
 65                  70                  75                  80
Ser Asp Arg Phe Ser Ala Glu Arg Pro Lys Gly Ser Phe Ser Thr Leu
                 85                  90                  95
Glu Ile Gln Arg Thr Glu Gln Gly Asp Ser Ala Met Tyr Leu Cys Ala
             100                 105                 110
Ser Ser Leu Thr Arg Thr Glu Lys Leu Phe Phe Gly Ser Gly Thr Gln
         115                 120                 125
Leu Ser Val Leu Glu Asp Leu Arg Asn Val Thr Pro Pro Lys Val Thr
     130                 135                 140
Leu Phe Glu Pro Ser Lys Ala Glu Ile Ala Asn Lys Gln Lys Ala Thr
145                 150                 155                 160
Leu Val Cys Leu Ala Arg Gly Phe Phe Pro Asp His Val Glu Leu Ser
                 165                 170                 175
Trp Trp Val Asn Gly Lys Glu Val His Ser Gly Val Ser Thr Asp Pro
             180                 185                 190
Gln Ala Tyr Lys Glu Ser Asn Tyr Ser Tyr Cys Leu Ser Ser Arg Leu
         195                 200                 205
Arg Val Ser Ala Thr Phe Trp His Asn Pro Arg Asn His Phe Arg Cys
     210                 215                 220
Gln Val Gln Phe His Gly Leu Ser Glu Glu Asp Lys Trp Pro Glu Gly
225                 230                 235                 240
Ser Pro Lys Pro Val Thr Gln Asn Ile Ser Ala Glu Ala Trp Gly Arg
                 245                 250                 255
Ala Asp Cys Gly Ile Thr Ser Ala Ser Tyr His Gln Gly Val Leu Ser
             260                 265                 270
Ala Thr Ile Leu Tyr Glu Ile Leu Leu Gly Lys Ala Thr Leu Tyr Ala
         275                 280                 285
Val Leu Val Ser Gly Leu Val Leu Met Ala Met Val Lys Lys Lys Asn
     290                 295                 300
Ser
305

<210> SEQ ID NO 35
<211> LENGTH: 6
<212> TYPE: PRT
<213> ORGANISM: Homo sapiens

<400> SEQUENCE: 35

Asp Ser Ala Ser Asn Tyr
1               5

<210> SEQ ID NO 36
<211> LENGTH: 7
<212> TYPE: PRT
<213> ORGANISM: Homo sapiens

<400> SEQUENCE: 36

Ile Arg Ser Asn Val Gly Glu
1               5

<210> SEQ ID NO 37
```

```
<211> LENGTH: 9
<212> TYPE: PRT
<213> ORGANISM: Homo sapiens

<400> SEQUENCE: 37

Cys Ala Gly Arg Gly Lys Leu Thr Phe
1               5

<210> SEQ ID NO 38
<211> LENGTH: 5
<212> TYPE: PRT
<213> ORGANISM: Homo sapiens

<400> SEQUENCE: 38

Ser Glu His Asn Arg
1               5

<210> SEQ ID NO 39
<211> LENGTH: 6
<212> TYPE: PRT
<213> ORGANISM: Homo sapiens

<400> SEQUENCE: 39

Phe Gln Asn Glu Ala Gln
1               5

<210> SEQ ID NO 40
<211> LENGTH: 13
<212> TYPE: PRT
<213> ORGANISM: Homo sapiens

<400> SEQUENCE: 40

Cys Ala Ser Ser Leu Val Arg Asp Glu Lys Leu Phe Phe
1               5                   10

<210> SEQ ID NO 41
<211> LENGTH: 128
<212> TYPE: PRT
<213> ORGANISM: Homo sapiens

<400> SEQUENCE: 41

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
                20                  25                  30

Gln Glu Gly Asp Ser Ala Val Ile Lys Cys Thr Tyr Ser Asp Ser Ala
            35                  40                  45

Ser Asn Tyr Phe Pro Trp Tyr Lys Gln Glu Leu Gly Lys Gly Pro Gln
        50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Gly Arg
            100                 105                 110

Gly Lys Leu Thr Phe Gly Thr Gly Thr Arg Leu Thr Ile Ile Pro Asn
        115                 120                 125

<210> SEQ ID NO 42
<211> LENGTH: 133
<212> TYPE: PRT
<213> ORGANISM: Homo sapiens
```

<400> SEQUENCE: 42

Met Gly Thr Ser Leu Leu Cys Trp Met Ala Leu Cys Leu Leu Gly Ala
1               5                   10                  15

Asp His Ala Asp Thr Gly Val Ser Gln Asn Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Leu Val Arg Asp Glu Lys Leu Phe Phe Gly Ser Gly Thr Gln
        115                 120                 125

Leu Ser Val Leu Glu
    130

<210> SEQ ID NO 43
<211> LENGTH: 264
<212> TYPE: PRT
<213> ORGANISM: Artificial Sequence
<220> FEATURE:
<223> OTHER INFORMATION: Human with murinized constant region

<400> SEQUENCE: 43

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Gly Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Gly Arg
            100                 105                 110

Gly Lys Leu Thr Phe Gly Thr Gly Thr Arg Leu Thr Ile Ile Pro Asn
        115                 120                 125

Ile Gln Asn Pro Glu Pro Ala Val Tyr Gln Leu Lys Asp Pro Arg Ser
    130                 135                 140

Gln Asp Ser Thr Leu Cys Leu Phe Thr Asp Phe Asp Ser Gln Ile Asn
145                 150                 155                 160

Val Pro Lys Thr Met Glu Ser Gly Thr Phe Ile Thr Asp Lys Thr Val
                165                 170                 175

Leu Asp Met Lys Ala Met Asp Ser Lys Ser Asn Gly Ala Ile Ala Trp
            180                 185                 190

Ser Asn Gln Thr Ser Phe Thr Cys Gln Asp Ile Phe Lys Glu Thr Asn
        195                 200                 205

```
Ala Thr Tyr Pro Ser Ser Asp Val Pro Cys Asp Ala Thr Leu Thr Glu
    210                 215                 220

Lys Ser Phe Glu Thr Asp Met Asn Leu Asn Phe Gln Asn Leu Ser Val
225                 230                 235                 240

Met Gly Leu Arg Ile Leu Leu Lys Val Ala Gly Phe Asn Leu Leu
                245                 250                 255

Met Thr Leu Arg Leu Trp Ser Ser
                260

<210> SEQ ID NO 44
<211> LENGTH: 305
<212> TYPE: PRT
<213> ORGANISM: Artificial Sequence
<220> FEATURE:
<223> OTHER INFORMATION: Human with murinized constant region

<400> SEQUENCE: 44

Met Gly Thr Ser Leu Leu Cys Trp Met Ala Leu Cys Leu Leu Gly Ala
1               5                   10                  15

Asp His Ala Asp Thr Gly Val Ser Gln Asn Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Leu Val Arg Asp Glu Lys Leu Phe Phe Gly Ser Gly Thr Gln
        115                 120                 125

Leu Ser Val Leu Glu Asp Leu Arg Asn Val Thr Pro Pro Lys Val Thr
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr His Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Gly Leu Val Leu Met Ala Met Val Lys Lys Lys Asn
    290                 295                 300
```

Ser
305

<210> SEQ ID NO 45
<211> LENGTH: 5
<212> TYPE: PRT
<213> ORGANISM: Homo sapiens

<400> SEQUENCE: 45

Ser Val Phe Ser Ser
1               5

<210> SEQ ID NO 46
<211> LENGTH: 7
<212> TYPE: PRT
<213> ORGANISM: Homo sapiens

<400> SEQUENCE: 46

Val Val Thr Gly Gly Glu Val
1               5

<210> SEQ ID NO 47
<211> LENGTH: 11
<212> TYPE: PRT
<213> ORGANISM: Homo sapiens

<400> SEQUENCE: 47

Cys Ala Gly Ala Gly Asn Asn Asp Met Arg Phe
1               5                   10

<210> SEQ ID NO 48
<211> LENGTH: 5
<212> TYPE: PRT
<213> ORGANISM: Homo sapiens

<400> SEQUENCE: 48

Ser Glu His Asn Arg
1               5

<210> SEQ ID NO 49
<211> LENGTH: 6
<212> TYPE: PRT
<213> ORGANISM: Homo sapiens

<400> SEQUENCE: 49

Phe Gln Asn Glu Ala Gln
1               5

<210> SEQ ID NO 50
<211> LENGTH: 13
<212> TYPE: PRT
<213> ORGANISM: Homo sapiens

<400> SEQUENCE: 50

Cys Ala Ser Ser Leu Val Arg Gly Ile Glu Ala Phe Phe
1               5                   10

<210> SEQ ID NO 51
<211> LENGTH: 128
<212> TYPE: PRT
<213> ORGANISM: Homo sapiens

<400> SEQUENCE: 51

Met Val Leu Lys Phe Ser Val Ser Ile Leu Trp Ile Gln Leu Ala Trp
1               5                   10                  15

Val Ser Thr Gln Leu Leu Glu Gln Ser Pro Gln Phe Leu Ser Ile Gln
            20                  25                  30

Glu Gly Glu Asn Leu Thr Val Tyr Cys Asn Ser Ser Val Phe Ser
            35                  40                  45

Ser Leu Gln Trp Tyr Arg Gln Glu Pro Gly Glu Gly Pro Val Leu Leu
 50                  55                  60

Val Thr Val Val Thr Gly Gly Glu Val Lys Lys Leu Lys Arg Leu Thr
 65                  70                  75                  80

Phe Gln Phe Gly Asp Ala Arg Lys Asp Ser Ser Leu His Ile Thr Ala
                 85                  90                  95

Ala Gln Thr Gly Asp Thr Gly Leu Tyr Leu Cys Ala Gly Ala Gly Asn
            100                 105                 110

Asn Asp Met Arg Phe Gly Ala Gly Thr Arg Leu Thr Val Lys Pro Asn
            115                 120                 125

<210> SEQ ID NO 52
<211> LENGTH: 133
<212> TYPE: PRT
<213> ORGANISM: Homo sapiens

<400> SEQUENCE: 52

Met Gly Thr Ser Leu Leu Cys Trp Met Ala Leu Cys Leu Leu Gly Ala
 1               5                  10                  15

Asp His Ala Asp Thr Gly Val Ser Gln Asn Pro Arg His Lys Ile Thr
            20                  25                  30

Lys Arg Gly Gln Asn Val Thr Phe Arg Cys Asp Pro Ile Ser Glu His
            35                  40                  45

Asn Arg Leu Tyr Trp Tyr Arg Gln Thr Leu Gly Gln Gly Pro Glu Phe
 50                  55                  60

Leu Thr Tyr Phe Gln Asn Glu Ala Gln Leu Glu Lys Ser Arg Leu Leu
 65                  70                  75                  80

Ser Asp Arg Phe Ser Ala Glu Arg Pro Lys Gly Ser Phe Ser Thr Leu
                 85                  90                  95

Glu Ile Gln Arg Thr Glu Gln Gly Asp Ser Ala Met Tyr Leu Cys Ala
            100                 105                 110

Ser Ser Leu Val Arg Gly Ile Glu Ala Phe Phe Gly Gln Gly Thr Arg
            115                 120                 125

Leu Thr Val Val Glu
            130

<210> SEQ ID NO 53
<211> LENGTH: 264
<212> TYPE: PRT
<213> ORGANISM: Artificial Sequence
<220> FEATURE:
<223> OTHER INFORMATION: Human with murinized constant region

<400> SEQUENCE: 53

Met Val Leu Lys Phe Ser Val Ser Ile Leu Trp Ile Gln Leu Ala Trp
 1               5                  10                  15

Val Ser Thr Gln Leu Leu Glu Gln Ser Pro Gln Phe Leu Ser Ile Gln
            20                  25                  30

Glu Gly Glu Asn Leu Thr Val Tyr Cys Asn Ser Ser Val Phe Ser
            35                  40                  45

Ser Leu Gln Trp Tyr Arg Gln Glu Pro Gly Glu Gly Pro Val Leu Leu
 50                  55                  60

Val Thr Val Val Thr Gly Gly Glu Val Lys Lys Leu Lys Arg Leu Thr
65                  70                  75                  80

Phe Gln Phe Gly Asp Ala Arg Lys Asp Ser Ser Leu His Ile Thr Ala
            85                  90                  95

Ala Gln Thr Gly Asp Thr Gly Leu Tyr Leu Cys Ala Gly Ala Gly Asn
            100                 105                 110

Asn Asp Met Arg Phe Gly Ala Gly Thr Arg Leu Thr Val Lys Pro Asn
            115                 120                 125

Ile Gln Asn Pro Glu Pro Ala Val Tyr Gln Leu Lys Asp Pro Arg Ser
            130                 135                 140

Gln Asp Ser Thr Leu Cys Leu Phe Thr Asp Phe Asp Ser Gln Ile Asn
145                 150                 155                 160

Val Pro Lys Thr Met Glu Ser Gly Thr Phe Ile Thr Asp Lys Thr Val
            165                 170                 175

Leu Asp Met Lys Ala Met Asp Ser Lys Ser Asn Gly Ala Ile Ala Trp
            180                 185                 190

Ser Asn Gln Thr Ser Phe Thr Cys Gln Asp Ile Phe Lys Glu Thr Asn
            195                 200                 205

Ala Thr Tyr Pro Ser Ser Asp Val Pro Cys Asp Ala Thr Leu Thr Glu
            210                 215                 220

Lys Ser Phe Glu Thr Asp Met Asn Leu Asn Phe Gln Asn Leu Ser Val
225                 230                 235                 240

Met Gly Leu Arg Ile Leu Leu Leu Lys Val Ala Gly Phe Asn Leu Leu
            245                 250                 255

Met Thr Leu Arg Leu Trp Ser Ser
            260

<210> SEQ ID NO 54
<211> LENGTH: 305
<212> TYPE: PRT
<213> ORGANISM: Artificial Sequence
<220> FEATURE:
<223> OTHER INFORMATION: Human with murinized constant region

<400> SEQUENCE: 54

Met Gly Thr Ser Leu Leu Cys Trp Met Ala Leu Cys Leu Leu Gly Ala
1               5                   10                  15

Asp His Ala Asp Thr Gly Val Ser Gln Asn Pro Arg His Lys Ile Thr
            20                  25                  30

Lys Arg Gly Gln Asn Val Thr Phe Arg Cys Asp Pro Ile Ser Glu His
            35                  40                  45

Asn Arg Leu Tyr Trp Tyr Arg Gln Thr Leu Gly Gln Gly Pro Glu Phe
        50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
            85                  90                  95

Glu Ile Gln Arg Thr Glu Gln Gly Asp Ser Ala Met Tyr Leu Cys Ala
            100                 105                 110

Ser Ser Leu Val Arg Gly Ile Glu Ala Phe Phe Gly Gln Gly Thr Arg
            115                 120                 125

Leu Thr Val Val Glu Asp Leu Arg Asn Val Thr Pro Pro Lys Val Thr
            130                 135                 140

Leu Phe Glu Pro Ser Lys Ala Glu Ile Ala Asn Lys Gln Lys Ala Thr
145                 150                 155                 160

-continued

```
Leu Val Cys Leu Ala Arg Gly Phe Phe Pro Asp His Val Glu Leu Ser
              165                 170                 175
Trp Trp Val Asn Gly Lys Glu Val His Ser Gly Val Ser Thr Asp Pro
          180                 185                 190
Gln Ala Tyr Lys Glu Ser Asn Tyr Ser Tyr Cys Leu Ser Ser Arg Leu
      195                 200                 205
Arg Val Ser Ala Thr Phe Trp His Asn Pro Arg Asn His Phe Arg Cys
  210                 215                 220
Gln Val Gln Phe His Gly Leu Ser Glu Glu Asp Lys Trp Pro Glu Gly
225                 230                 235                 240
Ser Pro Lys Pro Val Thr Gln Asn Ile Ser Ala Glu Ala Trp Gly Arg
              245                 250                 255
Ala Asp Cys Gly Ile Thr Ser Ala Ser Tyr His Gln Gly Val Leu Ser
          260                 265                 270
Ala Thr Ile Leu Tyr Glu Ile Leu Leu Gly Lys Ala Thr Leu Tyr Ala
      275                 280                 285
Val Leu Val Ser Gly Leu Val Leu Met Ala Met Val Lys Lys Lys Asn
  290                 295                 300
Ser
305

<210> SEQ ID NO 55
<211> LENGTH: 6
<212> TYPE: PRT
<213> ORGANISM: Homo sapiens

<400> SEQUENCE: 55

Asp Ser Ser Ser Thr Tyr
1               5

<210> SEQ ID NO 56
<211> LENGTH: 7
<212> TYPE: PRT
<213> ORGANISM: Homo sapiens

<400> SEQUENCE: 56

Ile Phe Ser Asn Met Asp Met
1               5

<210> SEQ ID NO 57
<211> LENGTH: 8
<212> TYPE: PRT
<213> ORGANISM: Homo sapiens

<400> SEQUENCE: 57

Cys Ala Glu Lys Trp Ile Ile Phe
1               5

<210> SEQ ID NO 58
<211> LENGTH: 5
<212> TYPE: PRT
<213> ORGANISM: Homo sapiens

<400> SEQUENCE: 58

Ser Glu His Asn Arg
1               5

<210> SEQ ID NO 59
<211> LENGTH: 6
<212> TYPE: PRT
<213> ORGANISM: Homo sapiens
```

<400> SEQUENCE: 59

Phe Gln Asn Glu Ala Gln
1               5

<210> SEQ ID NO 60
<211> LENGTH: 13
<212> TYPE: PRT
<213> ORGANISM: Homo sapiens

<400> SEQUENCE: 60

Cys Ala Ser Ser Leu Thr Thr Pro Asp Gly Tyr Thr Phe
1               5                   10

<210> SEQ ID NO 61
<211> LENGTH: 128
<212> TYPE: PRT
<213> ORGANISM: Homo sapiens

<400> SEQUENCE: 61

Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
            20                  25                  30

Val Arg Glu Gly Asp Ser Ser Val Ile Asn Cys Thr Tyr Thr Asp Ser
        35                  40                  45

Ser Ser Thr Tyr Leu Tyr Trp Tyr Lys Gln Glu Pro Gly Ala Gly Leu
    50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
            100                 105                 110

Lys Trp Ile Ile Phe Gly Lys Gly Thr Arg Leu His Ile Leu Pro Asn
        115                 120                 125

<210> SEQ ID NO 62
<211> LENGTH: 133
<212> TYPE: PRT
<213> ORGANISM: Homo sapiens

<400> SEQUENCE: 62

Met Gly Thr Ser Leu Leu Cys Trp Met Ala Leu Cys Leu Leu Gly Ala
1               5                   10                  15

Asp His Ala Asp Thr Gly Val Ser Gln Asn Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Leu Thr Thr Pro Asp Gly Tyr Thr Phe Gly Ser Gly Thr Arg

```
              115                 120                 125
Leu Thr Val Val Glu
            130

<210> SEQ ID NO 63
<211> LENGTH: 264
<212> TYPE: PRT
<213> ORGANISM: Artificial Sequence
<220> FEATURE:
<223> OTHER INFORMATION: Human with murinized constant region

<400> SEQUENCE: 63

Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
            20                  25                  30

Val Arg Glu Gly Asp Ser Ser Val Ile Asn Cys Thr Tyr Thr Asp Ser
        35                  40                  45

Ser Ser Thr Tyr Leu Tyr Trp Tyr Lys Gln Glu Pro Gly Ala Gly Leu
    50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
            100                 105                 110

Lys Trp Ile Ile Phe Gly Lys Gly Thr Arg Leu His Ile Leu Pro Asn
        115                 120                 125

Ile Gln Asn Pro Glu Pro Ala Val Tyr Gln Leu Lys Asp Pro Arg Ser
    130                 135                 140

Gln Asp Ser Thr Leu Cys Leu Phe Thr Asp Phe Asp Ser Gln Ile Asn
145                 150                 155                 160

Val Pro Lys Thr Met Glu Ser Gly Thr Phe Ile Thr Asp Lys Thr Val
                165                 170                 175

Leu Asp Met Lys Ala Met Asp Ser Lys Ser Asn Gly Ala Ile Ala Trp
            180                 185                 190

Ser Asn Gln Thr Ser Phe Thr Cys Gln Asp Ile Phe Lys Glu Thr Asn
        195                 200                 205

Ala Thr Tyr Pro Ser Ser Asp Val Pro Cys Asp Ala Thr Leu Thr Glu
    210                 215                 220

Lys Ser Phe Glu Thr Asp Met Asn Leu Asn Phe Gln Asn Leu Ser Val
225                 230                 235                 240

Met Gly Leu Arg Ile Leu Leu Leu Lys Val Ala Gly Phe Asn Leu Leu
                245                 250                 255

Met Thr Leu Arg Leu Trp Ser Ser
            260

<210> SEQ ID NO 64
<211> LENGTH: 305
<212> TYPE: PRT
<213> ORGANISM: Artificial Sequence
<220> FEATURE:
<223> OTHER INFORMATION: Human with murinized constant region

<400> SEQUENCE: 64

Met Gly Thr Ser Leu Leu Cys Trp Met Ala Leu Cys Leu Leu Gly Ala
1               5                   10                  15
```

-continued

```
Asp His Ala Asp Thr Gly Val Ser Gln Asn Pro Arg His Lys Ile Thr
             20                  25                  30

Lys Arg Gly Gln Asn Val Thr Phe Arg Cys Asp Pro Ile Ser Glu His
         35                  40                  45

Asn Arg Leu Tyr Trp Tyr Arg Gln Thr Leu Gly Gln Gly Pro Glu Phe
     50                  55                  60

Leu Thr Tyr Phe Gln Asn Glu Ala Gln Leu Glu Lys Ser Arg Leu Leu
 65                  70                  75                  80

Ser Asp Arg Phe Ser Ala Glu Arg Pro Lys Gly Ser Phe Ser Thr Leu
                 85                  90                  95

Glu Ile Gln Arg Thr Glu Gln Gly Asp Ser Ala Met Tyr Leu Cys Ala
            100                 105                 110

Ser Ser Leu Thr Thr Pro Asp Gly Tyr Thr Phe Gly Ser Gly Thr Arg
        115                 120                 125

Leu Thr Val Val Glu Asp Leu Arg Asn Val Thr Pro Pro Lys Val Thr
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr His Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Gly Leu Val Leu Met Ala Met Val Lys Lys Lys Asn
290                 295                 300

Ser
305

<210> SEQ ID NO 65
<211> LENGTH: 10
<212> TYPE: PRT
<213> ORGANISM: Artificial Sequence
<220> FEATURE:
<223> OTHER INFORMATION: Control Peptide Astn1 P1268L

<400> SEQUENCE: 65

Lys Leu Tyr Gly Leu Asp Trp Ala Glu Leu
1               5                   10

<210> SEQ ID NO 66
<211> LENGTH: 18
<212> TYPE: DNA
<213> ORGANISM: Artificial Sequence
<220> FEATURE:
<223> OTHER INFORMATION: Codon optimized sequence of homo sapiens

<400> SEQUENCE: 66
```

-continued gacagcgcca gcaactac                                           18

<210> SEQ ID NO 67
<211> LENGTH: 21
<212> TYPE: DNA
<213> ORGANISM: Artificial Sequence
<220> FEATURE:
<223> OTHER INFORMATION: Codon optimized sequence of homo sapiens

<400> SEQUENCE: 67
atcagatcca acgtgggcga g                                       21

<210> SEQ ID NO 68
<211> LENGTH: 24
<212> TYPE: DNA
<213> ORGANISM: Artificial Sequence
<220> FEATURE:
<223> OTHER INFORMATION: Codon optimized sequence of homo sapiens

<400> SEQUENCE: 68
tgcgccgcca gcgacctgaa tttt                                    24

<210> SEQ ID NO 69
<211> LENGTH: 15
<212> TYPE: DNA
<213> ORGANISM: Artificial Sequence
<220> FEATURE:
<223> OTHER INFORMATION: Codon optimized sequence of homo sapiens

<400> SEQUENCE: 69
agcgagcaca accgg                                              15

<210> SEQ ID NO 70
<211> LENGTH: 18
<212> TYPE: DNA
<213> ORGANISM: Artificial Sequence
<220> FEATURE:
<223> OTHER INFORMATION: Codon optimized sequence of homo sapiens

<400> SEQUENCE: 70
ttccagaacg aggcccag                                           18

<210> SEQ ID NO 71
<211> LENGTH: 42
<212> TYPE: DNA
<213> ORGANISM: Artificial Sequence
<220> FEATURE:
<223> OTHER INFORMATION: Codon optimized sequence of homo sapiens

<400> SEQUENCE: 71
tgtgccagca gcctggtgtc cagagtggat ggctacacat tt                42

<210> SEQ ID NO 72
<211> LENGTH: 379
<212> TYPE: DNA
<213> ORGANISM: Artificial Sequence
<220> FEATURE:
<223> OTHER INFORMATION: Codon optimized sequence of homo sapiens

<400> SEQUENCE: 72
atgaccagca tccgggccgt gttcatcttc ctgtggctgc agctggacct ggtcaacggc   60
gagaatgtgg aacagcaccc cagcacactg agcgtgcaag agggcgattc tgccgtgatc  120
aagtgcacct acagcgacag cgccagcaac tacttcccct ggtacaagca agaactcggc  180

```
aagggccctc agctgatcat cgacatcaga tccaacgtgg gcgagaagaa ggaccagcgg      240
attgccgtga cactgaacaa gaccgccaag cacttcagcc tgcacatcac cgagacacag      300
cctgaggata gcgccgtgta cttttgcgcc gccagcgacc tgaattttgg caagggcaca      360
agcctgctgg tcacccctc                                                  379

<210> SEQ ID NO 73
<211> LENGTH: 400
<212> TYPE: DNA
<213> ORGANISM: Artificial Sequence
<220> FEATURE:
<223> OTHER INFORMATION: Codon optimized sequence of homo sapiens

<400> SEQUENCE: 73
atgggcacaa gcctgctgtg ttggatggcc ctgtgtctgc tgggagccga tcatgccgat       60
acgggagtgt ctcagaaccc cagacacaag atcaccaagc ggggccagaa cgtgaccttc      120
agatgcgacc ctatcagcga gcacaaccgg ctgtactggt acagacagac actcggccag      180
ggacctgagt tcctgaccta cttccagaac gaggcccagc tggaaaagag cagactgctg      240
agcgacagat tcagcgccga aagacccaag ggcagcttca gcaccctgga aatccagaga      300
accgagcagg gcgacagcgc catgtatctg tgtgccagca gctggtgtc cagagtggat      360 ggctacacat ttggcagcgg caccagactg acagtggtgg                           400

<210> SEQ ID NO 74
<211> LENGTH: 792
<212> TYPE: DNA
<213> ORGANISM: Artificial Sequence
<220> FEATURE:
<223> OTHER INFORMATION: Human (codon optimized) with murinized constant
      region

<400> SEQUENCE: 74
atgaccagca tccgggccgt gttcatcttc ctgtggctgc agctggacct ggtcaacggc       60
gagaatgtgg aacagcaccc cagcacactg agcgtgcaag agggcgattc tgccgtgatc      120
aagtgcacct acagcgacag cgccagcaac tacttcccct ggtacaagca agaactcggc      180
aagggccctc agctgatcat cgacatcaga tccaacgtgg gcgagaagaa ggaccagcgg      240
attgccgtga cactgaacaa gaccgccaag cacttcagcc tgcacatcac cgagacacag      300
cctgaggata gcgccgtgta cttttgcgcc gccagcgacc tgaattttgg caagggcaca      360
agcctgctgg tcacccctca catccagaat ccggagcccg ccgtatacca gctgaaggac      420
cctagaagcc aggacagcac cctgtgcctg ttcaccgact cgacagcca gatcaacgtg      480 cccaagacca tggaaagcgg caccttcatc accgacaaga cagtgctgga catgaaggcc      540
atggacagca gtccaacgg cgcaatcgcc tggtccaacc agaccagctt cacatgccag      600
gacatcttca agagacaaa cgccacatac cccagcagcg acgtgccctg tgatgccacc      660
ctgacagaga agtccttcga cagacatg aacctgaact tccagaatct gtccgtgatg      720
ggcctgagaa tcctgctgct gaaggtggcc ggcttcaatc tgctgatgac cctgcggctg      780
tggtccagct ga                                                        792

<210> SEQ ID NO 75
<211> LENGTH: 921
<212> TYPE: DNA
<213> ORGANISM: Artificial Sequence
<220> FEATURE:
<223> OTHER INFORMATION: Human (codon optimized) with murinized constant
      region
```

<400> SEQUENCE: 75

| | | | | | |
|---|---|---|---|---|---|
| atgggcacaa | gcctgctgtg | ttggatggcc | ctgtgtctgc | tgggagccga | tcatgccgat | 60 |
| acgggagtgt | ctcagaaccc | cagacacaag | atcaccaagc | ggggccagaa | cgtgaccttc | 120 |
| agatgcgacc | ctatcagcga | gcacaaccgg | ctgtactggt | acagacagac | actcggccag | 180 |
| ggacctgagt | tcctgaccta | cttccagaac | gaggcccagc | tggaaaagag | cagactgctg | 240 |
| agcgacagat | tcagcgccga | aagacccaag | ggcagcttca | gcaccctgga | aatccagaga | 300 |
| accgagcagg | gcgacagcgc | catgtatctg | tgtgccagca | gcctggtgtc | cagagtggat | 360 |
| ggctacacat | ttggcagcgg | caccagactg | acagtggtgg | aagatctccg | gaacgtgacc | 420 |
| ccccctaaag | tgaccctgtt | cgaacccagc | aaggccgaga | tcgccaacaa | gcagaaagcc | 480 |
| accctcgtgt | gcctggccag | aggcttcttc | cccgaccatg | tggaactgtc | ttggtgggtc | 540 |
| aacggcaaag | aggtgcacag | cggagtgtcc | accgaccctc | aggcctacaa | agagagcaac | 600 |
| tacagctact | gcctgagcag | cagactgcgg | gtgtccgcca | ccttctggca | caacccccgg | 660 |
| aaccacttca | gatgccaggt | gcagtttcac | ggcctgagcg | aagaggacaa | gtggcccgaa | 720 |
| ggctccccca | gcccgtgac | ccagaatatc | tctgccgagg | cctggggcag | agccgactgt | 780 |
| ggaattacca | gcgccagcta | ccaccagggc | gtgctgtctg | ccaccatcct | gtacgagatc | 840 |
| ctgctgggca | aggccaccct | gtacgccgtg | ctggtgtctg | gcctggtgct | gatggccatg | 900 |
| gtcaagaaga | agaacagctg | a | | | | 921 |

<210> SEQ ID NO 76
<211> LENGTH: 18
<212> TYPE: DNA
<213> ORGANISM: Artificial Sequence
<220> FEATURE:
<223> OTHER INFORMATION: Codon optimized sequence of homo sapiens

<400> SEQUENCE: 76
gacagcgcca gcaactac                                                  18

<210> SEQ ID NO 77
<211> LENGTH: 21
<212> TYPE: DNA
<213> ORGANISM: Artificial Sequence
<220> FEATURE:
<223> OTHER INFORMATION: Codon optimized sequence of homo sapiens

<400> SEQUENCE: 77
atcagatcca acgtgggcga g                                              21

<210> SEQ ID NO 78
<211> LENGTH: 39
<212> TYPE: DNA
<213> ORGANISM: Artificial Sequence
<220> FEATURE:
<223> OTHER INFORMATION: Codon optimized sequence of homo sapiens

<400> SEQUENCE: 78
tgcgccgctc acacacctgg ctacagcacc ctgacattt                            39

<210> SEQ ID NO 79
<211> LENGTH: 15
<212> TYPE: DNA
<213> ORGANISM: Artificial Sequence
<220> FEATURE:
<223> OTHER INFORMATION: Codon optimized sequence of homo sapiens

<400> SEQUENCE: 79
agcgagcaca accgg    15

<210> SEQ ID NO 80
<211> LENGTH: 18
<212> TYPE: DNA
<213> ORGANISM: Artificial Sequence
<220> FEATURE:
<223> OTHER INFORMATION: Codon optimized sequence of homo sapiens

<400> SEQUENCE: 80
ttccagaacg aggcccag    18

<210> SEQ ID NO 81
<211> LENGTH: 42
<212> TYPE: DNA
<213> ORGANISM: Artificial Sequence
<220> FEATURE:
<223> OTHER INFORMATION: Codon optimized sequence of homo sapiens

<400> SEQUENCE: 81
tgtgctagct ctcctagagc cggcggagag acacagtatt tc    42

<210> SEQ ID NO 82
<211> LENGTH: 394
<212> TYPE: DNA
<213> ORGANISM: Artificial Sequence
<220> FEATURE:
<223> OTHER INFORMATION: Codon optimized sequence of homo sapiens

<400> SEQUENCE: 82
atgaccagca tccgggccgt gttcatcttc ctgtggctgc agctggacct ggtcaacggc    60
gagaatgtgg aacagcaccc cagcacactg agcgtgcaag agggcgattc tgccgtgatc    120
aagtgcacct acagcgacag cgccagcaac tacttcccct ggtacaagca agaactcggc    180
aagggccctc agctgatcat cgacatcaga tccaacgtgg gcgagaagaa ggaccagcgg    240
attgccgtga cactgaacaa gaccgccaag cacttcagcc tgcacatcac cgagacacag    300
cctgaggata cgcccgtgta cttctgcgcc gctcacacac ctggctacag caccctgaca    360
tttggcaagg gcaccatgct gctggtgtcc ccag    394

<210> SEQ ID NO 83
<211> LENGTH: 400
<212> TYPE: DNA
<213> ORGANISM: Artificial Sequence
<220> FEATURE:
<223> OTHER INFORMATION: Codon optimized sequence of homo sapiens

<400> SEQUENCE: 83
atgggcacaa gcctgctgtg ttggatggcc ctgtgtctgc tgggagccga tcatgccgat    60
acgggagtgt ctcagaaccc cagacacaag atcaccaagc ggggccagaa cgtgaccttc    120
agatgcgacc ctatcagcga gcacaaccgg ctgtactggt acagacagac actcggccag    180
ggacctgagt tcctgaccta cttccagaac gaggcccagc tggaaaagag cagactgctg    240
agcgacagat tcagcgccga aagacccaag ggcagcttca gcaccctgga aatccagaga    300
accgagcagg gcgacagcgc catgtacctg tgtgctagct ctcctagagc cggcggagag    360
acacagtatt tcggccctgg aacacggctg ctggttctgg    400

<210> SEQ ID NO 84
<211> LENGTH: 807

```
<212> TYPE: DNA
<213> ORGANISM: Artificial Sequence
<220> FEATURE:
<223> OTHER INFORMATION: Human (codon optimized) with murinized constant
      region

<400> SEQUENCE: 84
atgaccagca tccgggccgt gttcatcttc ctgtggctgc agctggacct ggtcaacggc      60
gagaatgtgg aacagcaccc cagcacactg agcgtgcaag agggcgattc tgccgtgatc     120
aagtgcacct acagcgacag cgccagcaac tacttcccct ggtacaagca agaactcggc     180
aagggccctc agctgatcat cgacatcaga tccaacgtgg cgagaagaa ggaccagcgg      240 attgccgtga cactgaacaa gaccgccaag cacttcagcc tgcacatcac cgagacacag     300
cctgaggata cgccgtgta cttctgcgcc gctcacacac ctggctacag caccctgaca      360
tttggcaagg gcaccatgct gctggtgtcc ccagacatcc agaatccgga gcccgccgta     420
taccagctga aggaccctag aagccaggac agcaccctgt gcctgttcac cgacttcgac     480
agccagatca acgtgcccaa gaccatggaa agcggcacct tcatcaccga caagacagtg     540
ctggacatga aggccatgga cagcaagtcc aacggcgcaa tcgcctggtc aaccagacc      600 agcttcacat gccaggacat cttcaaagag acaaacgcca catacccag cagcgacgtg      660 ccctgtgatg ccaccctgac agagaagtcc ttcgagacag acatgaacct gaacttccag     720
aatctgtccg tgatgggcct gagaatcctg ctgctgaagg tggccggctt caatctgctg     780
atgaccctgc ggctgtggtc cagctga                                         807

<210> SEQ ID NO 85
<211> LENGTH: 921
<212> TYPE: DNA
<213> ORGANISM: Artificial Sequence
<220> FEATURE:
<223> OTHER INFORMATION: Human (codon optimized) with murinized constant
      region

<400> SEQUENCE: 85
atgggcacaa gcctgctgtg ttggatggcc ctgtgtctgc tgggagccga tcatgccgat      60
acgggagtgt ctcagaaccc cagacacaag atcaccaagc ggggccagaa cgtgaccttc     120
agatgcgacc ctatcagcga gcacaaccgg ctgtactggt acagacagac actcggccag     180
ggacctgagt tcctgaccta cttccagaac gaggcccagc tggaaaagag cagactgctg     240
agcgacagat tcagcgccga aagacccaag ggcagcttca gcaccctgga aatccagaga     300
accgagcagg gcgacagcgc catgtacctg tgtgctagct tcctagagc cggcggagag      360 acacagtatt tcggccctgg aacacggctg ctggttctgg aagatctccg gaacgtgacc     420 cccctaaag tgaccctgtt cgaacccagc aaggccgaga tcgccaacaa gcagaaagcc      480
accctcgtgt gcctggccag aggcttcttc cccgaccatg tggaactgtc ttggtgggtc     540
aacggcaaag aggtgcacag cggagtgtcc accgaccctc aggcctacaa agagagcaac     600
tacagctact gcctgagcag cagactgcgg gtgtccgcca ccttctggca acccccgg       660 aaccacttca gatgccaggt gcagtttcac ggcctgagcg aagaggacaa gtggcccgaa     720
ggctccccca gcccgtgac ccagaatatc tctgccgagg cctggggcag agccgactgt      780
ggaattacca gcgccagcta ccaccagggc gtgctgtctg ccaccatcct gtacgagatc     840
ctgctgggca aggccaccct gtacgccgtg ctggtgtctg gcctggtgct gatggccatg     900
gtcaagaaga agaacagctg a                                               921
```

<210> SEQ ID NO 86
<211> LENGTH: 15
<212> TYPE: DNA
<213> ORGANISM: Artificial Sequence
<220> FEATURE:
<223> OTHER INFORMATION: Codon optimized sequence of homo sapiens

<400> SEQUENCE: 86
accagcatca acaac                                                    15

<210> SEQ ID NO 87
<211> LENGTH: 21
<212> TYPE: DNA
<213> ORGANISM: Artificial Sequence
<220> FEATURE:
<223> OTHER INFORMATION: Codon optimized sequence of homo sapiens

<400> SEQUENCE: 87
atcagaagca acgagagaga g                                             21

<210> SEQ ID NO 88
<211> LENGTH: 42
<212> TYPE: DNA
<213> ORGANISM: Artificial Sequence
<220> FEATURE:
<223> OTHER INFORMATION: Codon optimized sequence of homo sapiens

<400> SEQUENCE: 88
tgcgccactg gcgatcagac cggcgccaac aatctgttct tt                      42

<210> SEQ ID NO 89
<211> LENGTH: 15
<212> TYPE: DNA
<213> ORGANISM: Artificial Sequence
<220> FEATURE:
<223> OTHER INFORMATION: Codon optimized sequence of homo sapiens

<400> SEQUENCE: 89
agcgagcaca accgg                                                    15

<210> SEQ ID NO 90
<211> LENGTH: 18
<212> TYPE: DNA
<213> ORGANISM: Artificial Sequence
<220> FEATURE:
<223> OTHER INFORMATION: Codon optimized sequence of homo sapiens

<400> SEQUENCE: 90
ttccagaacg aggcccag                                                 18

<210> SEQ ID NO 91
<211> LENGTH: 39
<212> TYPE: DNA
<213> ORGANISM: Artificial Sequence
<220> FEATURE:
<223> OTHER INFORMATION: Codon optimized sequence of homo sapiens

<400> SEQUENCE: 91
tgtgccagca gcctgaccag aaccgagaag ctgttttc                           39

<210> SEQ ID NO 92
<211> LENGTH: 397
<212> TYPE: DNA
<213> ORGANISM: Artificial Sequence
<220> FEATURE:
<223> OTHER INFORMATION: Codon optimized sequence of homo sapiens

<400> SEQUENCE: 92

| | |
|---|---|
| atggaaacac tgctgggcgt gtccctggtc atcctgtggc tgcaactggc cagagtgaac | 60 |
| agccagcagg gcgaagaaga tccccaggct ctgtctatcc aagagggcga gaacgccacc | 120 |
| atgaactgca gctacaagac cagcatcaac aacctgcagt ggtacagaca aacagcggc | 180 |
| agaggactgg tgcacctgat cctgatcaga agcaacgaga gagagaagca ctccggcaga | 240 |
| ctgagagtga ccctggacac cagcaagaag tccagcagcc tgctgatcac cgcctctaga | 300 |
| gctgccgata ccgccagcta cttttgcgcc actggcgatc agaccggcgc caacaatctg | 360 |
| ttctttggca ccggaaccag gctgacagtg atcccctt | 397 |

<210> SEQ ID NO 93
<211> LENGTH: 397
<212> TYPE: DNA
<213> ORGANISM: Artificial Sequence
<220> FEATURE:
<223> OTHER INFORMATION: Codon optimized sequence of homo sapiens

<400> SEQUENCE: 93

| | |
|---|---|
| atgggcacaa gcctgctgtg ttggatggcc ctgtgtctgc tgggagccga tcatgccgat | 60 |
| acgggagtgt ctcagaaccc cagacacaag atcaccaagc ggggccagaa cgtgaccttc | 120 |
| agatgcgacc ctatcagcga gcacaaccgg ctgtactggt acagacagac actcggccag | 180 |
| ggacctgagt tcctgaccta cttccagaac gaggcccagc tggaaaagag cagactgctg | 240 |
| agcgacagat tcagcgccga aagacccaag ggcagcttca gcaccctgga aatccagaga | 300 |
| accgagcagg gcgacagcgc catgtatctg tgtgccagca gcctgaccag aaccgagaag | 360 |
| ctgtttttcg gcagcggcac ccagctgtct gttctgg | 397 |

<210> SEQ ID NO 94
<211> LENGTH: 810
<212> TYPE: DNA
<213> ORGANISM: Artificial Sequence
<220> FEATURE:
<223> OTHER INFORMATION: Human (codon optimized) with murinized constant region

<400> SEQUENCE: 94

| | |
|---|---|
| atggaaacac tgctgggcgt gtccctggtc atcctgtggc tgcaactggc cagagtgaac | 60 |
| agccagcagg gcgaagaaga tccccaggct ctgtctatcc aagagggcga gaacgccacc | 120 |
| atgaactgca gctacaagac cagcatcaac aacctgcagt ggtacagaca aacagcggc | 180 |
| agaggactgg tgcacctgat cctgatcaga agcaacgaga gagagaagca ctccggcaga | 240 |
| ctgagagtga ccctggacac cagcaagaag tccagcagcc tgctgatcac cgcctctaga | 300 |
| gctgccgata ccgccagcta cttttgcgcc actggcgatc agaccggcgc caacaatctg | 360 |
| ttctttggca ccggaaccag gctgacagtg atcccttaca tccagaatcc ggagcccgcc | 420 |
| gtataccagc tgaaggaccc tagaagccag gacagcaccc tgtgcctgtt caccgacttc | 480 |
| gacagccaga tcaacgtgcc caagaccatg gaaagcggca ccttcatcac cgacaagaca | 540 |
| gtgctggaca tgaaggccat ggacagcaag tccaacggcg caatcgcctg gtccaaccag | 600 |
| accagcttca tgccaggaca tcttcaaa gagacaaacg ccacataccc cagcagcgac | 660 |
| gtgccctgtg atgccaccct gacagagaag tccttcgaga cagacatgaa cctgaacttc | 720 |
| cagaatctgt ccgtgatggg cctgagaatc ctgctgctga aggtggccgg cttcaatctg | 780 |
| ctgatgaccc tgcggctgtg gtccagctga | 810 |

<210> SEQ ID NO 95
<211> LENGTH: 918
<212> TYPE: DNA
<213> ORGANISM: Artificial Sequence
<220> FEATURE:
<223> OTHER INFORMATION: Human (codon optimized) with murinized constant
      region

<400> SEQUENCE: 95
atgggcacaa gcctgctgtg ttggatggcc ctgtgtctgc tgggagccga tcatgccgat    60
acgggagtgt ctcagaaccc cagacacaag atcaccaagc ggggccagaa cgtgaccttc   120
agatgcgacc ctatcagcga gcacaaccgg ctgtactggt acagacagac actcggccag   180
ggacctgagt tcctgaccta cttccagaac gaggcccagc tggaaaagag cagactgctg   240
agcgacagat tcagcgccga aagacccaag ggcagcttca gcaccctgga aatccagaga   300
accgagcagg gcgacagcgc catgtatctg tgtgccagca gcctgaccag aaccgagaag   360
ctgtttttcg gcagcggcac ccagctgtct gttctggaag atctccggaa cgtgaccccc   420
cctaaagtga ccctgttcga acccagcaag gccgagatcg ccaacaagca gaaagccacc   480
ctcgtgtgcc tggccagagg cttcttcccc gaccatgtgg aactgtcttg gtgggtcaac   540
ggcaaagagg tgcacagcgg agtgtccacc gaccctcagg cctacaaaga gagcaactac   600
agctactgcc tgagcagcag actgcgggtg tccgccacct tctggacaaa cccccggaac   660
cacttcagat gccaggtgca gtttcacggc ctgagcgaag aggacaagtg gccgaaggc    720 tccccccaagc ccgtgaccca gaatatctct gccgaggcct ggggcagagc cgactgtgga   780
attaccagcg ccagctacca ccagggcgtg ctgtctgcca ccatcctgta cgagatcctg   840
ctgggcaagg ccaccctgta cgccgtgctg gtgtctggcc tggtgctgat ggccatggtc   900
aagaagaaga acagctga                                                918

<210> SEQ ID NO 96
<211> LENGTH: 18
<212> TYPE: DNA
<213> ORGANISM: Artificial Sequence
<220> FEATURE:
<223> OTHER INFORMATION: Codon optimized sequence of homo sapiens

<400> SEQUENCE: 96
gacagcgcca gcaactac                                                 18

<210> SEQ ID NO 97
<211> LENGTH: 21
<212> TYPE: DNA
<213> ORGANISM: Artificial Sequence
<220> FEATURE:
<223> OTHER INFORMATION: Codon optimized sequence of homo sapiens

<400> SEQUENCE: 97
atcagatcca acgtgggcga g                                             21

<210> SEQ ID NO 98
<211> LENGTH: 27
<212> TYPE: DNA
<213> ORGANISM: Artificial Sequence
<220> FEATURE:
<223> OTHER INFORMATION: Codon optimized sequence of homo sapiens

<400> SEQUENCE: 98
tgtgccggca gaggcaagct gacctttt                                      27

<210> SEQ ID NO 99
<211> LENGTH: 15
<212> TYPE: DNA
<213> ORGANISM: Artificial Sequence
<220> FEATURE:
<223> OTHER INFORMATION: Codon optimized sequence of homo sapiens

<400> SEQUENCE: 99
agcgagcaca accgg                                                     15

<210> SEQ ID NO 100
<211> LENGTH: 18
<212> TYPE: DNA
<213> ORGANISM: Artificial Sequence
<220> FEATURE:
<223> OTHER INFORMATION: Codon optimized sequence of homo sapiens

<400> SEQUENCE: 100
ttccagaacg aggcccag                                                  18

<210> SEQ ID NO 101
<211> LENGTH: 39
<212> TYPE: DNA
<213> ORGANISM: Artificial Sequence
<220> FEATURE:
<223> OTHER INFORMATION: Codon optimized sequence of homo sapiens

<400> SEQUENCE: 101
tgtgccagtt ctctcgtgcg ggacgagaag ctgttttttc                          39

<210> SEQ ID NO 102
<211> LENGTH: 382
<212> TYPE: DNA
<213> ORGANISM: Artificial Sequence
<220> FEATURE:
<223> OTHER INFORMATION: Codon optimized sequence of homo sapiens

<400> SEQUENCE: 102
atgaccagca tccgggccgt gttcatcttc ctgtggctgc agctggacct ggtcaacggc    60
gagaatgtgg aacagcaccc cagcacactg agcgtgcaag agggcgattc tgccgtgatc   120
aagtgcacct acagcgacag cgccagcaac tacttcccct ggtacaagca agaactcggc   180
aagggccctc agctgatcat cgacatcaga tccaacgtgg cgagaagaa ggaccagcgg   240 attgccgtga cactgaacaa gaccgccaag cacttcagcc tgcacatcac cgagacacag   300
cctgaggata gcgccgtgta cttctgtgcc ggcagaggca agctgacctt tggcacaggc   360
acccggctga caatcatccc ta                                            382

<210> SEQ ID NO 103
<211> LENGTH: 397
<212> TYPE: DNA
<213> ORGANISM: Artificial Sequence
<220> FEATURE:
<223> OTHER INFORMATION: Codon optimized sequence of homo sapiens

<400> SEQUENCE: 103
atgggcacaa gcctgctgtg ttggatggcc ctgtgtctgc tgggagccga tcatgccgat    60
acgggagtgt ctcagaaccc cagacacaag atcaccaagc ggggccagaa cgtgaccttc   120
agatgcgacc ctatcagcga gcacaaccgg ctgtactggt acagcagac actcggccag   180 ggacctgagt tcctgaccta cttccagaac gaggcccagc tggaaaagag cagactgctg   240

| | |
|---|---|
| agcgacagat tcagcgccga aagacccaag ggcagcttca gcaccctgga aatccagaga | 300 |
| accgagcagg gcgacagcgc catgtatctg tgtgccagtt ctctcgtgcg ggacgagaag | 360 |
| ctgttttcg gcagcggcac acagctgagc gttctgg | 397 |

<210> SEQ ID NO 104
<211> LENGTH: 795
<212> TYPE: DNA
<213> ORGANISM: Artificial Sequence
<220> FEATURE:
<223> OTHER INFORMATION: Human (codon optimized) with murinized constant region

<400> SEQUENCE: 104

| | |
|---|---|
| atgaccagca tccgggccgt gttcatcttc ctgtggctgc agctggacct ggtcaacggc | 60 |
| gagaatgtgg aacagcaccc cagcacactg agcgtgcaag agggcgattc tgccgtgatc | 120 |
| aagtgcacct acagcgacag cgccagcaac tacttcccct ggtacaagca agaactcggc | 180 |
| aagggccctc agctgatcat cgacatcaga tccaacgtgg gcgagaagaa ggaccagcgg | 240 |
| attgccgtga cactgaacaa gaccgccaag cacttcagcc tgcacatcac cgagacacag | 300 |
| cctgaggata gcgccgtgta cttctgtgcc ggcagaggca agctgacctt ggcacaggc | 360 |
| acccggctga caatcatccc taacatccag aatccggagc ccgccgtata ccagctgaag | 420 |
| gaccctagaa gccaggacag caccctgtgc ctgttcaccg acttcgacag ccagatcaac | 480 |
| gtgcccaaga ccatggaaag cggcaccttc atcaccgaca gacagtgct ggacatgaag | 540 |
| gccatggaca gcaagtccaa cggcgcaatc gcctggtcca accagaccag cttcacatgc | 600 |
| caggacatct tcaaagagac aaacgccaca taccccagca gcgacgtgcc ctgtgatgcc | 660 |
| accctgacag agaagtcctt cgagacagac atgaacctga acttccagaa tctgtccgtg | 720 |
| atgggcctga gaatcctgct gctgaaggtg gccggcttca atctgctgat gaccctgcgg | 780 |
| ctgtggtcca gctga | 795 |

<210> SEQ ID NO 105
<211> LENGTH: 918
<212> TYPE: DNA
<213> ORGANISM: Artificial Sequence
<220> FEATURE:
<223> OTHER INFORMATION: Human (codon omptimized) with murinized constant region

<400> SEQUENCE: 105

| | |
|---|---|
| atgggcacaa gcctgctgtg ttggatggcc ctgtgtctgc tgggagccga tcatgccgat | 60 |
| acgggagtgt ctcagaaccc cagacacaag atcaccaagc ggggccagaa cgtgaccttc | 120 |
| agatgcgacc ctatcagcga gcacaaccgg ctgtactggt acagacagac actcggccag | 180 |
| ggacctgagt tcctgaccta cttccagaac gaggcccagc tggaaaagag cagactgctg | 240 |
| agcgacagat tcagcgccga aagacccaag ggcagcttca gcaccctgga aatccagaga | 300 |
| accgagcagg gcgacagcgc catgtatctg tgtgccagtt ctctcgtgcg ggacgagaag | 360 |
| ctgttttcg gcagcggcac acagctgagc gttctggaag atctccggaa cgtgaccccc | 420 |
| cctaaagtga ccctgttcga acccagcaag gccgagatcg ccaacaagca gaaagccacc | 480 |
| ctcgtgtgcc tggccagagg cttcttcccc gaccatgtgg aactgtcttg gtgggtcaac | 540 |
| ggcaaagagg tgcacagcgg agtgtccacc gaccctcagg cctacaaaga gagcaactac | 600 |
| agctactgcc tgagcagcag actgcgggtg tccgccacct tctggcacaa ccccggaac | 660 |
| cacttcagat gccaggtgca gtttcacggc ctgagcgaag aggacaagtg gcccgaaggc | 720 |

```
tcccccaagc ccgtgaccca gaatatctct gccgaggcct ggggcagagc cgactgtgga    780
attaccagcg ccagctacca ccagggcgtg ctgtctgcca ccatcctgta cgagatcctg    840
ctgggcaagg ccaccctgta cgccgtgctg gtgtctggcc tggtgctgat ggccatggtc    900
aagaagaaga acagctga                                                  918

<210> SEQ ID NO 106
<211> LENGTH: 15
<212> TYPE: DNA
<213> ORGANISM: Artificial Sequence
<220> FEATURE:
<223> OTHER INFORMATION: Codon optimized sequence of homo sapiens

<400> SEQUENCE: 106
agcgtgttca gcagc                                                      15

<210> SEQ ID NO 107
<211> LENGTH: 21
<212> TYPE: DNA
<213> ORGANISM: Artificial Sequence
<220> FEATURE:
<223> OTHER INFORMATION: Codon optimized sequence of homo sapiens

<400> SEQUENCE: 107
gttgtgacag gcggcgaagt g                                               21

<210> SEQ ID NO 108
<211> LENGTH: 33
<212> TYPE: DNA
<213> ORGANISM: Artificial Sequence
<220> FEATURE:
<223> OTHER INFORMATION: Codon optimized sequence of homo sapiens

<400> SEQUENCE: 108
tgtgccggcg ctggcaacaa cgacatgaga ttt                                  33

<210> SEQ ID NO 109
<211> LENGTH: 15
<212> TYPE: DNA
<213> ORGANISM: Artificial Sequence
<220> FEATURE:
<223> OTHER INFORMATION: Codon optimized sequence of homo sapiens

<400> SEQUENCE: 109
agcgagcaca accgg                                                      15

<210> SEQ ID NO 110
<211> LENGTH: 18
<212> TYPE: DNA
<213> ORGANISM: Artificial Sequence
<220> FEATURE:
<223> OTHER INFORMATION: Codon optimized sequence of homo sapiens

<400> SEQUENCE: 110
ttccagaacg aggcccag                                                   18

<210> SEQ ID NO 111
<211> LENGTH: 39
<212> TYPE: DNA
<213> ORGANISM: Artificial Sequence
<220> FEATURE:
<223> OTHER INFORMATION: Codon optimized sequence of homo sapiens

<400> SEQUENCE: 111
```

```
tgtgcctctt ctctcgtgcg gggcatcgag gccttttttt                          39
```

<210> SEQ ID NO 112
<211> LENGTH: 382
<212> TYPE: DNA
<213> ORGANISM: Artificial Sequence
<220> FEATURE:
<223> OTHER INFORMATION: Codon optimized sequence of homo sapiens

<400> SEQUENCE: 112

```
atggtgctga agttcagcgt gtccatcctg tggatccagc tggcctgggt ttccacacag    60
ctgctggaac agagccctca gttcctgagc atccaagagg gcgagaacct gaccgtgtac   120
tgcaacagca gcagcgtgtt cagcagcctg cagtggtaca gacaagagcc tggcgaagga   180
cctgtgctgc tggtcacagt tgtgacaggc ggcgaagtga agaagctgaa gcggctgacc   240
ttccagttcg gcgacgccag aaaggatagc tccctgcaca ttaccgccgc tcagacaggc   300
gataccggcc tgtatctttg tgccggcgct ggcaacaacg acatgagatt tggcgccgga   360
accagactga ccgtgaagcc ta                                            382
```

<210> SEQ ID NO 113
<211> LENGTH: 397
<212> TYPE: DNA
<213> ORGANISM: Artificial Sequence
<220> FEATURE:
<223> OTHER INFORMATION: Codon optimized sequence of homo sapiens

<400> SEQUENCE: 113

```
atgggcacaa gcctgctgtg ttggatggcc ctgtgtctgc tgggagccga tcatgccgat    60
acgggagtgt ctcagaaccc cagacacaag atcaccaagc ggggccagaa cgtgaccttc   120
agatgcgacc ctatcagcga gcacaaccgg ctgtactggt acagacagac actcggccag   180
ggacctgagt tcctgaccta cttccagaac gaggcccagc tggaaaagag cagactgctg   240
agcgacagat tcagcgccga aagacccaag ggcagcttca gcaccctgga aatccagaga   300
accgagcagg gcgacagcgc catgtatctg tgtgcctctt ctctcgtgcg gggcatcgag   360
gccttttttg gccaaggcac cagactgacc gtggtgg                            397
```

<210> SEQ ID NO 114
<211> LENGTH: 795
<212> TYPE: DNA
<213> ORGANISM: Artificial Sequence
<220> FEATURE:
<223> OTHER INFORMATION: Human (codon optimized) with murinized constant
      region

<400> SEQUENCE: 114

```
atggtgctga agttcagcgt gtccatcctg tggatccagc tggcctgggt ttccacacag    60
ctgctggaac agagccctca gttcctgagc atccaagagg gcgagaacct gaccgtgtac   120
tgcaacagca gcagcgtgtt cagcagcctg cagtggtaca gacaagagcc tggcgaagga   180
cctgtgctgc tggtcacagt tgtgacaggc ggcgaagtga agaagctgaa gcggctgacc   240
ttccagttcg gcgacgccag aaaggatagc tccctgcaca ttaccgccgc tcagacaggc   300
gataccggcc tgtatctttg tgccggcgct ggcaacaacg acatgagatt tggcgccgga   360
accagactga ccgtgaagcc taacatccag aatccggagc ccgccgtata ccagctgaag   420
gaccctagaa gccaggacag cacccgtgtc ctgttcaccg acttcgacag ccagatcaac   480
gtgcccaaga ccatggaaag cggcaccttc atcaccgaca gacagtgct ggacatgaag   540
```

```
gccatggaca gcaagtccaa cggcgcaatc gcctggtcca accagaccag cttcacatgc    600
caggacatct tcaaagagac aaacgccaca tacccagca gcgacgtgcc ctgtgatgcc      660
accctgacag agaagtcctt cgagacagac atgaacctga acttccagaa tctgtccgtg    720
atgggcctga aatcctgct gctgaaggtg gccggcttca atctgctgat gaccctgcgg      780
ctgtggtcca gctga                                                     795
```

```
<210> SEQ ID NO 115
<211> LENGTH: 918
<212> TYPE: DNA
<213> ORGANISM: Artificial Sequence
<220> FEATURE:
<223> OTHER INFORMATION: Human (codon opimized) with murinized constant
      region

<400> SEQUENCE: 115
atgggcacaa gcctgctgtg ttggatggcc ctgtgtctgc tgggagccga tcatgccgat     60
acgggagtgt ctcagaaccc cagacacaag atcaccaagc ggggccagaa cgtgaccttc    120
agatgcgacc ctatcagcga gcacaaccgg ctgtactggt acagacagac actcggccag    180
ggacctgagt tcctgaccta cttccagaac gaggcccagc tggaaaagag cagactgctg    240
agcgacagat tcagcgccga aagacccaag ggcagcttca gcaccctgga aatccagaga    300
accgagcagg gcgacagcgc catgtatctg tgtgcctctt ctctcgtgcg ggcatcgag     360 gcctttttg gccaaggcac cagactgacc gtggtggaag atctccggaa cgtgaccccc    420
cctaaagtga ccctgttcga acccagcaag gccgagatcg ccaacaagca gaaagccacc    480
ctcgtgtgcc tggccagagg cttcttcccc gaccatgtgg aactgtcttg gtgggtcaac    540
ggcaaagagg tgcacagcgg agtgtccacc gaccctcagg cctacaaaga gagcaactac    600
agctactgcc tgagcagcag actgcgggtg tccgccacct tctggcacaa ccccggaac    660 cacttcagat gccaggtgca gttcacggc ctgagcgaag aggacaagtg gcccgaaggc    720 tccccaagc ccgtgaccca gaatatctct gccgaggcct ggggcagagc cgactgtgga    780
attaccagcg ccagctacca ccagggcgtg ctgtctgcca ccatcctgta cgagatcctg    840
ctgggcaagg ccaccctgta cgccgtgctg gtgtctggcc tggtgctgat ggccatggtc    900
aagaagaaga acagctga                                                  918
```

```
<210> SEQ ID NO 116
<211> LENGTH: 18
<212> TYPE: DNA
<213> ORGANISM: Artificial Sequence
<220> FEATURE:
<223> OTHER INFORMATION: Codon optimized sequence of homo sapiens

<400> SEQUENCE: 116
gacagctcct ccacctac                                                   18
```

```
<210> SEQ ID NO 117
<211> LENGTH: 21
<212> TYPE: DNA
<213> ORGANISM: Artificial Sequence
<220> FEATURE:
<223> OTHER INFORMATION: Codon optimized sequence of homo sapiens

<400> SEQUENCE: 117
attttttcaa atatggacat g                                               21
```

```
<210> SEQ ID NO 118
```

```
<211> LENGTH: 24
<212> TYPE: DNA
<213> ORGANISM: Artificial Sequence
<220> FEATURE:
<223> OTHER INFORMATION: Codon optimized sequence of homo sapiens

<400> SEQUENCE: 118
tgtgcagaga aatggatcat cttt                                           24

<210> SEQ ID NO 119
<211> LENGTH: 15
<212> TYPE: DNA
<213> ORGANISM: Artificial Sequence
<220> FEATURE:
<223> OTHER INFORMATION: Codon optimized sequence of homo sapiens

<400> SEQUENCE: 119
agcgagcaca accgg                                                     15

<210> SEQ ID NO 120
<211> LENGTH: 18
<212> TYPE: DNA
<213> ORGANISM: Artificial Sequence
<220> FEATURE:
<223> OTHER INFORMATION: Codon optimized sequence of homo sapiens

<400> SEQUENCE: 120
ttccagaacg aggcccag                                                  18

<210> SEQ ID NO 121
<211> LENGTH: 39
<212> TYPE: DNA
<213> ORGANISM: Artificial Sequence
<220> FEATURE:
<223> OTHER INFORMATION: Codon optimized sequence of homo sapiens

<400> SEQUENCE: 121
tgtgccagca gcctgaccac acctgacggc tacacattt                           39

<210> SEQ ID NO 122
<211> LENGTH: 382
<212> TYPE: DNA
<213> ORGANISM: Artificial Sequence
<220> FEATURE:
<223> OTHER INFORMATION: Codon optimized sequence of homo sapiens

<400> SEQUENCE: 122
atgaagacat ttgctggatt ttcgttcctg tttttgtggc tgcagctgga ctgtatgagt    60
agaggagagg atgtggagca gagtctttc ctgagtgtcc gagagggaga cagctccgtt    120
ataaactgca cttacacaga cagctcctcc acctacttat actggtataa gcaagaacct   180
ggagcaggtc tccagttgct gacgtatatt ttttcaaata tggacatgaa acaagaccaa   240
agactcactg ttctattgaa taaaaaggat aaacatctgt ctctgcgcat tgcagacacc   300
cagactgggg actcagctat ctacttctgt gcagagaaat ggatcatctt tggaaagggg   360
acacgacttc atattctccc ca                                            382

<210> SEQ ID NO 123
<211> LENGTH: 397
<212> TYPE: DNA
<213> ORGANISM: Artificial Sequence
<220> FEATURE:
<223> OTHER INFORMATION: Codon optimized sequence of homo sapiens

<400> SEQUENCE: 123
```

```
atgggcacaa gcctgctgtg ttggatggcc ctgtgtctgc tgggagccga tcatgccgat    60
acgggagtgt ctcagaaccc cagacacaag atcaccaagc ggggccagaa cgtgaccttc   120
agatgcgacc ctatcagcga gcacaaccgg ctgtactggt acagacagac actcggccag   180
ggacctgagt tcctgaccta cttccagaac gaggcccagc tggaaaagag cagactgctg   240
agcgacagat tcagcgccga aagacccaag ggcagcttca gcaccctgga aatccagaga   300
accgagcagg gcgacagcgc catgtatctg tgtgccagca gcctgaccac acctgacggc   360
tacacatttg gcagcggcac cagactgacc gtggtgg                            397

<210> SEQ ID NO 124
<211> LENGTH: 795
<212> TYPE: DNA
<213> ORGANISM: Artificial Sequence
<220> FEATURE:
<223> OTHER INFORMATION: Human (codon optimized) with murinized constant
      region

<400> SEQUENCE: 124
atgaagacat tgctggatt ttcgttcctg tttttgtggc tgcagctgga ctgtatgagt    60
agaggagagg atgtggagca gagtctttc ctgagtgtcc gagagggaga cagctccgtt   120
ataaactgca cttacacaga cagctcctcc acctacttat actggtataa gcaagaacct   180
ggagcaggtc tccagttgct gacgtatatt ttttcaaata tggacatgaa acaagaccaa   240
agactcactg ttctattgaa taaaaaggat aaacatctgt ctctgcgcat tgcagacacc   300
cagactgggg actcagctat ctacttctgt gcagagaaat ggatcatctt tggaaagggg   360
acacgacttc atattctccc caacatccag aatccggagc ccgccgtata ccagctgaag   420
gaccctagaa gccaggacag cacctgtgc ctgttcaccg acttcgacag ccagatcaac   480
gtgcccaaga ccatggaaag cggcaccttc atcaccgaca agacagtgct ggacatgaag   540
gccatggaca gcaagtccaa cggcgcaatc gcctggtcca accagaccag cttcacatgc   600
caggacatct tcaaagagac aaacgccaca taccccagca gcgacgtgcc ctgtgatgcc   660 acctgacag agaagtcctt cgagacagac atgaacctga acttccagaa tctgtccgtg   720
atgggcctga gaatcctgct gctgaaggtg gccggcttca atctgctgat gaccctgcgg   780
ctgtggtcca gctga                                                    795

<210> SEQ ID NO 125
<211> LENGTH: 918
<212> TYPE: DNA
<213> ORGANISM: Artificial Sequence
<220> FEATURE:
<223> OTHER INFORMATION: Human (codon optimized) with murinized constant
      region

<400> SEQUENCE: 125
atgggcacaa gcctgctgtg ttggatggcc ctgtgtctgc tgggagccga tcatgccgat    60
acgggagtgt ctcagaaccc cagacacaag atcaccaagc ggggccagaa cgtgaccttc   120
agatgcgacc ctatcagcga gcacaaccgg ctgtactggt acagacagac actcggccag   180
ggacctgagt tcctgaccta cttccagaac gaggcccagc tggaaaagag cagactgctg   240
agcgacagat tcagcgccga aagacccaag ggcagcttca gcaccctgga aatccagaga   300
accgagcagg gcgacagcgc catgtatctg tgtgccagca gcctgaccac acctgacggc   360
tacacatttg gcagcggcac cagactgacc gtggtggaag atctccggaa cgtgaccccc   420
```

```
cctaaagtga ccctgttcga acccagcaag gccgagatcg ccaacaagca gaaagccacc    480
ctcgtgtgcc tggccagagg cttcttcccc gaccatgtgg aactgtcttg gtgggtcaac    540
ggcaaagagg tgcacagcgg agtgtccacc gaccctcagg cctacaaaga gagcaactac    600
agctactgcc tgagcagcag actgcgggtg tccgccacct tctggcacaa cccccggaac    660
cacttcagat gccaggtgca gtttcacggc ctgagcgaag aggacaagtg gcccgaaggc    720
tcccccaagc ccgtgaccca gaatatctct gccgaggcct ggggcagagc cgactgtgga    780
attaccagcg ccagctacca ccagggcgtg ctgtctgcca ccatcctgta cgagatcctg    840
ctgggcaagg ccaccctgta cgccgtgctg gtgtctggcc tggtgctgat ggccatggtc    900
aagaagaaga acagctga                                                  918
```

```
<210> SEQ ID NO 126
<211> LENGTH: 31
<212> TYPE: PRT
<213> ORGANISM: Homo sapiens

<400> SEQUENCE: 126

Ala Arg Phe Ala Glu Gly Leu Glu Lys Leu Lys Glu Cys Val Leu His
1               5                   10                  15

Asp Asp Leu Leu Glu Ala Arg Arg Pro Arg Ala His Glu Cys Leu
            20                  25                  30

<210> SEQ ID NO 127
<211> LENGTH: 5
<212> TYPE: PRT
<213> ORGANISM: Homo sapiens

<400> SEQUENCE: 127

Asp Asp Leu Leu Glu
1               5
```